(12) United States Patent
Aihara

(10) Patent No.: US 9,033,909 B2
(45) Date of Patent: May 19, 2015

(54) SHUNT VALVE FOR TREATMENT OF HYDROCEPHALUS

(76) Inventor: Yasuo Aihara, Tokyo (JP)

( * ) Notice: Subject to any disclaimer, the term of this patent is extended or adjusted under 35 U.S.C. 154(b) by 343 days.

(21) Appl. No.: 13/642,931

(22) PCT Filed: Apr. 20, 2011

(86) PCT No.: PCT/JP2011/060198
§ 371 (c)(1),
(2), (4) Date: Dec. 7, 2012

(87) PCT Pub. No.: WO2011/136241
PCT Pub. Date: Nov. 3, 2011

(65) Prior Publication Data
US 2013/0085441 A1 Apr. 4, 2013

(30) Foreign Application Priority Data

Apr. 26, 2010 (JP) .................................. 2010-100831

(51) Int. Cl.
*A61M 5/00* (2006.01)
*A61M 27/00* (2006.01)
*A61M 5/142* (2006.01)

(52) U.S. Cl.
CPC ........... *A61M 27/006* (2013.01); *A61M 27/002* (2013.01); *A61M 5/14276* (2013.01)

(58) Field of Classification Search
CPC .................. A61M 27/006; A61M 2205/6054; A61M 2205/3515; A61M 5/16883; A61M 2005/8278; A61M 27/002; A61M 5/14276
USPC ........ 604/8–10, 246–248; 251/118, 126, 127, 251/205, 208; 138/42–45
See application file for complete search history.

(56) References Cited

U.S. PATENT DOCUMENTS 4,551,128 A * 11/1985 Hakim et al. ..................... 604/9
4,588,394 A * 5/1986 Schulte et al. .................... 604/9
(Continued)

FOREIGN PATENT DOCUMENTS

JP 60-139257 7/1985
JP 63-317161 12/1988
(Continued)

OTHER PUBLICATIONS

International Search Report issued Aug. 2, 2011 in International (PCT) Application No. PCT/JP2011/060198.
(Continued)

*Primary Examiner* — Philip R Wiest
(74) *Attorney, Agent, or Firm* — Wenderoth, Lind & Ponack, L.L.P.

(57) ABSTRACT

[Problem]
Disclosed is a shunt valve for treatment of hydrocephalus such that the flow rate of cerebrospinal fluid drained from the brain ventricles can be freely regulated without drastically changing the intraventricular pressure when the pressure thereof becomes abnormal after a transplant.
[Means to Solve the Problem]
A shunt valve for treatment of hydrocephalus which regulates the drainage amount of cerebrospinal fluid from the ventricles, and comprises a cured plastic substrate for stabilizing in a prescribed position, an inflow connector formed in a cylindrical shape to which a rear end of a ventricular catheter is connected, a first valve pressure variable device which regulates an increase and decrease in the flow rate of the cerebrospinal fluid with a first on-off valve according to changes in the intraventricular pressure and is capable of changing the opening and closing pressure into a plurality of levels, a second valve pressure variable device which regulates the increase and decrease of the flow rate of the cerebrospinal fluid with a second on-off valve according to changes in the fluid pressure of the cerebrospinal fluid drained from an outflow channel of the first valve pressure variable device and is capable of changing the opening and closing pressure into a plurality of levels, and an outflow connector formed in a cylindrical shape to which a rear end of a peritoneal catheter is connected.

32 Claims, 43 Drawing Sheets

(56) References Cited

U.S. PATENT DOCUMENTS

| | | |
|---|---|---|
| 4,675,003 A | 6/1987 | Hooven |
| 4,729,762 A | 3/1988 | Doumenis |
| 4,776,838 A | 10/1988 | Sainte-Rose et al. |
| 4,867,741 A | 9/1989 | Portnoy |
| 5,843,013 A | 12/1998 | Lecuyer et al. |
| 5,928,182 A | 7/1999 | Kraus et al. |
| 2004/0193094 A1 | 9/2004 | Kraus |
| 2007/0004999 A1 | 1/2007 | Miethke |
| 2007/0093741 A1 | 4/2007 | Miethke |

FOREIGN PATENT DOCUMENTS

| | | |
|---|---|---|
| JP | 10-5326 | 1/1998 |
| JP | 11-146911 | 6/1999 |
| JP | 2004-290678 | 10/2004 |
| JP | 2005-13727 | 1/2005 |
| JP | 2006-509610 | 3/2006 |

OTHER PUBLICATIONS

Japanese Notification of Reason for Refusal issued Dec. 5, 2013 in corresponding Japanese Patent Application No. 2010-100831 with English translation.

Japan Medtronic, Inc. Product Catalog [PS Medical Strata Variable Shunt Valve for Treatment of Hydrocephalus], Dec. 2009.

* cited by examiner

SHUNT VALVE FOR TREATMENT OF HYDROCEPHALUS

TECHNICAL BACKGROUND

The present invention relates to a shunt valve for treatment of hydrocephalus, in particular, a shunt valve for treatment of hydrocephalus which makes it possible to easily regulate the flow rate of cerebrospinal fluid which drains into a peritoneal catheter without drastically changing the intraventricular pressure in the brain ventricles when an abnormality has occurred in the production of cerebrospinal fluid in the brain ventricles after a transplant.

BACKGROUND ART

In general, hydrocephalus is a condition characterized by excessive accumulation of cerebrospinal fluid inside the brain (brain ventricles) which causes pressure in the brain and associated with various symptoms, and can affect individuals of all ages.

Brain ventricles are cavities inside the brain. There are four ventricles: a pair of lateral ventricles on the left and right side, the third ventricle and the fourth ventricle.

The pair of lateral ventricles are located inside the left and right cerebral hemispheres and extend into the frontal lobe, parietal lobe, temporal lobe and occipital lobe, communicating with the third ventricle through an interventricular foramen (foramen of Monro) which is bounded by a transparent septum.

The third ventricle is a ventricle located inside the diencephalon, the side walls thereof communicating with the optic thalamus and the sub-wall and side sub-wall thereof communicating with the hypothalamus. The third ventricle also communicates with the fourth ventricle through the cerebral aqueduct which is a narrow tubular ventricle penetrating the mesencephalic region.

Furthermore, the fourth ventricle is a ventricle located inside the rhombencephalon and is connected to the cerebral aqueduct at an upper side thereof and with a central canal at a lower side thereof, which is a narrow tubular ventricle connecting to a lower side of the oblongatal fourth ventricle, and continues from the cerebral aqueduct to the central canal, communicating with the subarachnoid cavity through the lateral apertures of the fourth ventricle (foramina of Lushka) and the median aperture of the fourth ventricle (foramen of Magendie).

The four ventricles are always filled with cerebrospinal fluid and are communicating with each other through tracts, each ventricle storing a specific amount of cerebrospinal fluid which circulates therein.

The cerebrospinal fluid circulating in the ventricles is believed to flow from the lateral ventricles→foramen of Monro→the third ventricle→cerebral aqueduct→the fourth ventricle→foramina of Lushka/foramen of Magendi→cisterns→superior sagittal sinus.

The cerebrospinal fluid is produced by the choroid plexus located in the ventricles and flows from the lateral ventricles, third ventricle and fourth ventricle into the subarachnoid cavity of the brain and is then absorbed into the venous system via the arachnoid granulation of the subarachnoid cavity in the parietal region. Thus, the cerebrospinal fluid is a transparent fluid which is present inside the arachnoid mater as well as in the entire brain, acting as a suspension fluid with respect to the brain and absorbing shocks to the brain caused by sudden movements of the head, as well as removing substances produced by partial brain activity, and therefore has a cerebroprotective action.

Hydrocephalus is characterized by excessive accumulation of cerebrospinal fluid inside the brain (ventricles) due to some cause. Some causes of such excessive accumulation of cerebrospinal fluid inside the brain (ventricles) may include: overproduction of the cerebrospinal fluid by the choroid plexus, impaired resorption of the cerebrospinal fluid even in the case of normal production, or obstruction of the cerebrospinal fluid flow due to clear obstacle in the circulatory pathways of the cerebrospinal fluid.

Hydrocephalus is classified into idiopathic normal pressure hydrocephalus and secondary normal pressure hydrocephalus. The former develops in the case of inadequate cerebrospinal fluid circulation caused by a clear obstacle in the circulatory pathways of the cerebrospinal fluid anywhere inside the ventricles, such as for instance narrowing of the cerebral aqueduct. The latter develops in the case of inadequate cerebrospinal fluid circulation which caused by identifiable causes such as subarachnoid hemorrhage, head injury, cerebral meningitis.

At present, hydrocephalus is treated medically through drugs, etc. but it cannot be cured and surgical treatment methods are being introduced. A commonly used surgical treatment method is called shunt technology. A shunt is a device which channels a portion of the excess cerebrospinal fluid outside of the skull; a procedure called drainage, and uses a shunt valve to create a new flow path for the cerebrospinal fluid.

Common shunts consist of 2 catheters and 1 one-way shunt valve. The shunt valve is meant to regulate the flow of the cerebrospinal fluid outside of the ventricles and the pressure of the cerebrospinal fluid outside of the ventricles. In general, when the pressure of the intraventricular cerebrospinal fluid increases, the excess cerebrospinal fluid drains to a lower cavity via the shunt valve.

There are a number of methods which employ the shunt technology of causing the cerebrospinal fluid which was not absorbed to be reabsorbed at other locations using the shunt valve.

(1) Ventriculo-Peritoneal Shunt (VP Shunt)

According to this method, a tube is inserted into the enlarged ventricle while its distal end is inserted inside the abdomen (peritoneal cavity) and the cerebrospinal fluid is reabsorbed in the abdomen.

(2) Lumbar-Peritoneal Shunt (LP Shunt)

According to this method, a tube is inserted in the subarachnoid cavity in the lumbar region while its distal end is inserted inside the peritoneal cavity for re-absorption of the cerebrospinal fluid inside the abdomen.

(3) Ventriculo-atrial shunt (VA shunt)

According to this method, the tube from the enlarged ventricle is inserted from the cervical vein into the right atrium and the cerebrospinal fluid is reabsorbed in the blood.

The most widely used method is the ventriculo-peritoneal shunt (VP shunt).

The conventional shunt valve for treatment of hydrocephalus as employed in this shunt technology shunts the excess cerebrospinal fluid which accumulated inside the head (ventricles) and was not absorbed in the brain through a tube to another location in the body so the fluid is reabsorbed at various locations inside the body.

The shunt valves for treatment of hydrocephalus are classified into pressure control valves whereby the flow rate of cerebrospinal fluid is controlled by the pressure setting at the valve and flow rate regulating valves whereby the flow rate is automatically regulated by the cerebrospinal fluid pressure. Typically, there are 3 types of pressure control valves depending on the pressure fluctuation range: low-pressure (for instance, pressure fluctuates in the range of 15-50 mm $H_2O$ depending on the flow rate of the spinal fluid), medium pressure (for instance, pressure fluctuates in the range of 50-90 mm $H_2O$ depending on the flow rate of the spinal fluid) and high pressure (for instance, pressure fluctuates in the range from 90-150 mm $H_2O$ depending on the flow rate of the spinal fluid). The choice of valve pressure is based on preoperative cerebrospinal fluid pressure, clinical course, cerebral ventricle size, age, etc. of the patient.

Flow rate regulating valves automatically change the sectional area of the valve system where the cerebrospinal fluid flows depending on the cerebrospinal fluid pressure so that the intraventricular pressure is maintained at a constant range as much as possible. One disadvantage of the flow rate regulating valves is that they cannot completely nullify the siphoning effect which occurs due to the difference in the water pressure caused by the difference in the height of the brain and abdomen, and therefore a satisfactory cerebrospinal fluid flow rate is not obtained in the case of low pressure hydrocephalus.

In recent years, variable pressure shunts have been introduced for the treatment of hydrocephalus, whereby valve adjustment is carried out magnetically to regulate the cerebrospinal fluid flow rate (refer to Patent Literature 1, and Non-Patent Literature 2, for instance). The object of the present invention is such a pressure variable shunt valve for treatment of hydrocephalus.

PRIOR ART LITERATURE

Patent Literature

[Patent Literature 1]
Japanese Published Unexamined Application JP 2005-13727

Non-Patent Literature

[Non-Patent Literature 1]
Japan Medtronic, Inc. Product Catalog [PS Medical Strata Variable Shunt Valve for Treatment of Hydrocephalus]

SUMMARY OF THE INVENTION

Problems to be Solved by the Invention

The pressure variable shunt valve for treatment of hydrocephalus 500 as described in the Non-Patent Literature 1 is a single-unit device and has a shunt main body 520 which is mounted to a cured plastic substrate 510 and a flexible silicone elastomer membrane 530 which covers the entire body. The silicone elastomer is a type of silicone that has a Si—O—Si combination in its molecules and when a curing catalyst such as peroxide or a platinum compound, etc. is added thereto, it cures like an elastomer or cures through partial crystallization.

The cured plastic substrate 510 is made of polypropylene (PP), for instance, which is a thermoplastic resin very similar to high-density polyethylene, such as a polymeric compound (polymer) obtained through addition polymerization of propylene, and has a low specific gravity, superior thermal resistance, strongly acidic and alkaline properties, resistance to repeated bending and great tensile strength.

The shunt main body 520 has a reservoir 540 and one valve pressure variable device 550. It also has an inflow connector 530 which is mounted on the cerebrospinal fluid inflow side of the reservoir 540, a chamber 560 which is provided on the cerebrospinal fluid outflow side of the valve pressure variable device 550, and an outflow connector 570 which is mounted on the cerebrospinal fluid outflow side of the chamber 560. A peritoneal catheter is connected to the inflow connector 530 and a peritoneal catheter is connected to the outflow connector 570.

The cerebrospinal fluid which accumulated in the reservoir 540 in a specific amount drains into the valve pressure variable device 550 thanks to its own pressure as produced inside the ventricle. The valve pressure variable device 550 is constituted of a cover 551, and a case-shaped main body 555 which has a step-wise plate formed on the bottom surface thereof and accommodates a ball 552, a spring 553 and a rotor 554. The cover 551 is threadably mounted on the main body 555 so as to hermetically seal it.

The cover 551 has a round shape and has a tapered orifice 556 formed in the center thereof so as to allow passage of the cerebrospinal fluid which drains from the reservoir 540. The ball 552 acts as a valve which opens and closes the orifice 556 which opens towards the inner wall of the cover 551 where the outflow side of the orifice 556 of the cover 551 and the cerebrospinal fluid flow rate is adjusted by the depressing force of the ball 551 against the opening of the orifice.

The rotor 554 has a discoid shape and accommodates the coil-shaped spring 553 in an upper surface thereof, with the spring depressing the ball 552 against the opening of the orifice in the inner wall surface side of the cover 551. The rotor 554 is slidably provided on the upper surface of the plate in the case and has a plurality of legs formed on a lower surface thereof which project downwards and lower the skid resistance between the rotor 554 and the plate surface. More specifically, the rotor 554 is mounted on the plate of the main body 555, and the legs formed in the lower surface of the rotor 554 lower the contact resistance with the plate surface allowing the rotor 554 to easily rotate on the plate of the main body 155.

The plate of the main body 555 has a step-wise shape (for instance, 5 steps), with each step having a height that differs by a certain amount. Accordingly, the position of upper surface of the rotor 554 varies in height depending on the plate of the main body 555 which has the legs formed on the lower surface of the rotor 554 mounted thereon.

The cerebrospinal fluid which flows out of the reservoir 540 forces down the ball 552 which is depressed by the coiled spring 553 in the opening of the orifice 556 as formed in the cover 551 and then flows into the valve pressure variable device 550.

More specifically, when there is a balance between the pressure of the cerebrospinal fluid flowing out of the reservoir 540, e.g. the intraventricular pressure and the pressure of the spring 553 which depresses the ball 552 in the opening portion of the orifice 556 formed in the cover 551, the ball 552 is depressed by the elastic force of the spring 553 and blocks the opening portion of the orifice 556 in the cover 551, preventing the cerebrospinal fluid which flows out of the reservoir 540 to flow into the valve pressure variable device 550 through the orifice 556 in the cover 551.

As the intraventricular cerebrospinal fluid accumulates, the intraventricular pressure rises, leading to an increase in the pressure of the cerebrospinal fluid flowing out of the reservoir 540. The increase in the intraventricular pressure does not cause a change in the pressure of the spring 553 which depresses the ball 552 in the opening portion of the orifice 556 in the cover 551, so that the pressure of the cerebrospinal fluid flowing out of the reservoir 540 becomes higher than the pressure of the spring 553 which depresses the ball 552 in the opening portion of the orifice 556 in the cover 551.

When the pressure of the cerebrospinal fluid flowing out of the reservoir 540 becomes higher than the pressure of the spring 553 which depresses the ball 552, the ball 552 which blocks the opening portion of the orifice 556 in the cover 151 is forced down against the elastic force of the spring 553. The ball 552 is held down against the elastic force of the spring 553 in response to the higher intraventricular pressure. When the ball 552 is held down, the cerebrospinal fluid starts flowing from the clearance between the opening portion of the orifice 556 and the ball 552 formed when the opening portion of the orifice 556 in the cover 551 opens in response to the higher intraventricular pressure, into the valve pressure variable device 550 and continues flowing until a balance is reached between the intraventricular pressure and the pressure of the spring 553 which depresses the ball 552.

As a result of draining into the valve pressure variable device 550, the amount of cerebrospinal fluid inside the reservoir 540 decreases, which means that the amount of intraventricular cerebrospinal fluid decreases as well. Once the intraventricular pressure starts to fall as a result of the decrease in the amount of intraventricular cerebrospinal fluid, the pressure which holds down the ball 552 starts to drop as well and the ball 552 is gradually pushed up by the elastic force of the spring 553. Then, when the balance is restored between the intraventricular pressure and the pressure of the spring 553 which depresses the ball 552 in the opening portion of the orifice 556 in the cover 551, the opening portion of the orifice 556 in the cover 551 is blocked by the ball 552.

Thus, in the valve pressure variable device 550, when the intraventricular pressure becomes high, the ball 552 is held down in response to the outflow pressure of the cerebrospinal fluid from the reservoir 540, causing the opening portion of the orifice 556 in the cover 551 to open and allow the cerebrospinal fluid to flow. Then, once balance is restored between the intraventricular pressure and the pressure of the spring 553 which depresses the ball 552 in the opening portion of the orifice 556 in the cover 551, the ball 552 presses against the opening portion of the orifice 556 in the cover 551 and blocks it, stopping the outflow of intraventricular cerebrospinal fluid.

The depressing force of the ball 552 which is depressed in the opening portion of the orifice 556 in the cover 551 in response to the elastic force of the spring 553 and which acts onto the opening portion of the orifice in the cover 551 is adjusted by adjusting the pressure of the spring 553. As spring 553 has a coil shape, its elastic force increases as it compresses. Accordingly, the elastic force of the spring 553 which is mounted in the upper surface of the rotor 554 is adjusted by altering the distance between the upper surface of the rotor 554 and the inner wall surface of the cover 551.

More specifically, the rotor 554 rotates on the plate of the main body 555 at a predetermined angle so that as the rotor moves upwards by one step starting from the lowermost step on the plate of the main body 555, the position of the upper surface of the rotor 554 moves upwards by one step each time the rotor moves upwards one step on the plate of the main body 555. Adversely, as the rotor moves downwards by one step starting from the uppermost step on the plate of the main body 555, the position of the upper surface of the rotor 554 moves downwards by one step each time the rotor moves downwards one step on the plate of the main body 555. As the position of the upper surface of the rotor 554 changes, the degree of contraction and expansion of the spring 553 as mounted in the upper surface of the rotor 554 changes as well. In turn, as the degree of expansion and contraction of the spring 553 changes, the depressing force of the ball 552 acting on the opening portion of the orifice in the inner wall surface of the cover 551 changes in relation to the elastic force of the spring 553 which fluctuates according to the degree of contraction and expansion of the spring 553.

More specifically, when the legs formed in the lower surface of the rotor 554 move upwards (or downwards) by one step on the plate, the position of the upper surface of the rotor 554 moves upwards (or otherwise, downwards) according to the height position of the plate of the main body 555, and the spring 553 which is mounted between the upper surface of the rotor 554 and the upper portion of the inner wall of the cover 551 compresses (or expands), so that the depressing force produced as a result of the elastic action of the spring 553 acting on the ball 552 which is supported at the leading end of the spring 553 becomes strong (or weak).

When the inflow pressure of the cerebrospinal fluid flowing out of the reservoir 540 into the orifice 556 of the cover 551 is constant (does not fluctuate), as the rotor 554 rotates and moves upwards (or downwards) on the plate by one step, the depressing force produced by the elastic action of the spring 553 and acting onto the ball 552 increases (or decreases), in comparison with the force before the rotor 554 rotates on the plate of the main body 555 and moves upwards (or downwards) by one step, only by an amount proportional to the elastic force of the spring 553 which changes in relation to the change by one step in the height position of the plate of the main body 555.

More specifically, if the pressure of the cerebrospinal fluid which accumulates in the reservoir 540 via the orifice 556 formed in the cover 551 remains constant, the depressing force produced by the spring 553 and acting onto the ball 552 increases, and the clearance between the orifice 556 and the ball 552 becomes smaller than prior to the state when the plate of the main body 555 has been moved upwards by one step by the action of the rotor 554. This reduces the amount of cerebrospinal fluid which flows from the reservoir 540 into the valve pressure variable device 550.

A chamber 160 is provided on the cerebrospinal fluid outflow side in the main body 555 of the valve pressure variable device 550. Patients with a shunt main body 120 transplant include not necessarily only bedridden persons, but also a large number of persons who get up and perform their normal daily activities. Thus, when a patient with a shunt main body 120 transplant stands up from a lying down position, the cerebrospinal fluid inside the peritoneal catheter has a tendency to rapidly drain into the peritoneal cavity under the influence of gravity. As a result, a negative pressure is created inside the peritoneal catheter which will act onto the cerebrospinal fluid outflow side of the main body 555 in the valve pressure variable device 550 to which the peritoneal catheter is connected.

As this negative pressure works in the direction that the ball 552 is lowered from the opening portion of the orifice 556 in the cover 551, when the negative pressure acts onto the cerebrospinal fluid outflow side in the main body 555, a force (negative pressure) which pulls the ball 552 (lowers the ball 552) towards the cerebrospinal fluid outflow side of the main body 555 acts onto the ball 552 and this pressure is contrary to the positive pressure produced by the elastic force of the spring 553 which depresses the ball 552 into the opening portion of the orifice 556 in the cover 551.

When patients suddenly sit up from a lying down position, in other words, from a state where the intraventricular pressure and the pressure of the spring 553 which depresses the ball 552 in the opening portion of the orifice 556 in the cover 551 are well balanced due to the action of the valve pressure variable device 550, the amount of intraventricular cerebrospinal fluid decreases causing a sharp drop in the intraventricular pressure.

When the amount of intraventricular cerebrospinal fluid decreases causing a sharp drop in the intraventricular pressure, the ventricle becomes smaller and narrower, and the so-called slit ventricle condition starts to occur, accompanied by symptoms such as sharp headache, sudden impaired awareness, etc. The decrease in the amount of intraventricular cerebrospinal fluid causes a sharp drop in the cerebrospinal fluid pressure, subdural hematoma, subdural hygroma or collapse of the lateral ventricle (slit ventricle syndrome). This condition occurs when a drastic reduction in the ventricle size causes the leading end of the catheter to interfere with the ventricle wall and blocks the shunt.

The chamber 160 prevents a sudden drainage of the intraventricular cerebrospinal fluid as well as a sudden drop in the intraventricular pressure in patients who suddenly sit up from a lying down position. The chamber 160 is provided with a check valve which opens when the cerebrospinal fluid is forced out due to high intraventricular pressure, and closes when a negative pressure is created inside the peritoneal catheter to control the siphon effect of the cerebrospinal fluid. The chamber 160 is constituted of a cavity which primarily collects the cerebrospinal fluid which drains out normally from the ventricle when the valve closes in the event of negative pressure.

Provision of the chamber 160 is not required in bedridden patients.

In the case of this conventional shunt valve for treatment of hydrocephalus, when the cerebrospinal fluid produced in the ventricles builds up in excess inside the ventricles causing an increase in the intraventricular pressure, the ball 552 which is being depressed from the inner side of the inlet port of the cerebrospinal fluid in the valve pressure variable device 550 is being held down under the outflow pressure of the cerebrospinal fluid draining from the reservoir 540 and opens the opening portion of the orifice 556 in the cover 551. As a result, the excess buildup of cerebrospinal fluid inside the ventricle starts flowing into the valve pressure variable device 550 and the intraventricular pressure drops as the intraventricular cerebrospinal fluid decreases.

Thus, the outflow pressure of the cerebrospinal fluid draining from the reservoir 540 decreases together with the decrease in the intraventricular cerebrospinal fluid amount, and the force that holds down the ball 552 which is being depressed in the opening portion of the orifice 556 of the cover 551 becomes weaker as well. In time, the balance is reestablished between the intraventricular pressure and the pressure of the spring 553 which depresses the ball 552 in the opening portion of the orifice 556 in the cover 551 and the opening portion of the orifice 556 formed in the cover 551 is blocked by the ball 552.

In patients with a transplant of a shunt valve for treatment of hydrocephalus, ideally, the intraventricular pressure needs to be maintained constant. However, in the conventional shunt valve for treatment of hydrocephalus, as the intraventricular pressure and the flow rate of the cerebrospinal fluid which flows through the opening portion of the orifice 556 in the cover 551 correspond one to one, the intraventricular pressure rises causing the cerebrospinal fluid to flow out of the ventricles into the opening portion of the orifice 556 formed in the cover 551 of the valve pressure variable device 550 and the outflow does not accurately stop even if the intraventricular pressure is restored to a normal value. In some cases, this causes over-drainage of the cerebrospinal fluid and a drop in the intraventricular pressure below normal levels.

Also, in the conventional shunt valve for treatment of hydrocephalus, as the intraventricular pressure and the flow rate of the cerebrospinal fluid which flows through the opening portion of the orifice 556 in the cover 551 correspond one to one, to raise the intraventricular pressure to normal levels in case it drops, the depressing force of the ball 552 which is depressed in the opening portion is regulated to control the flow rate of the cerebrospinal fluid flowing into the opening portion of the orifice 556 so that it flows slowly and in some cases, when the intraventricular pressure reaches normal levels, the intraventricular pressure rises above normal levels without accurately regulating the flow rate of the cerebrospinal fluid.

In the above-described conventional shunt valve for treatment of hydrocephalus, intraventricular pressure is decreased by moving the ball 552 up and down in accordance with the outflow pressure of the cerebrospinal fluid draining from the ventricles through the reservoir 540 to regulate the clearance area of the opening portion of the orifice 556 in the cover 551 and thus control the flow rate of the cerebrospinal fluid.

With this conventional shunt valve for treatment of hydrocephalus, it is impossible to increase or decrease the flow rate of the cerebrospinal fluid draining from the ventricles through the reservoir 140 by very fine amounts while stably maintaining the intraventricular pressure at normal levels.

The object of the present invention is to provide a shunt valve for treatment of hydrocephalus which makes it possible to freely regulate the flow rate of the cerebrospinal fluid draining from the brain ventricles without causing any drastic changes in the intraventricular pressure when pressure thereof becomes abnormal following a transplant.

Means to Solve the Problem

A shunt valve for treatment of hydrocephalus which is implanted between the scalp and skull and serves for regulating a drainage amount of cerebrospinal fluid draining from brain ventricles where it is produced but is not fully absorbed and accumulates therein, when intraventricular pressure exceeds a certain pressure, such that intraventricular pressure is kept at a predetermined value, comprising:

a cured plastic substrate for stabilizing in a prescribed position in an outer periphery of the skull, at an inner side of the scalp;

an inflow connector formed in a cylindrical shape to which a rear end of a ventricular catheter is connected, the ventricular catheter having a needle for tapping inside the ventricles attached at a leading end thereof;

a first valve pressure variable device for regulating an increase and decrease of a flow rate of cerebrospinal fluid flowing in through the ventricular catheter, via the inflow connector and a first on-off valve by regulating the first on-off valve, specifically, by changing a degree of aperture of the first on-off valve in accordance with changes in intraventricular pressure, and which is capable of changing an opening and closing pressure of the first on-off valve which sets a standard flow rate for a cerebrospinal fluid passing therethrough to a plurality of levels;

a second valve pressure variable device for regulating an increase and decrease of a flow rate of cerebrospinal fluid flowing in through a second on-off valve via an outflow tract of the first valve pressure variable device by regulating a second on-off valve, specifically, by changing a degree of aperture of the second on-off valve in accordance with changes in the pressure of cerebrospinal fluid flowing out of the outflow tract of the first valve pressure variable device through the second on-off valve and draining out of the first valve pressure variable device, and which is capable of changing an opening and closing pressure of the second on-off valve which sets a standard flow rate for a cerebrospinal fluid passing therethrough to a plurality of levels; and an outflow connector formed in a cylindrical shape to which a rear end of a peritoneal catheter is connected, the peritoneal catheter having a leading end thereof inserted in a peritoneal cavity;

wherein the inflow connector, the first valve pressure variable device, the second valve pressure variable device and the outflow connector are mounted on the cured plastic substrate, and the device is covered by a flexible silicone elastomer membrane so as to form a flow path for the cerebrospinal fluid such that the cerebrospinal fluid flowing in from the inflow connector flows out through the first on-off valve of the first valve pressure device, and then flows out of the outflow tract in the second valve pressure variable device through the second on-off valve of the second valve pressure variable device, draining out of the outflow connector, and a lower end of the silicone elastomer membrane is tightly attached to the cured plastic substrate to form one integral unit.

Effects of the Invention

According to the present invention, the shunt valve for treatment of hydrocephalus makes it possible to freely regulate the flow rate of the cerebrospinal fluid draining from the brain ventricles without causing any drastic changes in the intraventricular pressure when pressure thereof becomes abnormal following a transplant.

EMBODIMENTS OF THE INVENTION

Figure 1:
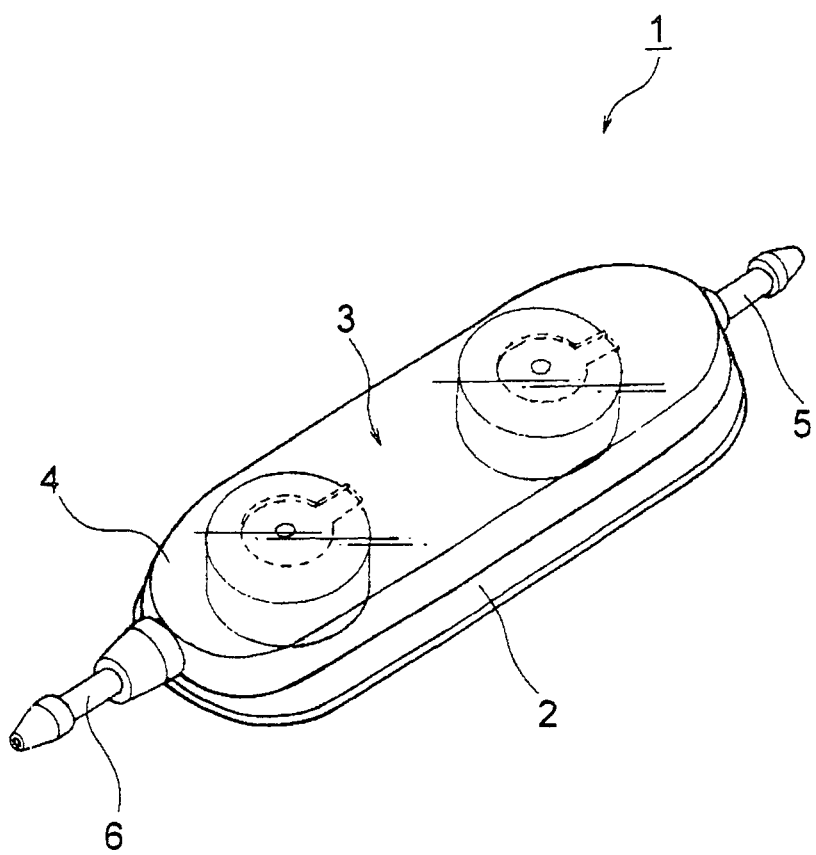
FIG. 1 illustrates a first embodiment of a shunt valve for treatment of hydrocephalus according to the present invention and is an overall perspective view of such shunt valve for treatment of hydrocephalus.

A shunt valve for treatment of hydrocephalus according to the present invention consists of 2 or more tandem variable shunt valves which are mounted in series and form an integral unit.

Next, a description will be given while referring to the drawings.

First Embodiment

A first embodiment of a shunt valve for treatment of hydrocephalus according to the present invention is illustrated in FIGS. 1~6.

FIG. 1 illustrates a first embodiment of a shunt valve for treatment of hydrocephalus according to the present invention and is an overall perspective view of such shunt valve for treatment of hydrocephalus.

Figure 2:
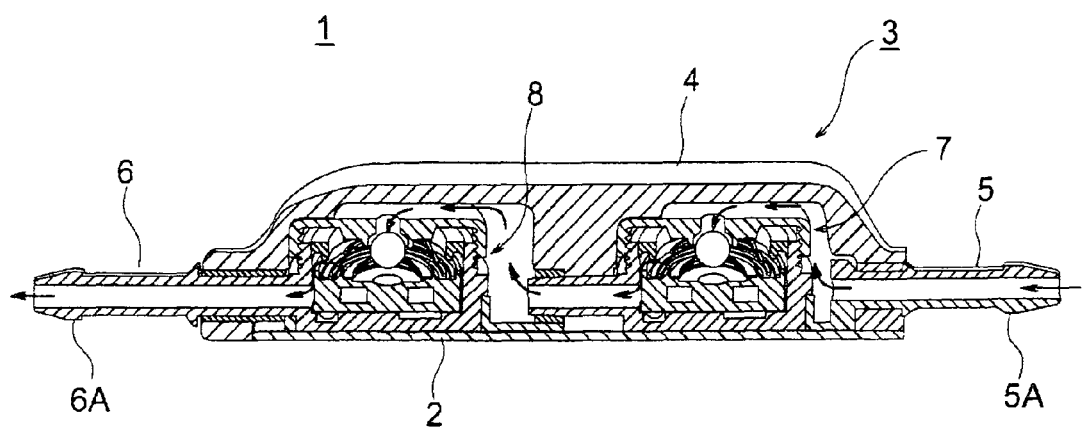
FIG. 2 is a vertical cross-sectional view of the shunt valve for treatment of hydrocephalus as illustrated in FIG. 1.

FIG. 2 is a vertical cross-sectional view of the shunt valve for treatment of hydrocephalus as illustrated in FIG. 1.

Figure 3:
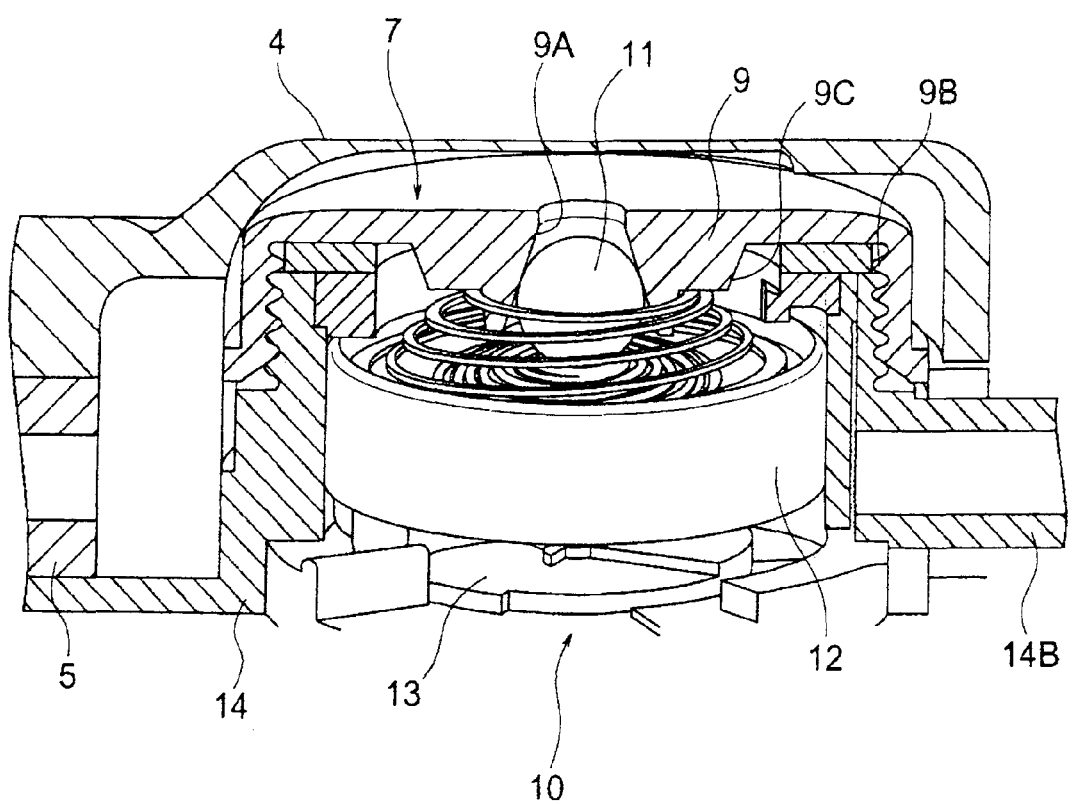
FIG. 3 is an overall view of a cross section of a portion of a first valve pressure variable device of the shunt valve for treatment of hydrocephalus as illustrated in FIG. 1.

FIG. 3 is an overall view of a cross section of a portion of a first valve pressure variable device of the shunt valve for treatment of hydrocephalus as illustrated in FIG. 1.

Figure 4:
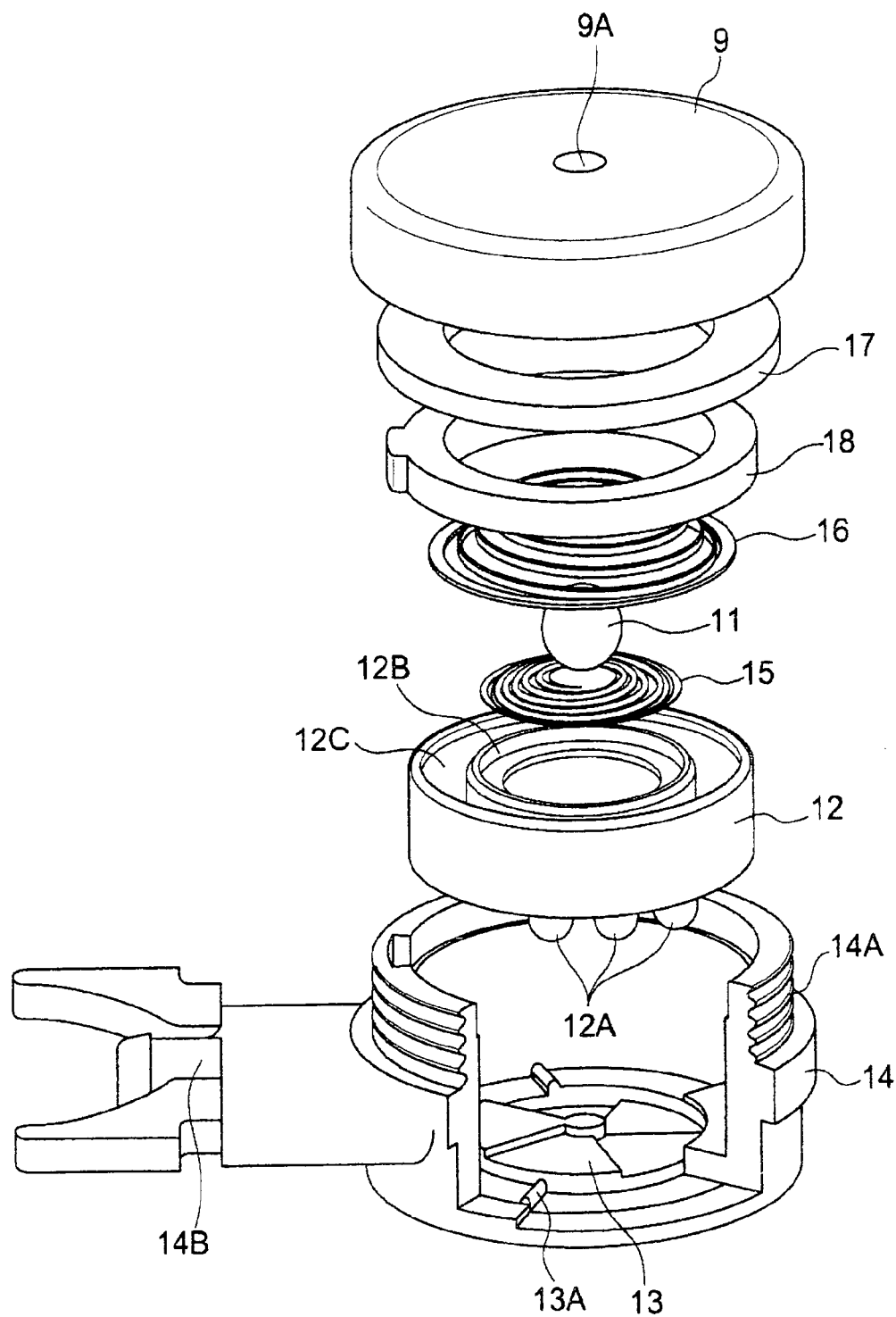
FIG. 4 is an assembly perspective view of the first valve pressure variable device of the shunt valve for treatment of hydrocephalus as illustrated in FIG. 3.

FIG. 4 is an assembly perspective view of a first valve pressure variable device of the shunt valve for treatment of hydrocephalus as illustrated in FIG. 3.

Figure 5:
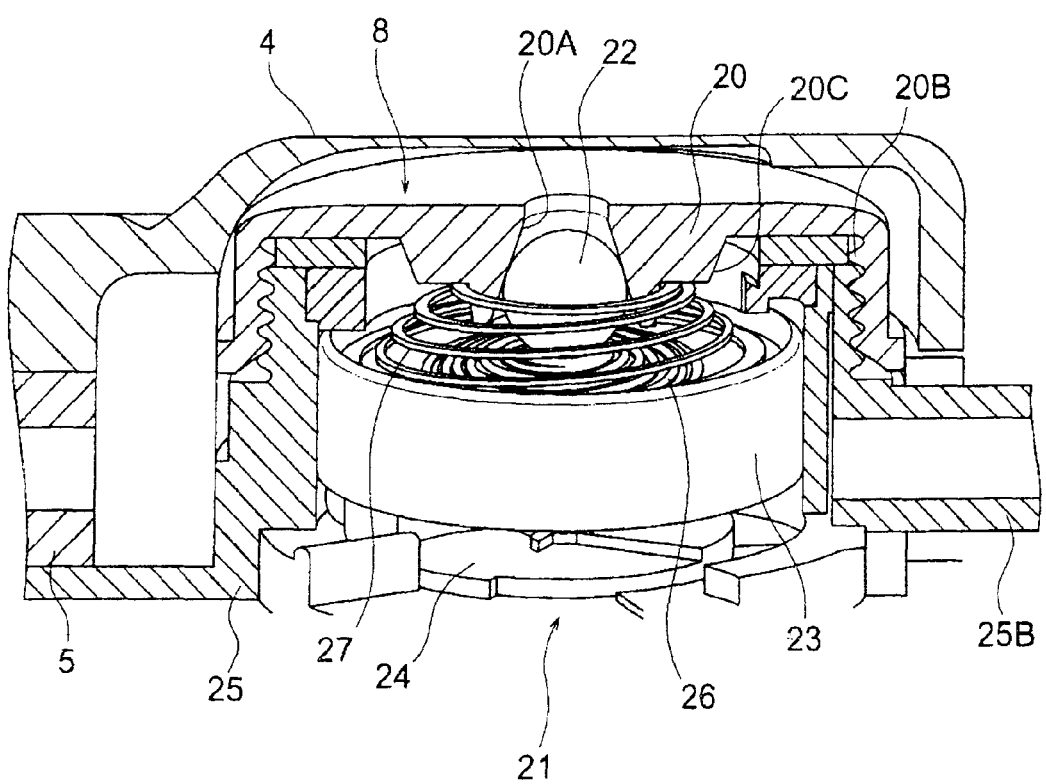
FIG. 5 is an overall view of a cross section of a portion of a second valve pressure variable device of the shunt valve for treatment of hydrocephalus as illustrated in FIG. 1.

FIG. 5 is an overall view of a cross section of a portion of a second valve pressure variable device of the shunt valve for treatment of hydrocephalus as illustrated in FIG. 1.

Figure 6:
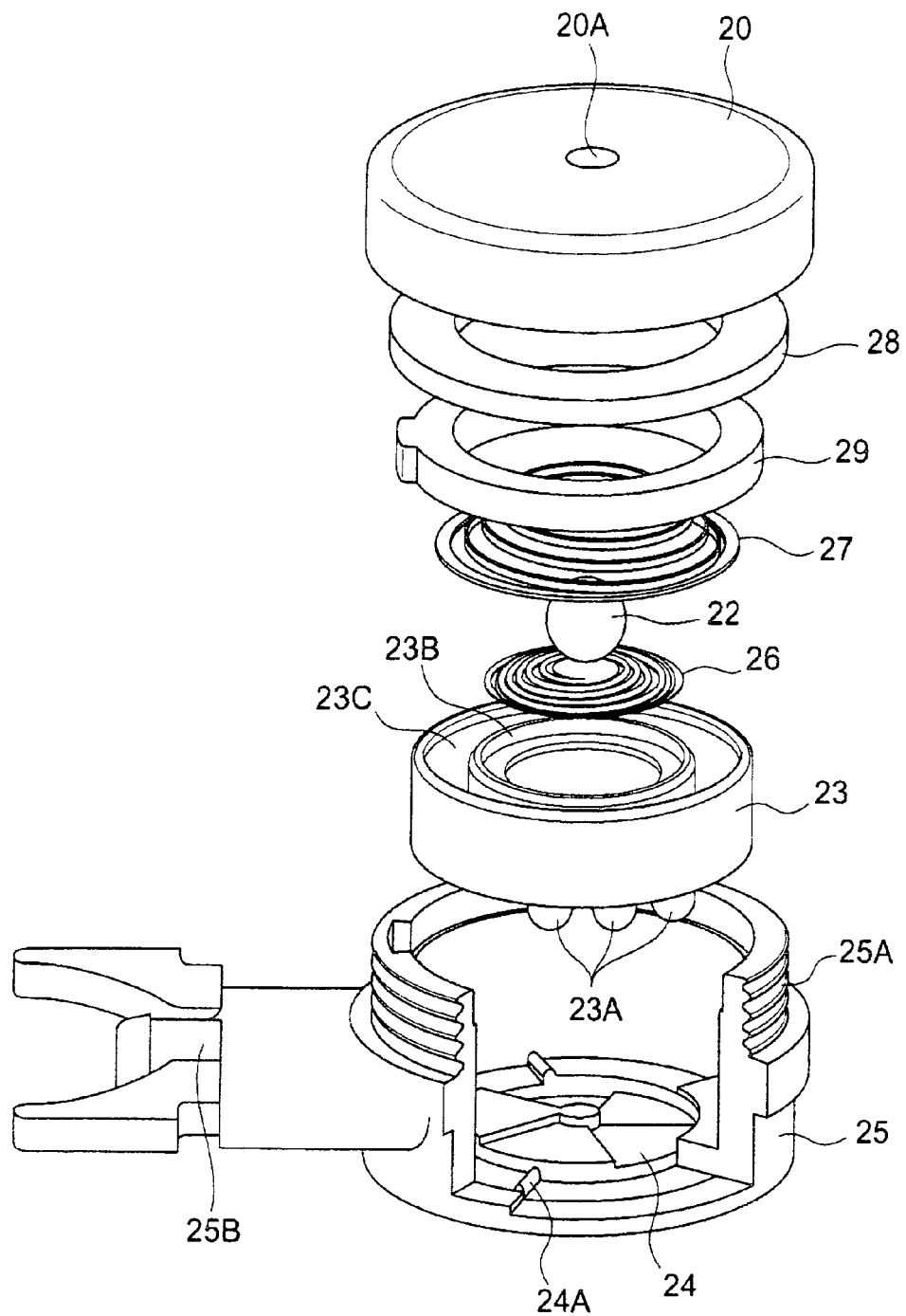
FIG. 6 is an assembly perspective view of the second valve pressure variable device of the shunt valve for treatment of hydrocephalus as illustrated in FIG. 5.
Figure 7:
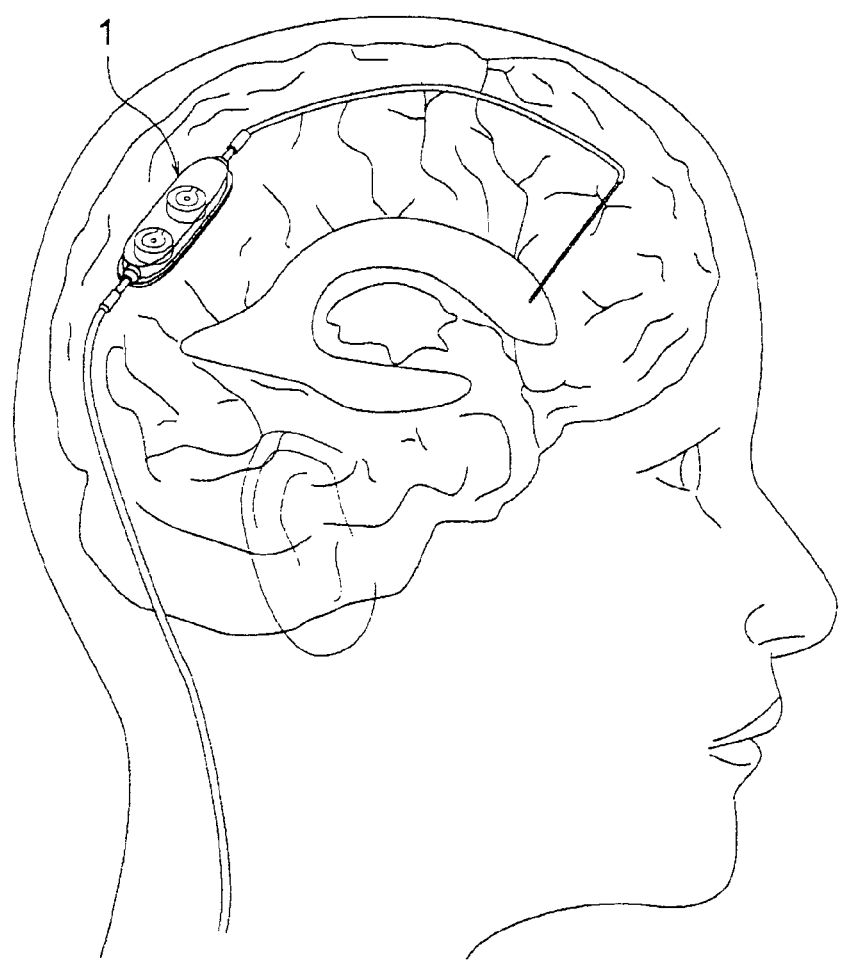
FIG. 7 is a view showing a transplanted state of the shunt valve for treatment of hydrocephalus as illustrated in FIG. 1.

FIG. 6 is an assembly perspective view of the second valve pressure variable device of the shunt valve for treatment of hydrocephalus as illustrated in FIG. 5.

In FIG. 1, a shunt valve for treatment of hydrocephalus 1 is formed as an integral unit and has a shunt main body 3 which is mounted to a cured plastic substrate 2, and a flexible silicone elastomer membrane 4 which covers the entire device. The silicone elastomer is a type of silicone that has a Si—O—Si combination in its molecules and when a curing catalyst such as peroxide or a platinum compound, etc. is added thereto, it cures like an elastomer or cures through partial crystallization.

The cured plastic substrate 2 is made of polypropylene (PP), for instance. Polypropylene (PP) is a thermoplastic resin very similar to high-density polyethylene, such as a polymeric compound (polymer) obtained through addition polymerization of propylene, and has a low specific gravity, superior thermal resistance, strongly acidic and alkaline properties, resistance to repeated bending and great tensile strength.

As shown in FIG. 2, the shunt main body 3 has an inflow connector 5 provided on the inflow side of the cerebrospinal fluid draining from the ventricles and an outflow connector 6 provided on the outflow side of the cerebrospinal fluid draining from the shunt main body 3 where it accumulated. The shunt main body 3 is entirely covered by a silicone elastomer membrane 4 and a lower end of the silicone elastomer membrane 4 is tightly attached to the cured plastic substrate 2.

The inflow connector 5 is formed in a cylindrical shape and is provided at the inflow side of the cerebrospinal fluid into the shunt main body 3, acting as a connector that connects the catheter implanted in the body. Specifically, the inflow connector 5 connects a rear end of the ventricular catheter having a needle provided at a leading end thereof for tapping into the ventricle and has a protrusion 5A which projects to the outside formed at a leading end thereof. This bulging portion 5A connects the rear end of the ventricular catheter to the inflow connector 5 and the ventricular catheter to the inflow connector 5, and after the connector of the ventricular catheter is attached by way of surgery, it prevents the ventricular catheter from easily disconnecting from the inflow connector 4.

The outflow connector 6 is formed in a cylindrical shape and is provided at the outflow side of the cerebrospinal fluid from inside the shunt main body 3 to the outside, acting as a connector that connects the peritoneal catheter implanted in the body. Specifically, the outflow connector 6 connects a rear end of the ventricular catheter having a leading end thereof inserted in the peritoneal cavity and has a protrusion 6A which projects to the outside formed at a leading end thereof.

A first valve pressure variable device 7 is provided at a downstream side of the inflow connector 5. A second valve pressure variable device 8 is provided on the outflow path side of the first valve pressure variable device 7 used for draining the cerebrospinal fluid and serves to accumulate the cerebrospinal fluid which drains from the first valve pressure variable device 7.

The outflow connector 6 is mounted at the outflow side of the second valve pressure variable device 8 where the cerebrospinal fluid is drained.

The first valve pressure variable device 7 has the configuration shown in FIGS. 3 and 4. The second valve pressure variable device 8 will be described later while referring to FIGS. 5 and 6.

In FIGS. 3 and 4, the first valve pressure variable device 7 consists of a first cover 9 and a first valve main body 10.

The first cover 9 is constituted of a round cover and has an opening 9A for allowing passage of the cerebrospinal fluid flowing in from the inflow connector 5 formed at a center thereof. Opening 9A constitutes an inlet port through which the cerebrospinal fluid flows inside and has a tapered shape, with a diameter thereof becoming larger starting from the outer wall surface of the first cover 9 towards the inner wall surface thereof. The outer surface side of the opening 9A in the first cover 9 which constitutes the inlet port acts as an occluder as will be described later.

Also, a female screw 9B is provided at an inner periphery of the side wall of the first cover 9. The female screw 9B of the first cover 9 is tightly screwed together with a male screw 14A provided at an outer periphery of a side wall of a case 14 in the first valve main body 10 so as to prevent any discharges of cerebrospinal fluid from places other than opening 9A into the first valve main body 10.

The first valve main body 10 has a ball 11, a rotor 12 with a built-in magnet, and a case 14 which houses the ball 11 and the rotor 12 and has a step-wise plate 13 formed in a bottom surface thereof. The first valve main body 10 screws together with and is sealed by the first cover 9.

The ball 11 which is stored inside the case 14 of the first valve main body 10 is made of a material which does not deform, wear away or deteriorate when soaked in the cerebrospinal fluid over a long period of time. For instance, ball 11 is made of a synthetic ruby. The reason why a synthetic ruby is used as the ball 11 is that it does not deform, wear away or deteriorate when soaked in the cerebrospinal fluid over a long period of time, and also, it can be easily seen from outside the shunt main body 3 which is entirely covered by a membrane 4 made of a semi-transparent silicone elastomer.

The ball 11 works as a valve which opens and closes the opening 9A formed in the first cover 9 from the inside and adjusts the flow rate of the cerebrospinal fluid in accordance with the depressing force of the ball 11 towards the opening 9A. Accordingly the flow rate of the cerebrospinal fluid passing through the opening 9A formed in the first cover 9 is controlled by the opening area determined by the clearance between the ball 11 and the inner wall surface of the opening 9A, specifically, the distance between the inner wall surface of the opening 9A and the outer surface of the ball which is closest to the inner wall surface of the opening 9A. The on-off valve is thus comprised of the opening 9A formed in the first cover 9 and the ball 11, while the clearance between the opening 9A formed in the first cover 9 and the ball 11 forms the aperture of the on-off valve.

The rotor 12 is formed in a disk shape and has a plurality of legs 12A projecting downwards which are mounted on a lower surface thereof and lower the skid resistance at the time rotor 12 rotates. Also, a powerful magnet is buried in one random location in the rotor 12, and after the shunt main body 3 is transplanted between the skull and the scalp, the magnet which is provided in the regulating device and has opposite magnetic polarity with the magnetic pole of the magnet buried in the rotor 12 attracts the magnet buried in the rotor 12 using the attractive force between the north pole or south pole of the magnet buried in the rotor 12 and their respective opposite magnetic poles (south pole or north pole) and the regulating device lifts the rotor 12 against the elastic force of the rotor spring 16 which pushes against the bottom surface of the case 14 by attracting the magnet buried in the rotor 12 from outside of the scalp. The rotor 12 is built so as to enable rotation thereof when the rotation device of the regulating device starts rotating after the rotor 12 has been lifted by the regulating device.

The powerful magnet which is buried in the rotor 12 does not necessarily have to be provided in one location alone, but can be provided in 2 or 3 locations.

A ball spring housing unit 12B which houses a ball spring 15 and a rotor spring housing unit 12C which houses a rotor spring 16 are provided on the upper surface of the rotor 12.

The ball spring 15 is mounted in the ball spring housing unit 12B and the rotor spring 16 is mounted in the rotor spring housing unit 12C, respectively. The ball spring 15 and the rotor spring 16 which are housed in the ball spring housing unit 12B and the rotor spring housing unit 12C are built so that the size of their respective diameters differs to avoid interference between each other.

The ball spring 15 may be comprised of a coiled spring or a spiral spring with increasingly smaller diameter starting from its rear end towards its leading end. The ball spring 15 supports the ball 11 at a leading end portion thereof with the smallest diameter and the ball 11 is depressed in the opening 9A of the first cover 9 by the elastic force of the spring. The rear end portion of the ball spring 15 with the largest diameter is housed in the ball spring housing unit 12B and the ball spring 15 is mounted on the upper surface of the rotor 12.

Similarly with the ball spring 15, the rotor spring 16 is comprised of a coiled spring, or a spiral spring with increasingly smaller diameter starting from its rear end towards its leading end. The rotor spring 16 is provided outside the ball spring 11 so as to avoid interference with the ball spring 11 when expanding and contracting, and is also provided on the upper surface of the rotor 12 so that the leading end portion thereof with the smallest diameter comes in contact with an abutting part 9C of the upper inner wall surface of the first cover 9 and the rear end portion thereof with the largest diameter is housed in the rotor spring housing unit 12C of the rotor 12.

The rotor spring 16 comes in contact with the abutting part 9C of the upper inner wall surface of the first cover 9 and depresses the rotor 12 to the plate 13 side of the case 14 through its elastic force.

Thus, the rotor 12, the plate 13, the case 14, the ball spring 15 and the rotor spring 16 make up a management system that manages opening and closing of the on-off valve comprised of the opening 9A of the first cover 9 and the ball 11.

The case 14 is comprised of a bottomed cylindrical body having a circular cross section and houses the first valve main body 10, specifically the ball 11 and the rotor 12 having a built-in magnet, having a step-wise plate 13 provided on a bottom surface thereof. A male screw 14 A is formed in an upper portion of the outer periphery of a side wall of the case 14 and tightly screws together with a female screw 9B formed in an inner periphery of the side wall of the first cover 9 so as to prevent the cerebrospinal fluid from discharging into the first valve main body 10 from locations other than the opening 9A.

The plate 13 is formed in a step-wise pattern having a plurality of steps (for instance, 5 steps; theoretically, any number of steps is possible, however, 5 is the optimum number of steps at which the regulating device rotates the rotor 12 using the magnet buried in the rotor 12), with each step having a different height. The steps of the plate 13 are formed so each step has a height that differs by a specific amount. The rotor 12 is mounted on the plate 13 and the legs 12A formed on the lower surface of the rotor 12 reduce the contact resistance, helping the rotor 12 rotate easily on the plate 13.

An uneven portion 13A is formed at the boundary of each step formed in the plate 13. Uneven portion 13A is a protrusion that protrudes on the upper surface side of the plate 13 and prevents the rotor 12 from returning to its original position on the plate 13 after having rotated and moved to a specific step position.

When the rotor 12 rotates on the plate 13 by a predetermined angle and moves upwards by one step starting at the lowermost step on the plate 13, the position of the upper surface of the rotor 12 moves upwards one step as the rotor 12 moves upwards by one step on the plate 13. Vice versa, when the rotor 12 rotates on the plate 13 by a predetermined angle and moves downwards by one step from the uppermost step on the plate 13, the position of the upper surface of the rotor 12 moves downwards by one step each time the rotor 12 moves downwards by one step on the plate 13.

When the rotor 12 moves upwards (or downwards) on the plate 13 by one step and the position of the upper surface of the rotor 12 moves upwards (or downwards) by one step, the rotor spring 16 mounted between the upper surface of the rotor 12 and the abutting part 9C of the upper inner wall surface of the first cover 9 is compressed (or expanded) by the surface of the steps on the plate 13.

When the height position of the upper surface of the rotor 12 moves upwards (or downwards) by one step, the ball spring 15 mounted between the upper surface of the rotor 12 and the abutting part 9C of the upper inner wall surface of the first cover 9 is also compressed (or expanded) and the depressing force acting on the ball 11 supported at the leading end portion of the ball spring 15 increases.

If there is no change in the pressure of the cerebrospinal fluid which flows from the ventricles through the inflow connector 5 and into the opening 9A formed in the first cover 9, the depressing force of the ball spring 15 acting on the ball 11 will remain unchanged.

When the intraventricular pressure becomes high, the pressure of the cerebrospinal fluid draining from the ventricles through the inflow connector 5 will increase. Thus, the ball 11 which is fitted in the opening 9A formed in the first cover 9 is held down under the pressure of the cerebrospinal fluid draining from the ventricles through the inflow connector 5, against the depressing force of the ball spring 15. As a result, the opening area between the opening 9A and the ball 11 increases, enabling passage of a large amount of cerebrospinal fluid. Intraventricular pressure is thus kept constant.

An outflow tract 14B for draining the cerebrospinal fluid which passes between the opening 9A and the ball 11 and flows into the first valve main body 10 to the outside of the first valve main body 10 is provided at a lower portion in an outer periphery of the side wall of case 14. A second valve pressure variable device 8 is provided on the outflow tract 14B side of the case 14.

In FIG. 4, 17 denotes a seal while 18 denotes a guide ring.

The second valve pressure variable device 8 has a similar configuration with that of the first valve pressure variable device 7, as illustrated in FIG. 5 and FIG. 6.

In FIG. 5 and FIG. 6, the second valve pressure variable device 8 is made of a second cover 20 and a second valve main body 21.

The second cover 20 consists of a round cover and has an opening 20A for allowing passage of the cerebrospinal fluid flowing in from the inflow connector 5 formed at a center thereof. The opening 20A constitutes an inlet port through which the cerebrospinal fluid flows inside and has a tapered shape, with a diameter thereof becoming larger starting from the outer wall surface of the second cover 20 towards the inner wall surface thereof. The outer surface side of the opening 20A in the second cover 20A which constitutes the inlet port acts as an occluder as will be described later.

Also, a female screw 20B is provided at an inner periphery of the side wall of the second cover 20. The female screw 20B of the second cover 20 is tightly screwed together with a male screw 25A provided at an outer periphery of a side wall of a case 25 in the second valve main body 21 so as to prevent any discharges of cerebrospinal fluid from places other than opening 20A into the second valve main body 21.

The second valve main body 21 has a ball 22, a rotor 23 with a built-in magnet, and a case 25 which houses the ball 22 and the rotor 23 and has a step-wise plate 24 formed in a bottom surface thereof. The second valve main body 21 screws together with and is sealed by the second cover 20.

The ball 22 which is stored inside the case 25 of the second valve main body 21 is made of a material which does not deform, wear away or deteriorate when soaked in the cerebrospinal fluid over a long period of time. For instance, the ball 22 is made of a synthetic ruby. The reason why a synthetic ruby is used as the ball 22 is that it does not deform, wear away or deteriorate when soaked in the cerebrospinal fluid over a long period of time, and also, it can be easily seen from outside the shunt main body 3 which is entirely covered by a membrane 4 made of a semi-transparent silicone elastomer.

The ball 22 works as a valve which opens and closes the opening 20A formed in the second cover 20 from the inside and adjusts the flow rate of the cerebrospinal fluid in accordance with the depressing force of the ball 22 towards the opening 20A. Accordingly the flow rate of the cerebrospinal fluid passing through the opening 20A formed in the second cover 20 is controlled by the opening area determined by the clearance between the ball 22 and the inner wall surface of the opening 20A, specifically, the distance between the inner wall surface of the opening 20A and the outer surface of the ball which is closest to the inner wall surface of the opening 20A. The on-off valve is thus comprised of the opening 20A formed in the second cover 20 and the ball 22, while the clearance between the opening 20A formed in the second cover 20 and the ball 22 forms the aperture of the on-off valve.

The rotor 23 is formed as a disk-shaped member and has a plurality of legs 23A projecting downwards which are mounted on a lower surface thereof and lower the skid resistance at the time rotor 23 rotates. Also, a powerful magnet is buried in one random location in the rotor 23, and after the shunt main body 3 is transplanted between the skull and the scalp, the magnet which is provided in the regulating device and has opposite magnetic polarity with the magnetic pole of the magnet buried in the rotor 23 attracts the magnet buried in the rotor 23 using the attractive force between the north pole and south pole of the magnet buried in the rotor 23 and their respective opposite magnetic poles (south pole or north pole) and the regulating device lifts the rotor 23 against the elastic force of a rotor spring 27 which pushes against the bottom surface of the case 25 by attracting the magnet buried in the rotor 23 from outside of the scalp. The rotor 23 is built so as to enable rotation thereof when the rotation device of the regulating device starts rotating after the rotor 23 has been lifted by the regulating device.

The powerful magnet which is buried in the rotor 23 does not necessarily have to be provided in one location alone, but can be provided in 2 or 3 locations.

A ball spring housing unit 23B which houses a ball spring 26 and a rotor spring housing unit 23C which houses a rotor spring 27 are provided on the upper surface of the rotor 23.

The ball spring 26 is mounted in the ball spring housing unit 23B and the rotor spring 27 is mounted in the rotor spring housing unit 23C. The ball spring 26 and the rotor spring 27 which are housed in the ball spring housing unit 23B and the rotor spring housing unit 23C, respectively are built so that the size of their respective diameters differs to avoid interference between each other.

The ball spring 26 may be comprised of a coiled spring or a spiral spring with increasingly smaller diameter starting from its rear end towards its leading end. The ball spring 26 supports the ball 22 at a leading end portion thereof with the smallest diameter and the ball 22 is depressed in the opening 20A of the second cover 20 by the elastic force of the spring. The rear end portion of the ball spring 26 with the largest diameter is housed in the ball spring housing unit 23B and the ball spring 26 is mounted on the upper surface of the rotor 23.

Similarly with the ball spring 26, the rotor spring 27 is comprised of a coiled spring, or a spiral spring with increasingly smaller diameter starting from its rear end towards its leading end. The rotor spring 27 is provided outside the ball spring 11 so as to avoid interference with the ball spring 11 when expanding and contracting, and is also provided on the upper surface of the rotor 23 so that the leading end portion thereof with the smallest diameter comes in contact with an abutting part 20C of the upper inner wall surface of the second cover 20 and the rear end portion thereof with the largest diameter is housed in the rotor spring housing unit 23C of the rotor 23.

The rotor spring 27 comes in contact with the abutting part 20C of the upper inner wall surface of the second cover 20 and depresses the rotor 23 to the plate 24 side of the case 25 through its elastic force.

Thus, the rotor 23, the plate 24, the case 25, the ball spring 26 and the rotor spring 27 make up a management system that manages opening and closing of the on-off valve comprised of the opening 20A of the second cover 20 and the ball 22.

The case 25 houses the second valve main body 21, specifically the ball 22 and the rotor 23 having a built-in magnet, and has a step-wise plate 24 provided on a bottom surface thereof. A male screw 25A is formed in an upper portion of the outer periphery of a side wall of the case 25 and tightly screws together with a female screw 20B formed in an inner periphery of the side wall of the second cover 20 so as to prevent the cerebrospinal fluid from discharging into the second valve main body 21 from locations other than the opening 20A.

The plate 24 is formed in a step-wise pattern having a plurality of steps (for instance, 5 steps; theoretically, any number of steps is possible, however, 5 is the optimum number of steps at which the regulating device rotates the rotor 23 using the magnet buried in the rotor 23), with each step having a different height. The steps of the plate 24 are formed so each step has a height that differs by a specific amount. The rotor 24 is mounted on the plate 24 and the legs 23A formed on the lower surface thereof reduce the contact resistance, helping the rotor rotate easily on the plate.

An uneven portion 24A is formed at the boundary of each step formed in the plate 24. The uneven portion 24A is a protruding portion that protrudes on the upper surface side of the plate 24 and prevents the rotor 23 from returning to its original position on the plate 24 after having rotated and moved to a specific step position.

When the rotor 23 rotates on the plate 24 by a predetermined angle and moves upwards by one step starting at the lowermost step on the plate 24, the position of the upper surface of the rotor 23 moves upwards one step as the rotor 23 moves upwards by one step on the plate 24. Vice versa, when the rotor 23 rotates on the plate 24 by a predetermined angle and moves downwards by one step from the uppermost step on the plate 24, the position of the upper surface of the rotor 23 moves downwards by one step each time the rotor 23 moves downwards by one step on the plate 24.

When the rotor 23 moves upwards (or downwards) on the plate 24 by one step and the position of the upper surface of the rotor 23 moves upwards (or downwards) by one step, the rotor spring 27 mounted between the upper surface of the rotor 23 and the abutting part 20C of the upper inner wall surface of the second cover 20 is compressed (or expanded) by the surface of the steps on the plate 24.

When the height position of the upper surface of the rotor 23 moves upwards (or downwards) by one step, the ball spring 26 mounted between the upper surface of the rotor 23 and the abutting part 20C of the upper inner wall surface of the second cover 20 is also compressed (or expanded) and the depressing force acting on the ball 22 supported at the leading end portion of the ball spring 26 increases.

If there is no change in the pressure of the cerebrospinal fluid which drains from the outflow tract 14B formed in a lower portion at an outer periphery of a side wall of the case 14 in the first valve pressure variable device 7, passing through the first valve pressure variable device 7 and into the opening 20A formed in the second cover 20, the depressing force of the ball spring 26 of the second valve pressure variable device 8 acting on the ball 22 will remain unchanged.

When the intraventricular pressure becomes high, the pressure of the cerebrospinal fluid draining from the ventricles through the inflow connector 5 and into the first valve pressure variable device 7 will rise. Thus, the ball 11 which is fitted in the opening 9A formed in the first cover 9 of the first valve pressure variable device 7 is held down under the pressure of the cerebrospinal fluid draining from the ventricles through the inflow connector 5, against the depressing force of the ball spring 15. As a result, the opening area between the opening 9A and the ball 11 becomes larger, enabling passage of a large amount of cerebrospinal fluid through the clearance between the opening 9A and the ball 11.

When the opening area between the opening 9A of the first valve pressure variable device 7 and the ball 11 becomes large enabling passage of a large amount of cerebrospinal fluid through the opening 9A and the ball 11, the pressure of the cerebrospinal fluid flowing out of the outflow tract 14B formed in the lower portion of the case 14 through the first valve pressure variable device 7 becomes high. Thus, the pressure of the cerebrospinal fluid flowing out of the outflow tract 14B formed in the lower portion of the case 14 through the first valve pressure variable device 7 and into the opening 20A formed in the second cover 20 of the second valve pressure variable device 8 becomes high.

When the pressure of the cerebrospinal fluid draining from the outflow tract 14B formed in a lower portion of the case 14 becomes high, the ball 22 which is fitted in the opening 20A formed in the second cover 20 of the second valve pressure variable device 8 is held down under the high pressure of the cerebrospinal fluid draining from the outflow tract 14B, against the depressing force of the ball spring 26. As a result, the opening area between the opening 20A and the ball 22 increases, allowing passage of a large amount of cerebrospinal fluid.

An outflow tract 14B for draining the cerebrospinal fluid which passes between the opening 20A and the ball 22 and flows into the second valve main body 21 to the outside of the second valve main body 21 is provided at a lower portion in an outer periphery of the side wall of the case 25. A second valve pressure variable device 8 is provided on the outflow tract 14B side of the case 25.

In FIG. 6, 28 denotes a seal while 29 denotes a guide ring.

The shunt valve 1 for treatment of hydrocephalus having the above-described configuration is implanted at a predetermined location in the brain. To implant the shunt valve 1 for treatment of hydrocephalus, a small incision is made in the skull through surgery, the membrane between the skull and the brain is opened, and the needle attached to the leading end of the ventricular catheter is inserted inside the lateral ventricle through the incision, while the rear end of the ventricular catheter is connected to the inflow connector 5. Then, the leading end of the peritoneal catheter is passed behind the ear, through the neck and under the chest skin, and is inserted in the peritoneal cavity through a small incision in the peritoneal membrane. The rear end of the peritoneal catheter whose leading end is inserted in the peritoneal cavity is connected to the outflow connector 6 of the shunt valve for treatment of hydrocephalus 1. Then, the shunt valve for treatment of hydrocephalus 1 is implanted at a predetermined location in the brain.

Next, the operation of the shunt valve for treatment of hydrocephalus 1 according to the first embodiment of the present invention and having the above-described configuration will be described.

The shunt valve for treatment of hydrocephalus 1 according to the first embodiment of the present invention has two valve pressure variable devices: the first valve pressure variable device 7 and the second valve pressure variable device 8. The first valve pressure variable device 7 and the second valve pressure variable device 8 are connected in series against the flow of the cerebrospinal fluid and together work as a fluid pressure regulating valve. Accordingly, adjustment of the intraventricular pressure upstream of the first valve pressure variable device 7 and the amount of the cerebrospinal fluid draining out of the ventricles is carried out by the two valve pressure variable devices: the first valve pressure variable device 7 and the second valve pressure variable device 8.

The intraventricular pressure upstream of the first valve pressure variable device 7 can be adjusted by rotating the rotor 12 to adjust the height position between the upper surface of the rotor 12 in the first valve pressure variable device 7 and the abutting part 9C of the upper inner wall surface of the first cover 9. Similarly, the amount of the cerebrospinal fluid which flows into the first valve pressure variable device 7 can be adjusted by rotating the rotor 12 to adjust the height position between the upper surface of the rotor 12 in the first valve pressure variable device 7 and the abutting part 9C of the upper inner wall surface of the first cover 9.

The pressure inflow side of the second valve pressure variable device 8 can be adjusted by rotating the rotor 23 to adjust the height position between the upper surface of the rotor 23 in the second valve pressure variable device 8 and the abutting part 20C of the upper inner wall surface of the second cover 20. Similarly, the amount of the cerebrospinal fluid which flows into the second valve pressure variable device 8 can be adjusted by rotating the rotor 23 to adjust the height position between the upper surface of the rotor 23 of the second valve pressure variable device 8 and the abutting part 20C of the upper inner wall surface of the second cover 20.

The relationship between the first valve pressure variable device 7 and the second valve pressure variable device 8 is as follows.

The intraventricular pressure upstream of the first valve pressure variable device 7 can be adjusted by rotating the rotor 12 to adjust the height position between the upper surface of the rotor 12 of the first valve pressure variable device 7 and the abutting part 9C of the upper inner wall surface of the first cover 9. Similarly, the amount of the cerebrospinal fluid which flows into the first valve pressure variable device 7 can be adjusted by rotating the rotor 12 to adjust the height position between the upper surface of the rotor 12 of the first valve pressure variable device 7 and the abutting part 9C of the upper inner wall surface of the first cover 9.

First, the two respective valve pressure variable devices of the shunt valve for treatment of hydrocephalus 1 to be implanted in the patient are set to the intraventricular pressure condition of that patient. These settings will stabilize the intraventricular pressure through the first valve pressure variable device 7 and the second valve pressure variable device 8.

In cases of changes in the intraventricular pressure after the shunt valve for treatment of hydrocephalus 1 has been transplanted into a patient, the first valve pressure variable device 7 and the second valve pressure variable device 8 are adjusted to adjust the intraventricular pressure and the flow rate from the brain ventricles. In this case, the setting values of the first valve pressure variable device 7 and the second valve pressure variable device 8 at the time of the transplant will become the standard values.

Now, let us consider the case that the amount of intraventricular cerebrospinal fluid increases leading to an increase in the intraventricular pressure. To lower the intraventricular pressure, the rotor 12 of the first valve pressure variable device 7 is rotated to increase the distance between the upper surface of the rotor 12 and the abutting part 9C of the upper inner wall surface of the first cover 9 and the upper surface position of the rotor 12 is moved downwards by one step, for instance. As a result, the depressing force of the ball spring 15 which presses up the ball 11 drops, and the flow rate of the cerebrospinal fluid flowing from the ventricles through the inflow connector 5 into the first valve pressure variable device 7 increases. The intraventricular pressure drops with the increase in the flow rate of the cerebrospinal fluid. If no changes are made to the settings of the rotor 23 of the second valve pressure variable device 8, the opening area between the opening 20A of the second cover 20 of the second valve pressure variable device 8 and the ball 22 will remain unchanged, and only the flow rate per unit area will increase.

If any complications occur with the patient when the rotor 12 of the first valve pressure variable device 7 is adjusted and the intraventricular pressure drops, there are cases where in order to prevent such complications associated with a drop in the intraventricular pressure, the rotor 12 of the first valve pressure variable device 7 is not adjusted (the adjustment position of the rotor 12 of the first valve pressure variable device 7 is returned to the original position). However, if the rotor 12 of the first valve pressure variable device 7 is not adjusted and the intraventricular pressure does not fall, the complications in the patient will not be solved.

On the one hand, there are cases where even if the rotor 12 of the first valve pressure variable device 7 is not adjusted and intraventricular pressure does not drop, a patient's symptoms improve by increasing the flow rate of the cerebrospinal fluid draining from the ventricles. In such a case, the rotor 23 of the second valve pressure variable device 8 is rotated without changing the position of the rotor 12 of the first valve pressure variable device 7, and the distance between the upper surface of the rotor 23 and the abutting part 20C of the upper inner wall surface of the second cover 20 is increased and the upper position of the rotor 23 is decreased by one step, for instance.

Thus, the depressing force of the ball spring 26 which presses up the ball 22 of the second valve pressure variable device 8 decreases, and the flow rate of the cerebrospinal fluid flowing from the outflow tract 14B of the case 25 of the first valve pressure variable device 7 into the second valve pressure variable device 8 increases. As the flow rate of the cerebrospinal fluid increases, the flow rate, per unit area, of the cerebrospinal fluid flowing through the second valve pressure variable device 8 increases, and the flow rate of the cerebrospinal fluid flowing through the first valve pressure variable device 7 increases. The flow rate of the cerebrospinal fluid flowing from the ventricle through the inflow connector 5 and into the first valve pressure variable device 7 increases as the flow rate of the cerebrospinal fluid flowing through the first valve pressure variable device 7 increases.

The increase amount in the flow rate of the cerebrospinal fluid flowing from the ventricles through the inflow connector 5 and into the first valve pressure variable device 7 works to slowly lower the intraventricular pressure, even if no adjustment is made to the rotor 12 of the first valve pressure variable device 7 and a drop in the intraventricular pressure is not obtained.

With such adjustments, according to the shunt valve for treatment of hydrocephalus according to the first embodiment of the present invention, if the amount of intraventricular cerebrospinal fluid becomes high leading to an increase in the intraventricular pressure, the flow rate of the cerebrospinal fluid flowing from the ventricles through the inflow connector 5 and into the first valve pressure variable device 7 can be increased by valve adjustment in the second valve pressure variable device 8, without performing any valve adjustments in the first valve pressure variable device 7 and making any changes to the cerebrospinal fluid pressure.

Now, let us consider the case that the amount of intraventricular cerebrospinal fluid decreases leading to a decrease in the intraventricular pressure. To raise the intraventricular pressure, the rotor 12 of the first valve pressure variable device 7 is rotated to decrease the distance between the upper surface of the rotor 12 and the abutting part 9C of the upper inner wall surface of the first cover 9 and the upper surface position of the rotor 12 is moved upwards by one step, for instance. As a result, the depressing force of the ball spring 15 which presses up the ball 11 increases, and the flow rate of the cerebrospinal fluid flowing from the ventricles through the inflow connector 5 into the first valve pressure variable device 7 decreases. The intraventricular pressure increases with the decrease in the flow rate of the cerebrospinal fluid. If no changes are made to the settings of the rotor 23 of the second valve pressure variable device 8, the opening area between the opening 20A of the second cover 20 in the second valve pressure variable device 8 and the ball 22 will remain unchanged, and only the flow rate per unit area will decrease.

If any complications occur with the patient when the rotor 12 of the first valve pressure variable device 7 is adjusted and the intraventricular pressure rises, there are cases where in order to remove such complications associated with a rise in the intraventricular pressure, the rotor 12 of the first valve pressure variable device 7 is not adjusted (the adjustment position of the rotor 12 of the first valve pressure variable device 7 is returned to the original position). However, if the rotor 12 of the first valve pressure variable device is not adjusted and intraventricular pressure does not rise, the complications in the patient will not be solved.

On the one hand, there are cases where even if the rotor 12 of the first valve pressure variable device 7 is not adjusted and intraventricular pressure does not rise, a patient's symptoms improve by the decrease in the flow rate of the cerebrospinal fluid draining from the ventricles. In such a case, the rotor 23 of the second valve pressure variable device 8 is rotated without changing the position of the rotor 12 of the first valve pressure variable device 7, and the distance between the upper surface of the rotor 23 and the abutting part 20C of the upper inner wall surface of the second cover 20 is decreased and the upper surface position of the rotor 23 is moved upwards by one step, for instance. Thus, the depressing force of the ball spring 26 which presses up the ball 22 of the second valve pressure variable device 8 increases, and the flow rate of the cerebrospinal fluid flowing from the outflow tract 14B of the case 25 of the first valve pressure variable device 7 into the second valve pressure variable device 8 decreases. As the flow rate of the cerebrospinal fluid decreases, the flow rate, per unit area, of the cerebrospinal fluid flowing through the second valve pressure variable device 8 decreases, and the flow rate of the cerebrospinal fluid flowing through the first valve pressure variable device 7 drops. The flow rate of the cerebrospinal fluid flowing from the ventricles through the inflow connector 5 and into the first valve pressure variable device 7 decreases as the flow rate of the cerebrospinal fluid flowing through the first valve pressure variable device 7 decreases.

The decrease amount in the flow rate of the cerebrospinal fluid flowing from the ventricles through the inflow connector 5 and into the first valve pressure variable device 7 works to slowly raise the intraventricular pressure, even if no adjustment is made to the rotor 12 of the first valve pressure variable device 7 and a rise in intraventricular pressure is not obtained.

With such adjustments, according to the shunt valve for treatment of hydrocephalus according to the first embodiment of the present invention, if the amount of intraventricular cerebrospinal fluid becomes low leading to a drop in the intraventricular pressure, the flow rate of the cerebrospinal fluid flowing from the ventricles through the inflow connector 5 and into the first valve pressure variable device 7 can be decreased by valve adjustment in the second valve pressure variable device 8, without performing any valve adjustments in the first valve pressure variable device 7 and making any changes to the cerebrospinal fluid pressure.

Furthermore, if the amount of the intraventricular cerebrospinal fluid becomes high (or low) and the intraventricular pressure becomes high (or low), there are cases where in order to decrease (or increase) the intraventricular pressure, the rotor 12 of the first valve pressure variable device 7 needs to be rotated to increase (or decrease) the distance between the upper surface of the rotor 12 and the abutting part 9C of the upper inner wall surface of the first cover 9 and move the upper surface position of the rotor 12 downwards (or upwards) by 2 steps, for instance.

In such a case, the rotor 12 of the first valve pressure variable device 7 is rotated to increase (or decrease) the distance between the upper surface of the rotor 12 and the abutting part 9C of the upper inner wall surface of the first cover 9 and move the upper surface position of the rotor 12 downwards (or upwards) by one step, for instance, and the rotor 23 of the second valve pressure variable device 8 is rotated to increase (or decrease) the distance between the upper surface of the rotor 23 and the abutting part 20C of the upper inner wall surface of the second cover 20 and move the upper surface position of the rotor 23 downwards (or upwards) by one step, for instance, without causing a sudden rise (or drop) in the intraventricular pressure.

The relationship between the intraventricular pressure and the flow rate of the cerebrospinal fluid draining from the ventricles as obtained by adjusting the first valve pressure variable device 7 and the second valve pressure variable device 8 in the shunt valve for treatment of hydrocephalus 1 according to the first embodiment of the present invention is as follows.

Specifically, in the case valve adjustment is carried out in the first valve pressure variable device 7 and the second valve pressure variable device 8, the intraventricular pressure in the shunt valve for treatment of hydrocephalus 1 is set based on the higher adjustment pressure between the adjustment pressure obtained by valve adjustment in the first valve pressure variable device 7 and the adjustment pressure obtained by valve adjustment in the second valve pressure variable device 8, and the flow rate of the cerebrospinal fluid draining from the ventricles at this time is equal to the sum of the flow rate of the cerebrospinal fluid following valve adjustment in the first valve pressure variable device 7 and the flow rate of the cerebrospinal fluid following valve adjustment in the second valve pressure variable device 8. The flow rate of this cerebrospinal fluid is based on the pressure of the cerebrospinal fluid following valve adjustment in the first valve pressure variable device 7 and pressure adjustment of the cerebrospinal fluid obtained by valve adjustment in the second valve pressure variable device 8 and are apparent in the variations in the flow rate of the cerebrospinal fluid in the first valve pressure variable device 7 and the flow rate of the cerebrospinal fluid in the second valve pressure variable device 8.

Thus, use of the shunt valve for treatment of hydrocephalus 1 makes it possible to slowly lower (or raise) the intraventricular pressure and increase (or decrease) the flow rate of the cerebrospinal fluid per unit area and adjustment can be carried in accordance with the condition of the patient who received the implant of the shunt valve for treatment of hydrocephalus 1.

According to the shunt valve for treatment of hydrocephalus according to the first embodiment of the present invention, valve adjustment of the first valve pressure variable device 7 and valve adjustment of the second valve pressure variable device 8 can be carried out independently from each other, which means that in comparison with the conventional shunt valve for treatment of hydrocephalus which could be adjusted in 5 ways, the shunt valve of the present invention can be adjusted in 25 ways, enabling very fine settings with respect to hydrocephalus patients.

Second Embodiment

Figure 8:
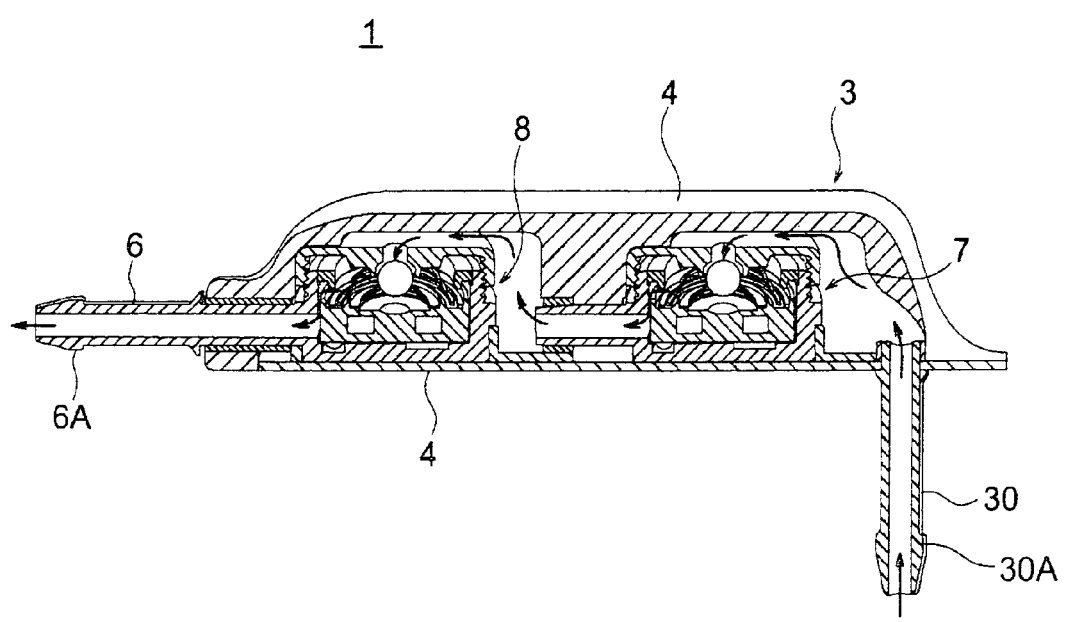
FIG. 8 is a vertical cross-sectional view of a shunt valve for treatment of hydrocephalus showing a second embodiment of a shunt valve for treatment of hydrocephalus according to the present invention.

FIG. 8 shows a second embodiment of a shunt valve for treatment of hydrocephalus according to the present invention.

In FIG. 8, a shunt valve for treatment of hydrocephalus 1 is formed as an integral unit and has a shunt main body 3 which is attached to a cured plastic substrate 2, and a flexible silicone elastomer membrane 4 which covers the entire device.

The second embodiment of the shunt valve for treatment of hydrocephalus according to the present invention as illustrated in FIG. 8 differs from the first embodiment of the shunt valve for treatment of hydrocephalus according to the invention illustrated in FIG. 1 in that in the first embodiment illustrated in FIG. 1, the inflow connector 5 is provided in the shunt main body 3 which is covered by the silicone elastomer membrane 4 in its entirety, in a longitudinal direction of the cured plastic substrate 2 in the shunt for treatment of hydrocephalus 1, whereas in the second embodiment illustrated in FIG. 8, an inflow connector 30 is provided so as to penetrate the cured plastic substrate 2 of the shunt valve for treatment of hydrocephalus 1 from the shunt main body 3 which is covered by the silicone elastomer membrane 4 in its entirety.

There are no other differences with the first embodiment of the shunt valve for treatment of hydrocephalus 1 according to the invention as illustrated in FIG. 1.

In FIG. 8, 30A denotes a protrusion which is formed in a leading end portion of the inflow connector 30 and projects to the outside, and connects the rear end of the ventricular catheter having a needle which taps into the ventricles attached to a leading end thereof.

Figure 9:
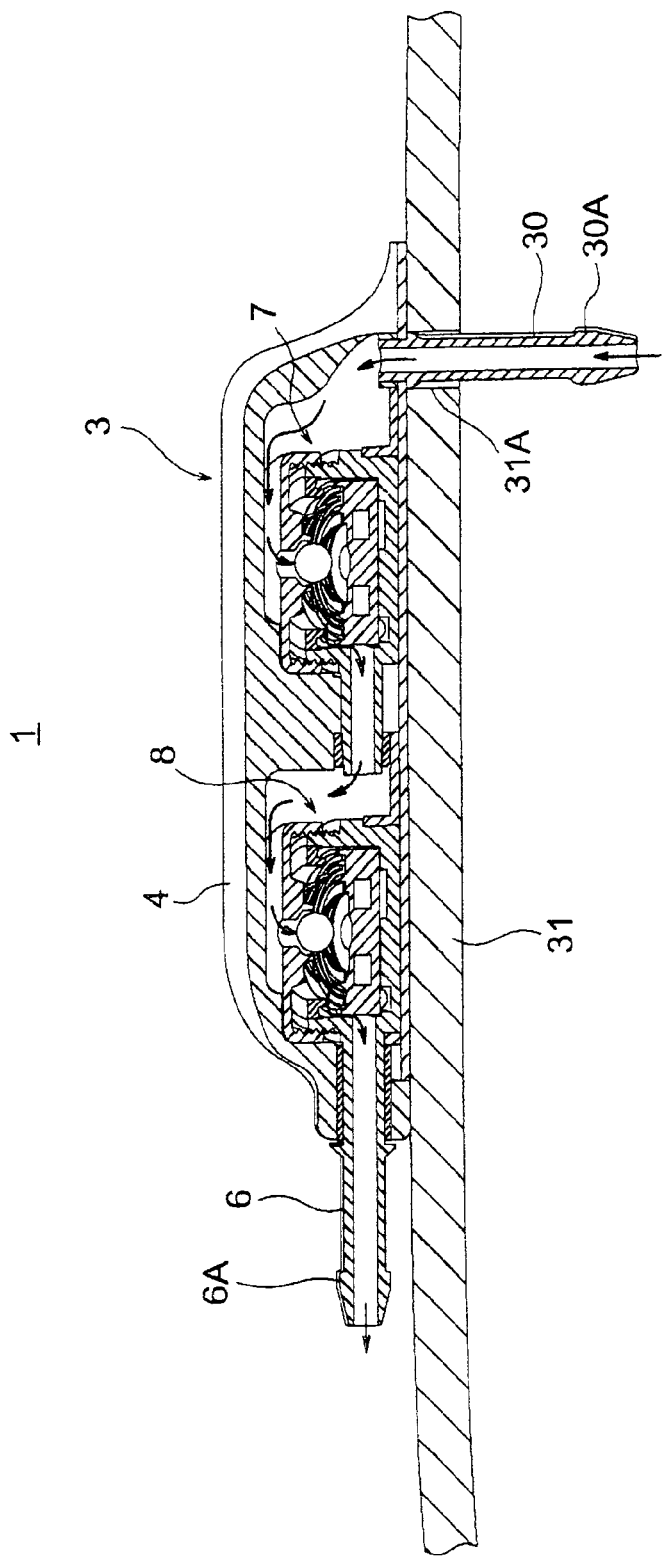
FIG. 9 is a cross-sectional view showing a transplanted state of the shunt valve for treatment of hydrocephalus as illustrated in FIG. 8.

In the shunt valve for treatment of hydrocephalus 1 according to the invention illustrated in FIG. 8 with the above-mentioned configuration, the inflow connector 30 is provided so as to penetrate from the cured plastic substrate 2 downwards, and is mounted as shown in FIG. 9.

Specifically, a small incision 31A is made in the skull 31 through surgery, the membrane between the skull 31 and the brain is opened, and the needle attached to the leading end of the ventricular catheter is inserted inside the lateral ventricle through the incision 31A, and the rear end of the ventricular catheter is connected to the inflow connector 30. Then, the inflow connector 30 projecting downwards of the cured plastic substrate 2 is inserted into the incision 31A made in the skull 31 and is implanted between the scalp and the skull 31.

Accordingly, the shunt valve for treatment of hydrocephalus 1 according to the invention as illustrated in FIG. 8 can help stabilize the shunt valve for treatment of hydrocephalus 1 which was implanted between the scalp and the skull 31.

Third Embodiment

Figure 10:
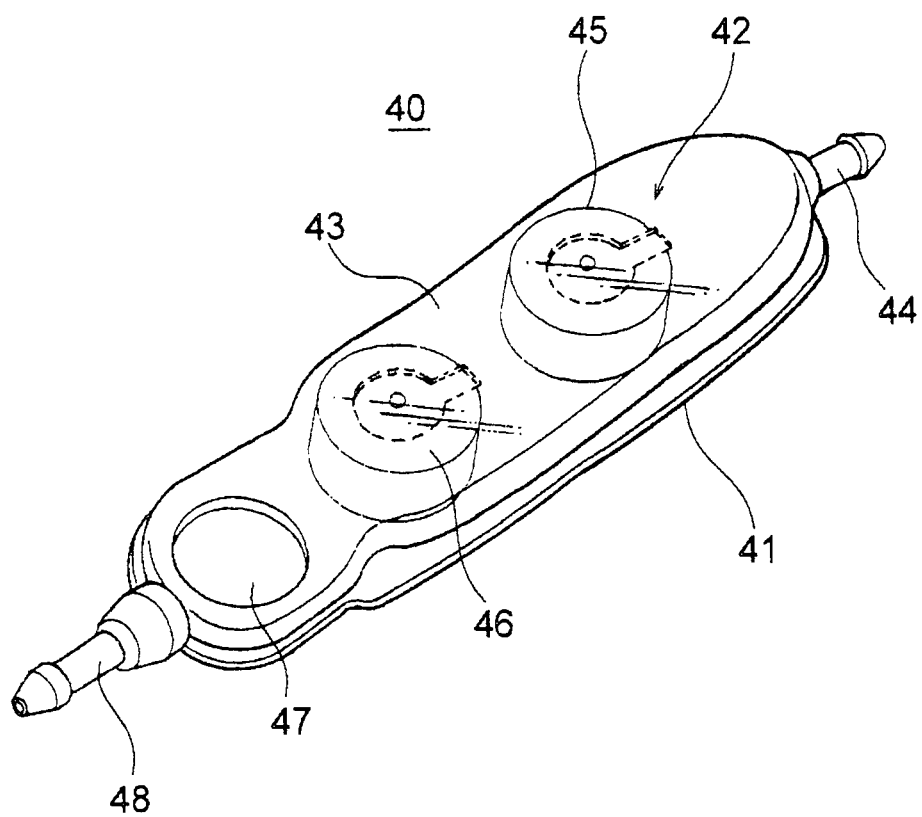
FIG. 10 is an overall perspective view of a shunt valve for treatment of hydrocephalus showing a third embodiment of a shunt valve for treatment of hydrocephalus according to the present invention.
Figure 11:
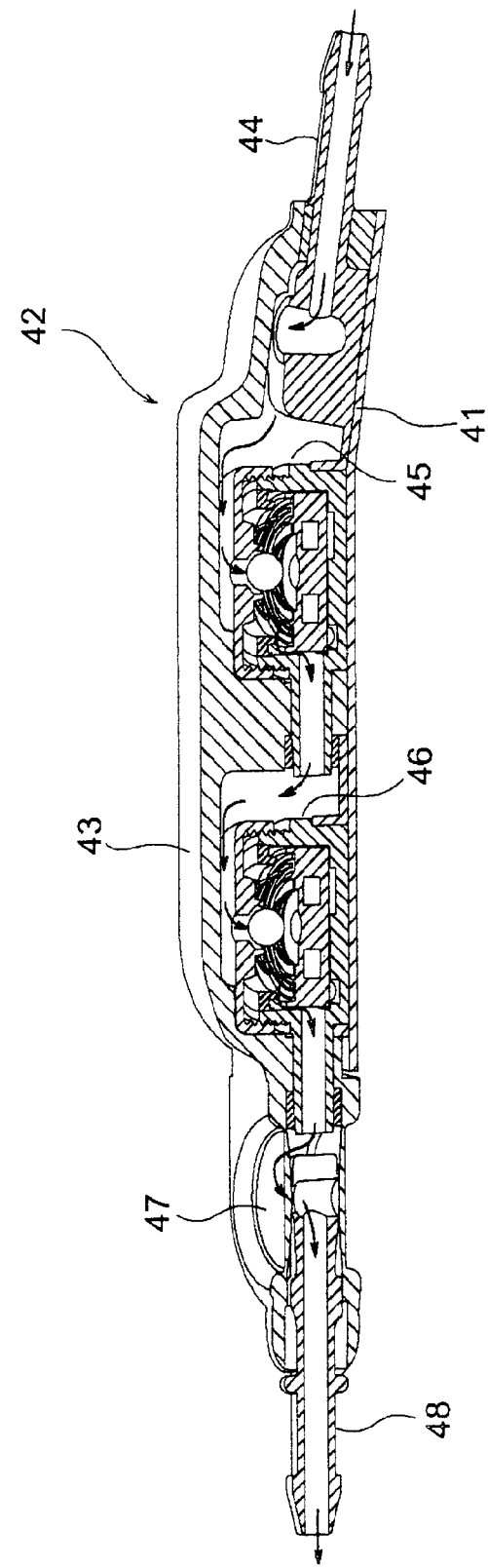
FIG. 11 is a vertical cross-sectional view of the shunt valve for treatment of hydrocephalus as illustrated in FIG. 10.

A third embodiment of a shunt valve for treatment of hydrocephalus according to the present invention is shown in FIG. 10 and FIG. 11.

In FIG. 10, a shunt valve for treatment of hydrocephalus 40 is formed as an integral unit and has a shunt main body 42 which is mounted on a cured plastic substrate 41, and a flexible silicone elastomer membrane 43 which covers the entire device.

The shunt main body 42 which is covered by the silicone elastomer membrane 43 in its entirety has an inflow connector 44 provided on the inflow side of the cerebrospinal fluid. The shunt main body 42 is provided with a first valve pressure variable device 45 and a second valve pressure variable device 46.

A chamber 47 is provided on the cerebrospinal fluid outflow side of a second valve pressure variable device 46, and an outflow connector 48 is attached to the outflow side of the cerebrospinal fluid from the chamber 47.

A ventricle catheter is connected to the inflow connector 44 and a peritoneal catheter is connected to an outflow connector 48.

The inflow connector 44 has a similar configuration with the inflow connector 5 illustrated in FIG. 2 and the outflow connector 48 has a similar configuration with the outflow connector 6 as illustrated in FIG. 2.

The first valve pressure variable device 45 has a similar configuration with the first valve pressure variable device 7 as illustrated in FIG. 3 and FIG. 4. The second valve pressure variable device 46 has a similar configuration with the second valve pressure variable device 8 as illustrated in FIG. 3 and FIG. 4.

Chamber 47 prevents sudden outflow of the intraventricular cerebrospinal fluid and a sudden drop in the intraventricular pressure when a patient suddenly sits up from a lying down position. The chamber 47 has a check valve which opens in the event of a positive pressure created when the cerebrospinal fluid is forced to flow due to high intraventricular pressure, and closes when a negative pressure is created inside the peritoneal catheter to nullify the siphon effect of the cerebrospinal fluid. Chamber 47 has a cavity where the cerebrospinal fluid which normally drains out of the ventricles primarily accumulates when the valve closes due to the negative pressure.

The third embodiment of the shunt valve for treatment of hydrocephalus according to the present invention as illustrated in FIG. 10 and FIG. 11 differs from the first embodiment of the shunt valve for treatment of hydrocephalus according to the present invention as illustrated in FIG. 1 and FIG. 2 in that the first embodiment of the shunt valve for treatment of hydrocephalus according to the present invention as illustrated in FIG. 1 and FIG. 2 is provided with an outflow connector 6 on the output side of the second valve pressure variable device 8 where the cerebrospinal fluid is discharged, whereas in the third embodiment of the shunt valve of the hydrocephalus according to the present invention as illustrated in FIG. 10 and FIG. 11, a chamber 47 is provided on the output side of the second valve pressure variable device 46 where the cerebrospinal fluid is discharged and an outflow connector 48 is provided on the output side of the chamber 47 where the cerebrospinal fluid is discharged.

According to the third embodiment of the shunt valve for treatment of hydrocephalus according to the present invention and having the configuration as illustrated in FIG. 10 and FIG. 11, in addition to the operation of the first embodiment of the shunt valve for treatment of hydrocephalus according to the present invention as illustrated in FIG. 1 and FIG. 2, the occurrence of various other symptoms such as sharp headaches, sudden impaired awareness can be prevented. These symptoms occur when the patient suddenly sits up from a posture wherein intraventricular pressure is kept constant by the shunt valve for treatment of hydrocephalus and the amount of intraventricular cerebrospinal fluid decreases, leading to a sudden drop in the intraventricular pressure, which in turn causes the ventricles to become smaller and narrower, a condition known as the slit ventricle syndrome.

Fourth Embodiment

Figure 12:
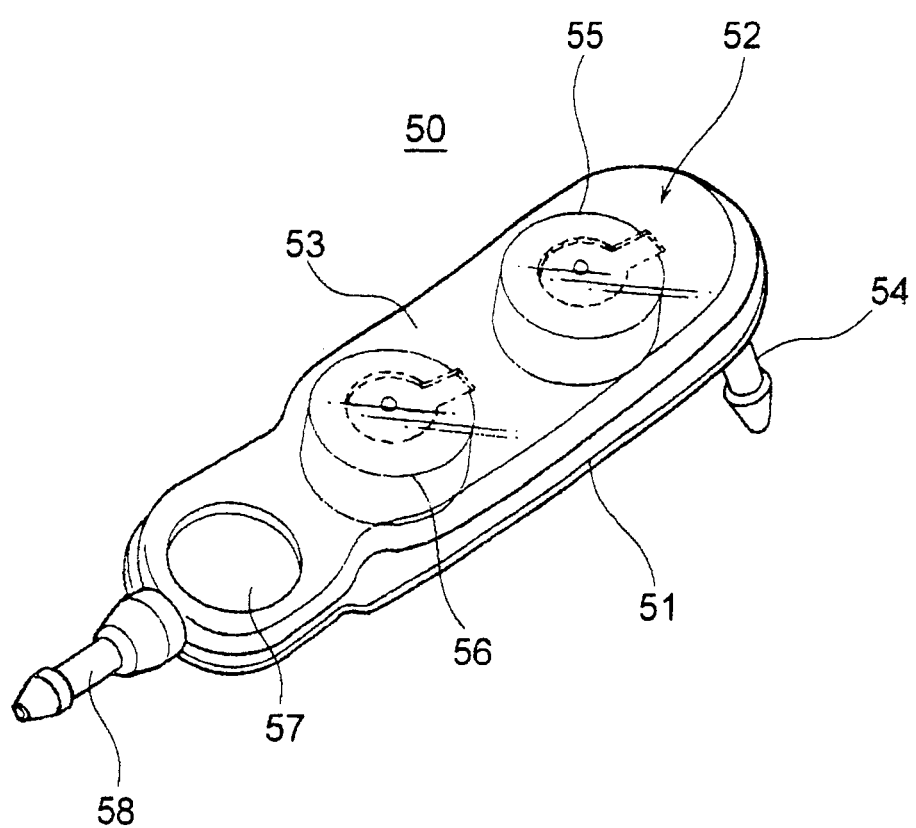
FIG. 12 is an overall perspective view of a shunt valve for treatment of hydrocephalus showing a fourth embodiment of a shunt valve for treatment of hydrocephalus according to the present invention.
Figure 13:
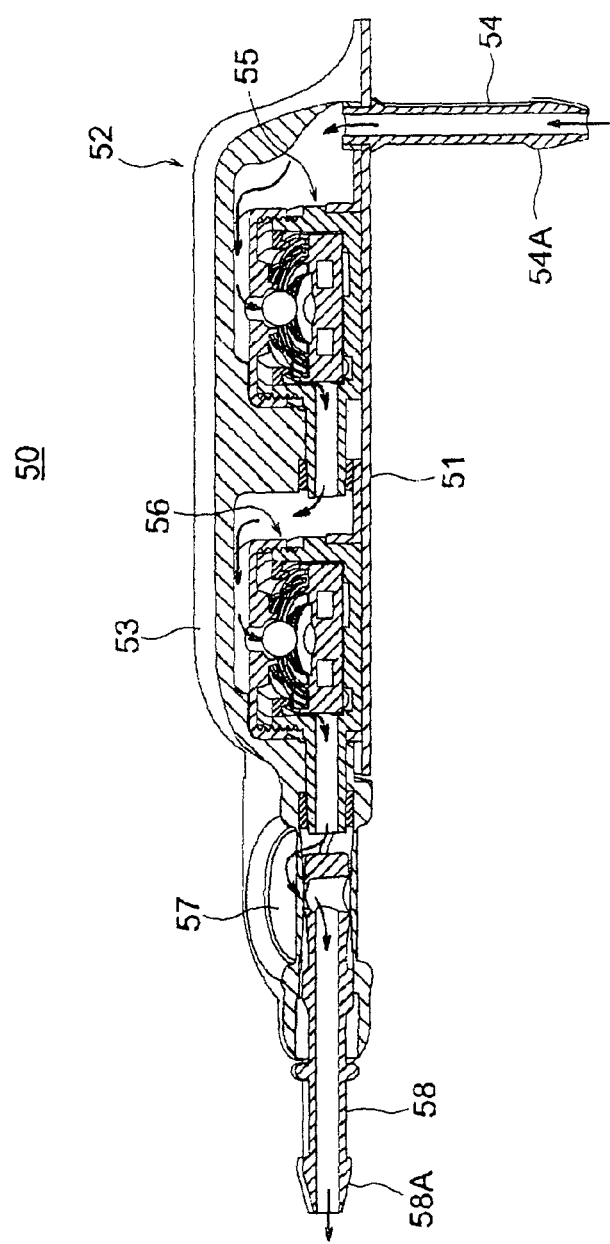
FIG. 13 is a vertical cross-sectional view of the shunt valve for treatment of hydrocephalus as illustrated in FIG. 12.

A fourth embodiment of a shunt valve for treatment of hydrocephalus according to the present invention is illustrated in FIG. 12 and FIG. 13.

In FIG. 12 and FIG. 13, a shunt valve for treatment of hydrocephalus 50 is formed as an integral unit and has a shunt main body 52 which is mounted on a cured plastic substrate 51, and a flexible silicone elastomer membrane 53 which covers the entire device.

The fourth embodiment of the shunt valve for treatment of hydrocephalus according to the present invention as illustrated in FIG. 12 and FIG. 13 differs from the third embodiment of the shunt valve for treatment of hydrocephalus according to the present invention as illustrated in FIG. 10 and FIG. 11 in that in the third embodiment as illustrated in FIG. 10 and FIG. 11, the inflow connector 44 is provided in the shunt main body 42 which is covered by the silicone elastomer membrane 43 in its entirety, in a longitudinal direction of the cured plastic substrate 41 in the shunt valve for treatment of hydrocephalus 40, whereas in the fourth embodiment illustrated in FIG. 12 and FIG. 13, an inflow connector 54 is provided so as to penetrate the cured plastic substrate 51 of the shunt valve for treatment of hydrocephalus 50 from the shunt main body 52 which is covered by the silicone elastomer membrane 53 in its entirety.

There are no other differences with the third embodiment of the shunt valve for treatment of hydrocephalus according to the invention as illustrated in FIG. 10 and FIG. 11.

In FIG. 8, 54A denotes a protrusion which is formed in a leading end portion of the inflow connector 54 and projecting to the outside and connects the rear end of the ventricular catheter having a needle which taps into the ventricles attached to a leading end thereof. 58A denotes a protrusion formed in a leading end portion of the outflow connector 58 and projecting to the outside and connects the rear end of the peritoneal catheter which is inserted in the peritoneal cavity.

The shunt main body 52 which is covered by the silicone elastomer membrane 53 in its entirety has a first valve pressure variable device 55, a second valve pressure variable device 56 and a chamber 57.

Chamber 57 is provided on the cerebrospinal fluid outflow side of the second valve pressure variable device 56 and an outflow connector 58 is provided on the cerebrospinal fluid outflow side of the chamber 57. A ventricular catheter is connected to the inflow connector 54 and a peritoneal catheter is connected to the outflow connector 58.

The inflow connector 54 has a similar configuration with the inflow connector 30 illustrated in FIG. 8 and the outflow connector 58 has a similar configuration with the outflow connector 6 as illustrated in FIG. 2.

Also, the first valve pressure variable device 55 has a similar configuration with the first valve pressure variable device 7 as illustrated in FIG. 3 and FIG. 4, and the second valve pressure variable device 56 has a similar configuration with the second valve pressure variable device 8 as illustrated in FIG. 3 and FIG. 4.

Chamber 57 has a similar configuration with chamber 47 as illustrated in FIG. 10 and FIG. 11.

Thus, the fourth embodiment of the shunt valve for treatment of hydrocephalus according to the present invention as illustrated in FIG. 12 and FIG. 13, has both the operation of the second embodiment of the shunt valve for treatment of hydrocephalus according to the present invention as illustrated in FIG. 8 and the operation of the third embodiment of the shunt valve for treatment of hydrocephalus according to the present invention as illustrated in FIG. 10 and FIG. 11.

Fifth Embodiment

Figure 14:
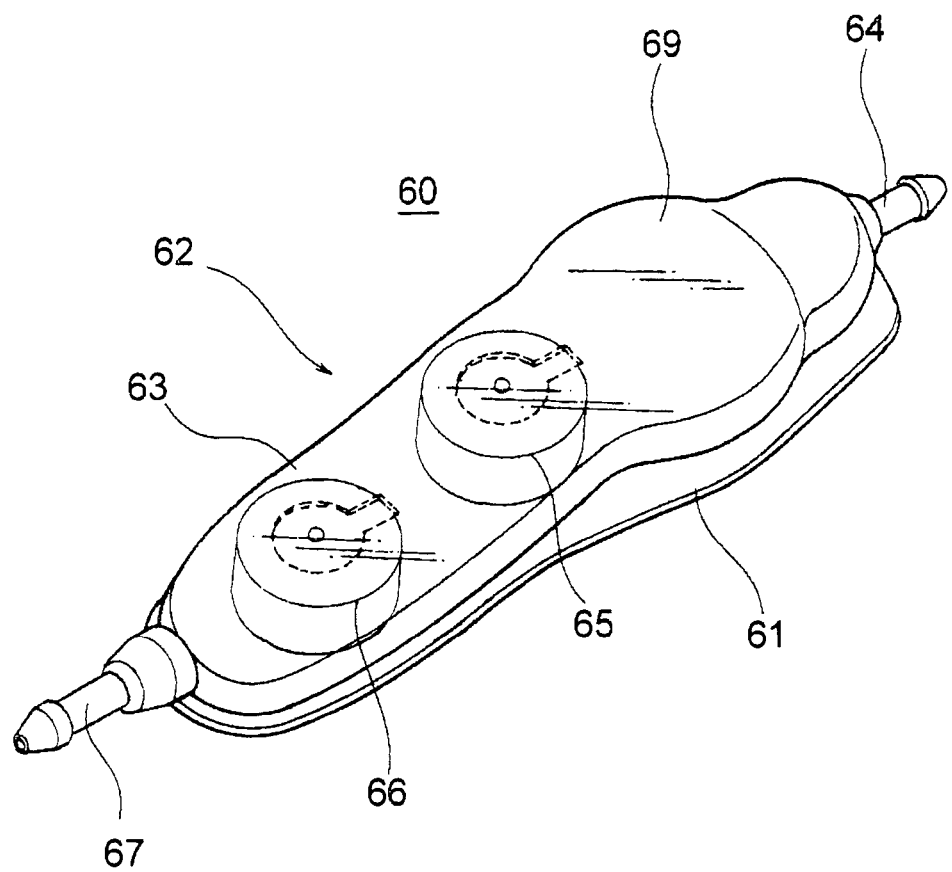
FIG. 14 is an overall perspective view of a shunt valve for treatment of hydrocephalus showing a fifth embodiment of a shunt valve for treatment of hydrocephalus according to the present invention.
Figure 15:
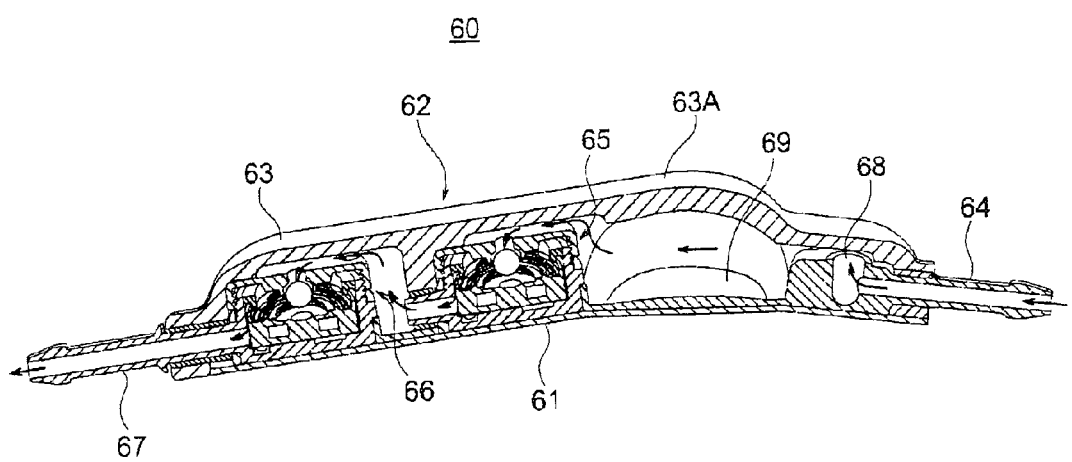
FIG. 15 is a vertical cross-sectional view of the shunt valve for treatment of hydrocephalus as illustrated in FIG. 14.

A fifth embodiment of a shunt valve for treatment of hydrocephalus according to the present invention is illustrated in FIG. 14 and FIG. 15.

In FIG. 14 and FIG. 15, a shunt valve for treatment of hydrocephalus 60 is formed as an integral unit and has a shunt main body 62 which is attached to a cured plastic substrate 61, and a flexible silicone elastomer membrane 63 which covers the entire device.

The fifth embodiment of the shunt valve for treatment of hydrocephalus according to the present invention as illustrated in FIG. 14 and FIG. 15 differs with the first embodiment of the shunt valve for treatment of hydrocephalus according to the present invention as illustrated in FIG. 1 in that in the first embodiment as illustrated in FIG. 1, the inflow connector 5 is provided at an inflow side of the cerebrospinal fluid into the first valve pressure variable device 7 of the shunt main body 3 which is covered by the silicone elastomer membrane 4 in its entirety, whereas in the fifth embodiment of the shunt valve for treatment of hydrocephalus according to the present invention as illustrated in FIG. 14 and FIG. 15, a ventricle-side occluder 68 and a reservoir 69 are provided between the inflow connector 64 and the shunt main body 62 which is covered by the silicone elastomer membrane 63 of the inflow connector 64 in its entirety.

There are no other differences with the third embodiment of the shunt valve for treatment of hydrocephalus according to the invention as illustrated in FIG. 10 and FIG. 11.

In FIG. 14 and FIG. 15, 64A denotes a protrusion formed at the leading end portion of the inflow connector 54 and projecting to the outside and connects a rear end of the ventricular catheter having a needle which taps into the ventricle attached at a leading end thereof 67A denotes a protrusion formed in a leading end portion of the outflow connector 67 and projecting to the outside and connects the rear end of the peritoneal catheter which is inserted into the peritoneal cavity.

A first valve pressure variable device 65, a second valve pressure variable device 66, a ventricle-side occluder 68 and a reservoir 69 are provided in the shunt main body 62 which is covered by a silicone elastomer membrane 63 in its entirety.

A reservoir 69 is provided at a cerebrospinal fluid inflow side of the first valve pressure variable device 65, and an inflow connector 64 is provided on the inflow side of the cerebrospinal fluid flowing from the reservoir 69 through the ventricle-side occluder 68. A ventricular catheter is connected to this inflow connector 54 and a peritoneal catheter is connected to the outflow connector 67.

The inflow connector 64 has a similar configuration with the inflow connector 30 as illustrated in FIG. 8 and the outflow connector 67 has a similar configuration with the outflow connector 6 as illustrated in FIG. 2.

The first valve pressure variable device 65 has a similar configuration with the first valve pressure variable device 7 as illustrated in FIG. 3 and FIG. 4, and the second valve pressure variable device 66 has a similar configuration with the second valve pressure variable device 8 as illustrated in FIG. 3 and FIG. 4.

The ventricle-side occluder 68 is provided on the outflow side of the intraventricular cerebrospinal fluid from the shunt main body 62 and works to press-close the tract through which the cerebrospinal fluid flows, temporarily shutting off the cerebrospinal fluid flow. The ventricle-side occluder 68 is formed in an opening portion at a rear end of the inflow connector 64, and is formed integral with membrane 63 comprised of a flexible silicone elastomer (soft silicone resin), having a cylindrical shape with an open top and a bottom.

Reservoir 69 is a chamber (open space) where a specific amount of cerebrospinal fluid flowing out from the needle connected to the leading end (ventricle end) of the catheter, from the ventricles through the inflow connector 64 accumulates. Specifically, reservoir 69 is a chamber (open space) formed between the opening side of the ventricle-side occluder 68 and the first valve pressure variable device 65 wherein a specific amount of the cerebrospinal fluid accumulates. The upper wall of the reservoir 69 is constituted of a silicone dome 63A formed by a membrane 63 raised in a dome shape and made of a flexible silicone elastomer (soft silicone resin) and when the silicone dome 63A is depressed, it the cerebrospinal fluid is forced to the outside of the reservoir 69.

Following implantation of the shunt valve 60 for treatment of hydrocephalus under the scalp and in the vicinity of the pericranium, the reservoir 69 makes it possible to harvest the cerebrospinal fluid accumulated therein and inject drug solutions such as contrast material and the like therein through a needle which is tapped from outside of the scalp into the membrane 63 forming the silicone dome 63A.

Once the shunt valve for treatment of hydrocephalus 60 is implanted underneath the scalp and in the vicinity of the pericranium, the position of the silicone done 63A cannot be confirmed visually from outside of the scalp. However, as the membrane 63 made of a silicone elastomer (soft silicone resin) has flexible properties, it can be examined with the fingers from above the scalp to confirm its position and a needle can easily be tapped from outside of the scalp into the membrane 63 which forms the silicone dome 63A.

An opening 9A of the first cover 9 in the first valve pressure variable device 65 is formed in the reservoir 69 for allowing inflow of the cerebrospinal fluid.

Thus, the fifth embodiment of the shunt valve for treatment of hydrocephalus according to the present invention as illustrated in FIG. 14 and FIG. 15 has the operation of the first embodiment of the shunt valve for treatment of hydrocephalus according to the present invention as illustrated in FIG. 1, and in addition, following implantation of the shunt valve for treatment of hydrocephalus 60 under the scalp and in the vicinity of the pericranium, it makes it possible to tap a needle from outside of the scalp into the membrane 63 forming the silicone dome 63A and harvest the cerebrospinal fluid accumulated therein or inject drug solutions such as contrast material and the like therein.

In case a clog occurs in the first valve pressure variable device 65 or in the second valve pressure variable device 66 following implant of the shunt valve for treatment of hydrocephalus underneath the scalp and in the vicinity of the pericranium, such a clog can be removed by depressing the membrane 63 from outside of the scalp to block the upper opening portion of the ventricle-side occluder 68 and depressing the silicone dome 63A from the outside the scalp to pump the fluid out.

Sixth Embodiment

Figure 16:
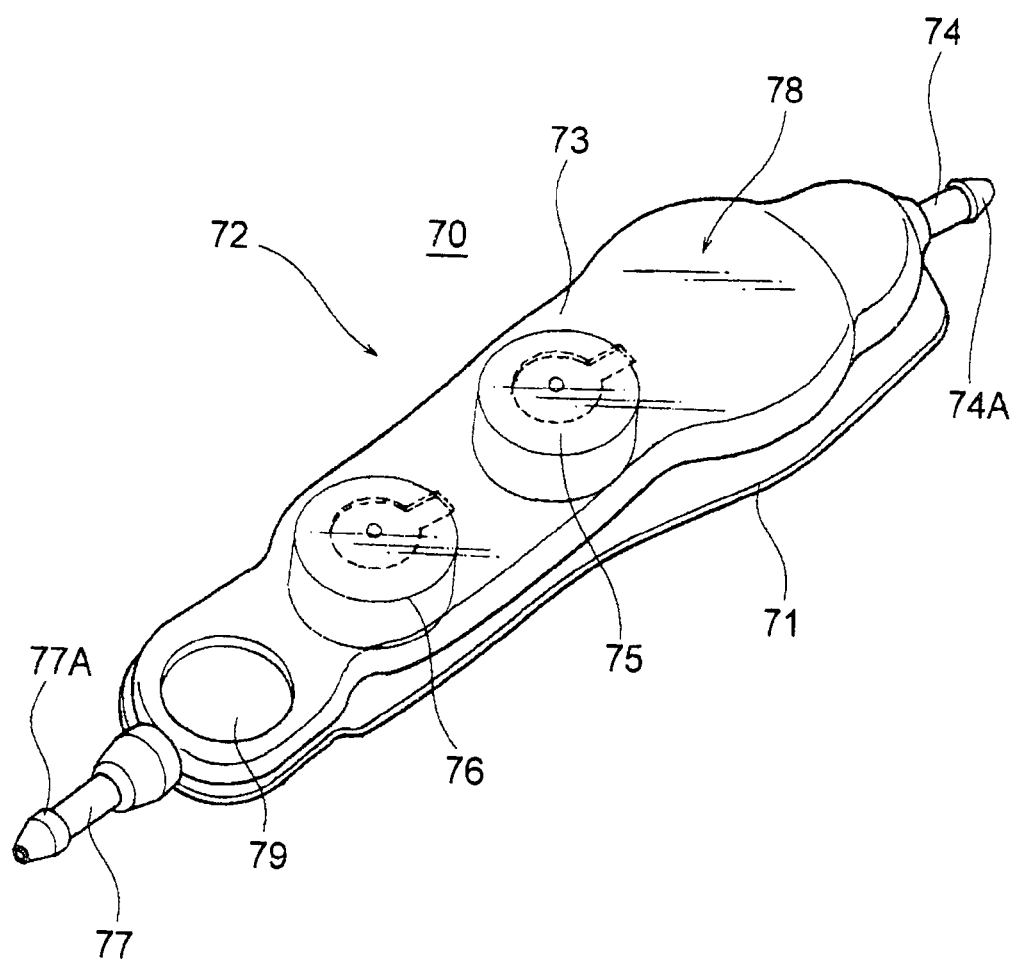
FIG. 16 is an overall perspective view of a shunt valve for treatment of hydrocephalus showing a sixth embodiment of a shunt valve for treatment of hydrocephalus according to the present invention.
Figure 17:
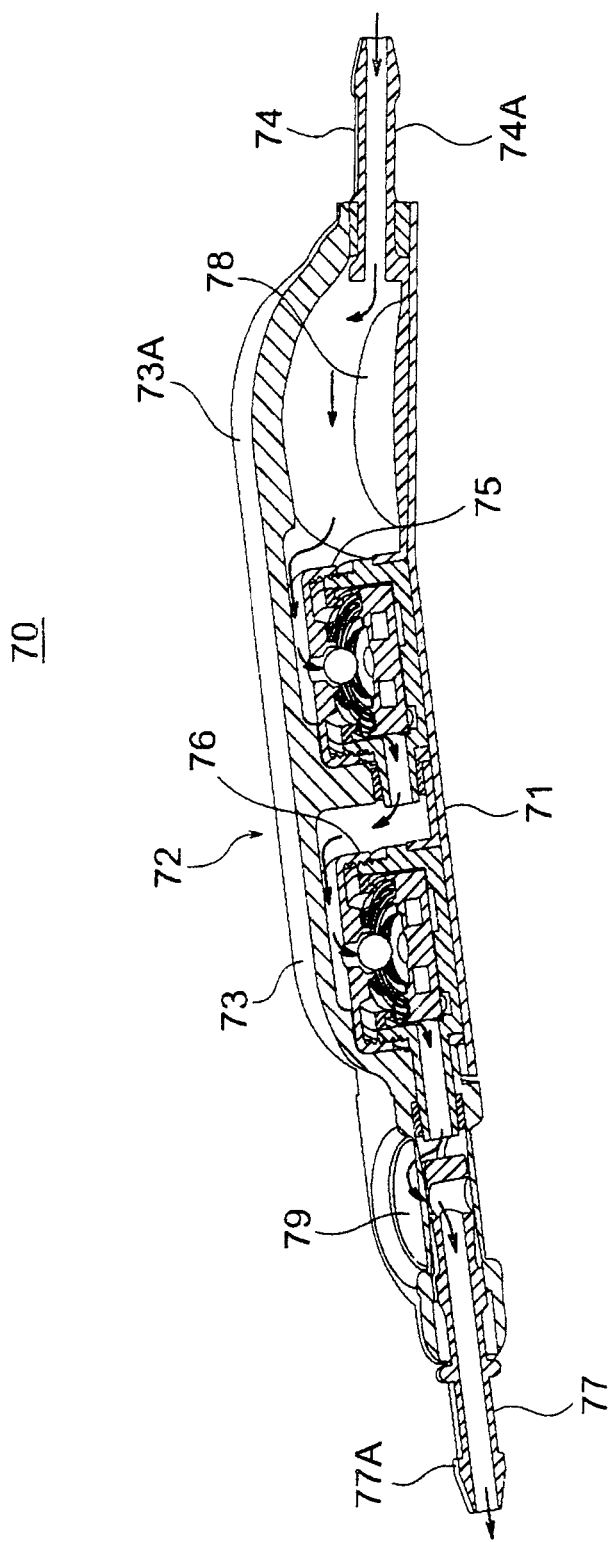
FIG. 17 is a vertical cross-sectional view of the shunt valve for treatment of hydrocephalus as illustrated in FIG. 16.

A sixth embodiment of a shunt valve for treatment of hydrocephalus according to the present invention is illustrated in FIG. 16 and FIG. 17.

In FIG. 16 and FIG. 17, a shunt valve 70 for treatment of hydrocephalus is formed as an integral unit and has a shunt main body 62 which is attached to a cured plastic substrate 71, and a flexible silicone elastomer membrane 73 which covers the entire device.

The sixth embodiment of the shunt valve for treatment of hydrocephalus according to the present invention as illustrated in FIG. 16 and FIG. 17 differs from the fifth embodiment of the shunt valve for treatment of hydrocephalus according to the present invention as illustrated in FIG. 14 and FIG. 15 in that in the fifth embodiment as illustrated in FIG. 14 and FIG. 15, a reservoir 69 is provided on the cerebrospinal fluid inflow side of the first valve pressure variable device 65 and a ventricle-side occluder 68 is provided in an opening portion for guiding the cerebrospinal fluid formed at a rear end of the inflow connector 64 through which the intraventricular cerebrospinal fluid flows into the reservoir 69, whereas in the sixth embodiment of the shunt valve for treatment of hydrocephalus according to the present invention as illustrated in FIG. 16 and FIG. 17, a reservoir 78 is provided on the cerebrospinal fluid inflow side of the first valve pressure variable device 75, an inflow connector 74 is provided through which the intraventricular cerebrospinal fluid flows into the reservoir 78 and which has an opening formed in the rear end thereof for guiding the cerebrospinal fluid and which allows to directly look inside the reservoir 78, and also, a chamber 79 is provided between the cerebrospinal fluid inflow side of the first valve pressure variable device 75 and the outflow connector 77 through which the cerebrospinal fluid drains into the peritoneal catheter.

There are no other differences with the fifth embodiment of the shunt valve for treatment of hydrocephalus according to the invention as illustrated in FIG. 14 and FIG. 15.

In FIG. 16 and FIG. 17, 74A denotes a protrusion formed in a leading end portion of the inflow connector 74 and projecting to the outside, which serves to connect the rear end of the ventricular catheter having a needle which taps into the ventricle attached to a leading end thereof 77A denotes a protrusion formed in a leading end portion of the outflow connector 77 and projecting to the outside, which serves to connect the rear end of the peritoneal catheter which is inserted into the peritoneal cavity.

In FIG. 16 and FIG. 17, 71 denotes a cured plastic substrate having a similar configuration with the cured plastic substrate 61 of the fifth embodiment as illustrated in FIG. 14 and FIG. 15. In FIG. 16 and FIG. 17, 72 denotes a shunt main body which has a similar configuration with the shunt main body 62 of the fifth embodiment as illustrated in FIG. 14 and FIG. 15. In FIG. 16 and FIG. 17, 73 denotes a flexible silicone elastomer membrane having a similar configuration with the flexible silicone elastomer membrane 63 as illustrated in FIG. 14 and FIG. 15 which covers the shunt main body 72 in its entirety and is formed as an integral unit therewith.

In FIG. 16 and FIG. 17, 75 denotes a first valve pressure variable device, 76 denotes a second valve pressure variable device, 78 denotes a reservoir and 79 denotes a chamber.

The reservoir 78 is provided on the cerebrospinal fluid inflow side of the first valve pressure variable device 75, and an inflow connector 74 is mounted to an inflow side thereof where the cerebrospinal fluid flows in from the reservoir 78. A ventricular catheter is connected to this inflow connector 74 and a peritoneal catheter is connected to an outflow connector 77.

The inflow connector 74 has a similar configuration with the inflow connector 64 of the fifth embodiment as illustrated in FIG. 14 and FIG. 15. The outflow connector 77 has a similar configuration with the outflow connector 68 of the fifth embodiment as illustrated in FIG. 14 and FIG. 15.

Also, the first valve pressure variable device 75 has a similar configuration with the first valve pressure variable device 65 of the fifth embodiment as illustrated in FIG. 14 and FIG. 15, while the second valve pressure variable device 76 has a similar configuration with the second valve pressure variable device 66 of the fifth embodiment as illustrated in FIG. 14 and FIG. 15.

Reservoir 78 is a chamber (open space) where a specific amount of cerebrospinal fluid which flows out from the needle connected to the leading end (ventricle end) of the catheter, from the ventricles through the inflow connector 74 accumulates. Specifically, reservoir 78 is a chamber (open space) formed between the opening side of the ventricle-side occluder 68 and the first valve pressure variable device 65 wherein a specific amount of the cerebrospinal fluid is accumulated. The upper wall of the reservoir 78 is constituted of a silicone dome 73A formed by a membrane 73 raised in a dome shape and made of a flexible silicone elastomer (soft silicone resin) and when the silicone dome 63A is depressed, the fluid is forced to the outside of the reservoir 69.

Following implantation of the shunt valve for treatment of hydrocephalus 70 under the scalp and in the vicinity of the pericranium, the reservoir 78 makes it possible to harvest the cerebrospinal fluid accumulated therein and inject drug solutions such as contrast material and the like therein through a needle which is tapped from outside of the scalp into the membrane 73 forming the silicone dome 73A.

Reservoir 78 has a similar configuration with reservoir 69 of the fifth embodiment as illustrated in FIG. 14 and FIG. 15, while chamber 79 has a similar configuration with chamber 47 of the third embodiment as illustrated in FIG. 10 and FIG. 11.

Accordingly, the sixth embodiment of the shunt valve for treatment of hydrocephalus according to the present invention as illustrated in FIG. 16 and FIG. 17 has the operation of the third embodiment of the shunt valve for treatment of hydrocephalus according to the present invention as illustrated in FIG. 10 and FIG. 11, and in addition, following implantation of the shunt valve for treatment of hydrocephalus 60 under the scalp and in the vicinity of the pericranium, it makes it possible to tap a needle from outside of the scalp into the membrane 63 forming the silicone dome 63A and harvest the cerebrospinal fluid accumulated therein or inject drug solutions such as contrast material and the like therein.

Seventh Embodiment

Figure 18:
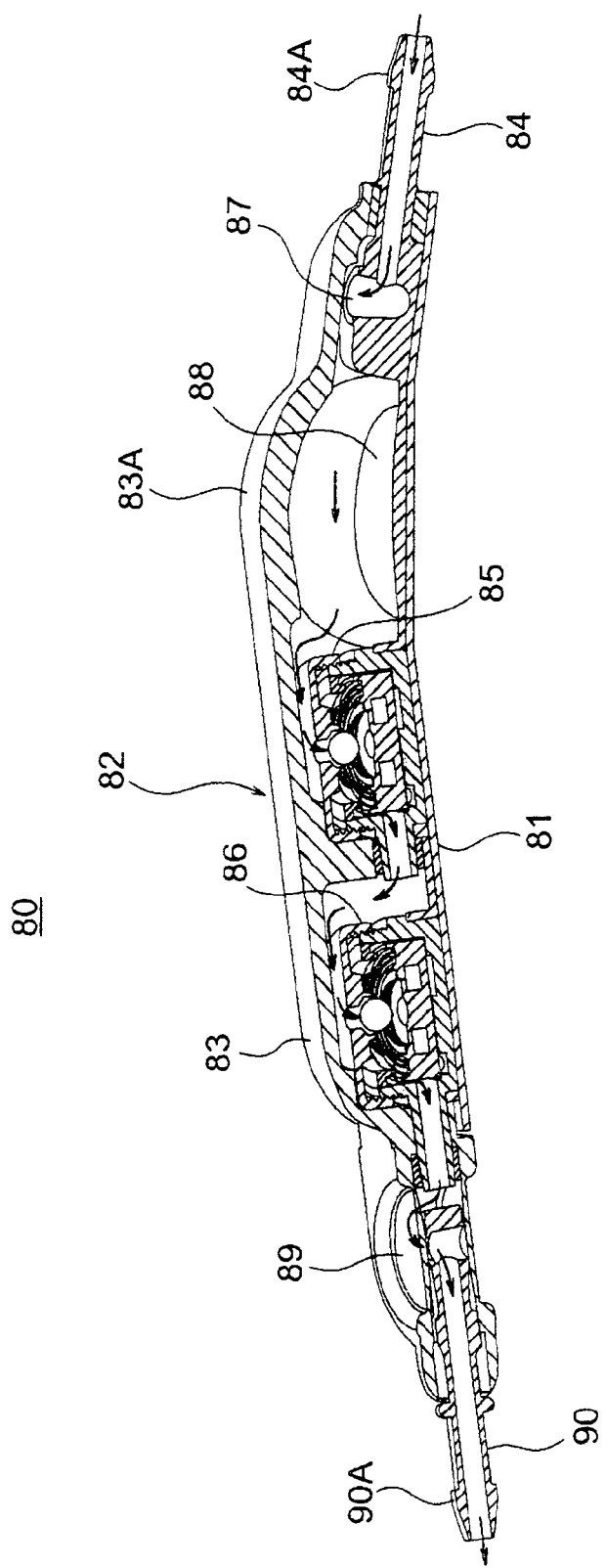
FIG. 18 is a cross-sectional view of a shunt valve for treatment of hydrocephalus showing a seventh embodiment of a shunt valve for treatment of hydrocephalus according to the present invention.

FIG. 18 shows a seventh embodiment of a shunt valve for treatment of hydrocephalus according to the present invention.

In FIG. 18, a shunt valve for treatment of hydrocephalus 80 is formed as an integral unit and has a shunt main body 82 which is attached to a cured plastic substrate 81, and a flexible silicone elastomer membrane 83 which covers the entire device.

The seventh embodiment of a shunt valve for treatment of hydrocephalus according to the present invention as illustrated in FIG. 18 differs from the sixth embodiment of the shunt valve for treatment of hydrocephalus according to the present invention as illustrated in FIG. 16 and FIG. 17 in that in the sixth embodiment of the shunt valve for treatment of hydrocephalus according to the present invention as illustrated in FIG. 16 and FIG. 17, a reservoir 78 is provided on the cerebrospinal fluid inflow side of the first valve pressure variable device 75 and an opening portion for guiding the cerebrospinal fluid is formed at a rear end of the inflow connector 74 through which the intraventricular cerebrospinal fluid flows into the reservoir 78 and allows to directly look inside the reservoir 78, whereas in the seventh embodiment of the shunt valve for treatment of hydrocephalus according to the present invention as illustrated in FIG. 18, a ventricle-side occluder 87 is formed in a rear end portion of the inflow connector 84, having a cylindrical shape with an open top and a bottom and serves to temporarily press-close the tract through which the cerebrospinal fluid draining from the ventricles flows.

There are no other differences with the sixth embodiment of the shunt valve for treatment of hydrocephalus according to the invention as illustrated in FIG. 16 and FIG. 17.

In FIG. 18, 84 denotes an inflow connector connecting a rear end of the ventricular catheter having a needle which taps into the ventricle mounted to a leading end thereof, while 84A denotes a protrusion formed in a leading end portion of the inflow connector 84 and projecting to the outside. In FIG. 18, 90 denotes an outflow connector connecting a rear end of the peritoneal catheter which is inserted into the peritoneal cavity, whereas 90A denotes a protrusion formed in a leading end portion of the outflow connector 90 and projecting to the outside.

In FIG. 18, 85 denotes a first valve pressure variable device, 86 denotes a second valve pressure variable device, 87 denotes a ventricular occluder, 88 denotes a reservoir and 89 denotes a chamber.

Reservoir 88 is provided on the cerebrospinal fluid inflow side of the first valve pressure variable device 85, and inflow connector 84 is mounted on the inflow side of the cerebrospinal fluid from the reservoir 88. A ventricular catheter is connected to the inflow connector 84 and a peritoneal catheter is connected to the outflow connector 90.

Inflow connector 84 has a similar configuration with the inflow connector 74 of the sixth embodiment as illustrated in FIG. 16 and FIG. 17, and outflow connector 90 has a similar configuration with the outflow connector 77 of the sixth embodiment as illustrated in FIG. 16 and FIG. 17.

The first valve pressure variable device 85 has a similar configuration with the first valve pressure variable device 75 of the sixth embodiment as illustrated in FIG. 16 and FIG. 17, and the second valve pressure variable device 86 has a similar configuration with the second valve pressure variable device 76 of the sixth embodiment as illustrated in FIG. 16 and FIG. 17.

Reservoir 88 is a chamber (open space) where a specific amount of cerebrospinal fluid flowing out from the needle connected to the leading end (ventricle end) of the catheter, from the ventricles through the inflow connector 84 accumulates. Specifically, reservoir 88 is a chamber (open space) formed between the opening side of the ventricle-side occluder 87 and the first valve pressure variable device 85 wherein a specific amount of the cerebrospinal fluid accumulates. The upper wall of the reservoir 88 is constituted of a silicone dome 83A formed by a membrane 73 raised in a dome shape and made of a flexible silicone elastomer (soft silicone resin) and when the silicone dome 83A is depressed, the fluid is forced to the outside of the reservoir 88.

Following implantation of the shunt valve 80 for treatment of hydrocephalus under the scalp and in the vicinity of the pericranium, the reservoir 88 makes it possible to harvest the cerebrospinal fluid accumulated therein and inject drug solutions such as contrast material and the like therein through a needle which is tapped from outside of the scalp into the membrane 83 forming the silicone dome 83A.

Reservoir 88 has a similar configuration with the reservoir 78 of the sixth embodiment as illustrated in FIG. 16 and FIG. 17, and chamber 79 has a similar configuration with the chamber 79 of the sixth embodiment as illustrated in FIG. 16 and FIG. 17.

Accordingly, the seventh embodiment of the shunt valve for treatment of hydrocephalus according to the present invention as illustrated in FIG. 18 has the operation of the sixth embodiment of the shunt valve for treatment of hydrocephalus according to the present invention as illustrated in FIG. 16 and FIG. 17, and in addition, clogs which occur in the first valve pressure variable device 85 and the second valve pressure variable device 86 following implantation of the shunt valve for treatment of hydrocephalus 80 under the scalp and in the vicinity of the pericranium can be removed, by depressing the membrane 83 from outside of the skull to block the upper opening of the ventricle-side occluder 87, and depressing the silicone dome 83A from outside of the skull to pump the fluid out.

Eighth Embodiment

Figure 19:
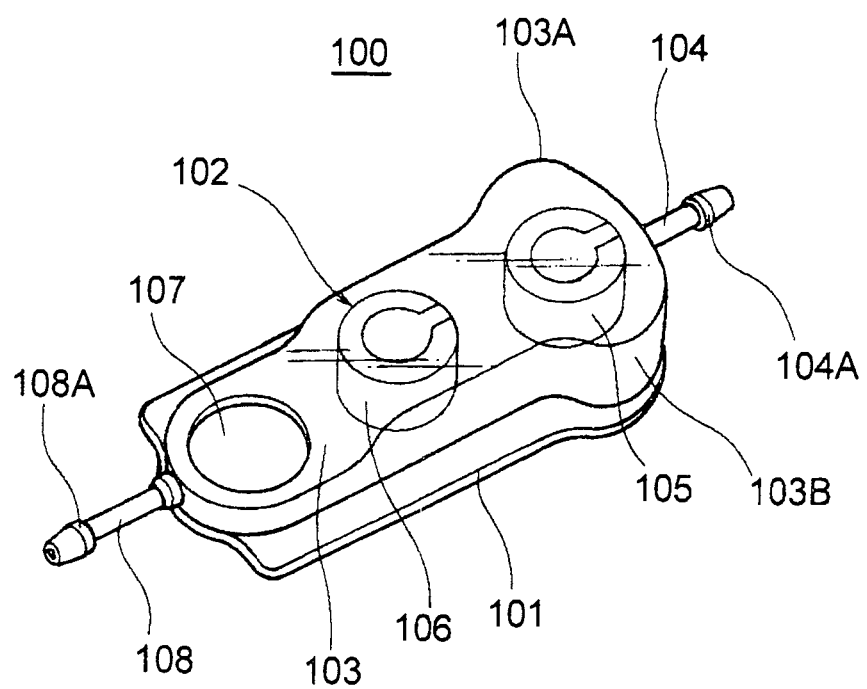
FIG. 19 is an overall perspective view of a shunt valve for treatment of hydrocephalus showing an eighth embodiment of a shunt valve for treatment of hydrocephalus according to the present invention.
Figure 20:
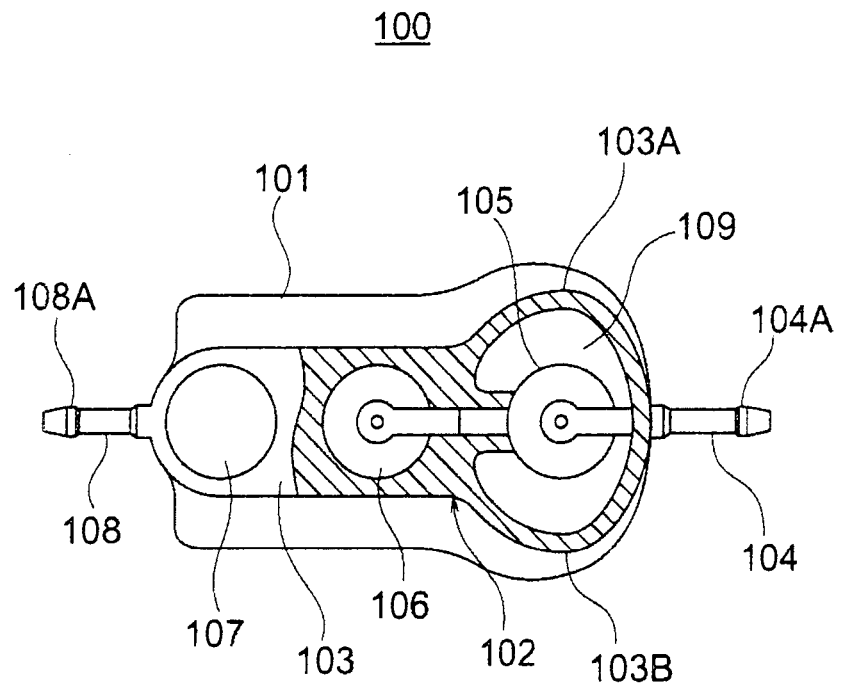
FIG. 20 is a horizontal cross-sectional view of the shunt valve for treatment of hydrocephalus as illustrated in FIG. 19.

FIG. 19 and FIG. 20 illustrate an eighth embodiment of a shunt valve for treatment of hydrocephalus according to the present invention.

In FIG. 19 and FIG. 20, a shunt valve for treatment of hydrocephalus 100 is formed as an integral unit and has a shunt main body 102 which is attached to a cured plastic substrate 101, and a flexible silicone elastomer membrane 103 which covers the entire device.

The eighth embodiment of a shunt valve for treatment of hydrocephalus according to the present invention as illustrated in FIG. 19 and FIG. 20 differs from the sixth embodiment of the shunt valve for treatment of hydrocephalus according to the present invention as illustrated in FIG. 16 and FIG. 17 in that in the sixth embodiment of the shunt valve for treatment of hydrocephalus according to the present invention as illustrated in FIG. 16 and FIG. 17, reservoir 88 is provided between the first valve pressure variable device 75 and the opening portion of the rear end of the inflow connector 74 and has an upper wall constituted of a silicone dome 83A formed by a membrane 73 raised in a dome shape and made of a flexible silicone elastomer (soft silicone resin), whereas in the eighth embodiment as illustrated in FIG. 19 and FIG. 20, reservoir 109 formed between the inflow connector 104 and opening 9A of the first cover 9 of the first valve pressure variable device 105 has an opening portion formed at a rear end of the inflow connector 104 and is constituted of silicone side domes 103A and 103B formed of a membrane 103 raised in a dome shape and made of a flexible silicone elastomer (soft silicone resin) which surrounds the side surface of the first valve pressure variable device 105.

The characteristic of the eight embodiment of the shunt valve for treatment of hydrocephalus according to the present invention as illustrated in FIG. 19 and FIG. 20 is that the flexible silicone elastomer membrane surrounding the side surface of the first valve pressure variable device bulges out in a dome shape on both sides in a longitudinal direction of the shunt main body to form the silicone side domes.

There are no other differences with the sixth embodiment of the shunt valve for treatment of hydrocephalus according to the present invention as illustrated in FIG. 16 and FIG. 17.

In FIG. 19 and FIG. 20, 104 denotes an inflow connector having a cylindrical shape and connecting a rear end of the ventricular catheter having a needle for tapping into the ventricle attached to a leading end thereof, and 104A denotes a protrusion formed at a leading end portion of the inflow connector 104 and projecting to the outside. In FIG. 19 and FIG. 20, 108 denotes an outflow connector having a cylindrical shape and connecting a rear end of a peritoneal catheter which is inserted into the peritoneal cavity and 108A denotes a protrusion formed in a leading end portion of the outflow connector 108 and projecting to the outside.

In FIG. 19 and FIG. 20, 105 denotes a first valve pressure variable device, 106 denotes a second valve pressure variable device, 107 denotes a chamber and 109 denotes a reservoir.

A reservoir 109 is provided on the cerebrospinal fluid inflow side of the first valve pressure variable device 105 and an inflow connector 104 is provided on the inflow side of the cerebrospinal fluid from the reservoir 109. A ventricular catheter is connected to the inflow connector 104 and a peritoneal catheter is connected to the outflow connector 107.

The inflow connector 104 has a similar configuration with the inflow connector of the fifth embodiment as illustrated in FIG. 14 and FIG. 15, and the outflow connector 107 has a similar configuration with the outflow connector 68 of the fifth embodiment as illustrated in FIG. 14 and FIG. 15.

The first valve pressure variable device 105 has a similar configuration with the first valve pressure variable device 65 of the fifth embodiment as illustrated in FIG. 14 and FIG. 15 and the second valve pressure variable device 106 has a similar configuration with the second valve pressure variable device 66 of the fifth embodiment as illustrated in FIG. 14 and FIG. 15.

An opening 20A of the second cover 20 is formed in the outflow tract 14B of the first valve pressure variable device 105 which becomes the cerebrospinal fluid inflow side of the second valve pressure variable device 106 (refer to FIG. 5 and FIG. 6). An outflow connector 108 is attached to an outflow tract 25B which becomes the cerebrospinal fluid output side of the second valve pressure variable device 106.

Reservoir 109 has silicone side domes 103A and 103B formed of a membrane 103 bulging in a dome shape and made of a flexible silicone elastomer (soft silicone resin) which surrounds the side surface of the first valve pressure variable device 105. This reservoir 109 is formed as an open space for accumulating a specific amount of cerebrospinal fluid draining out of the needle connected to the leading end (ventricle end) of the ventricular catheter through the inflow connector 104 and to the outside of the ventricles.

The upper wall of the reservoir 109 and the side wall in a longitudinal direction of the shunt main body 102 are made of a membrane 103 made of a flexible silicone elastomer (soft silicone resin) which is raised in a dome shape and bulges in a side wall periphery of the first valve pressure variable device 105, and silicone side domes 103A and 103B are formed on both sides of the valve pressure variable device 105. When the silicone side domes 103A and 103B are depressed, the cerebrospinal fluid is forced out of the reservoir 109 into the first valve pressure variable device 105 and inflow connector 104 connected thereto.

Following implantation of the shunt valve for treatment of hydrocephalus 100 under the scalp and in the vicinity of the pericranium, the reservoir 109 makes it possible to harvest the cerebrospinal fluid accumulated therein and inject drug solutions such as contrast material and the like therein through a needle which is tapped from outside of the scalp into the membrane 103 forming the silicone side domes 103A and 103B.

After the shunt valve for treatment of hydrocephalus 100 as illustrated in FIG. 19 and FIG. 20 has been implanted under the skull and in the vicinity of the pericranium, the position of the silicone side domes 103A and 103B cannot be visibly confirmed from outside the skull. However, since the membrane 103 made up of silicone elastomer (soft silicone resin) has flexible properties, its position can be confirmed by feeling the top of the scalp with the fingers. The position of the silicone side domes 103A and 103B can be easily confirmed by pinching both sides of the first valve pressure variable device 105 of the shunt valve for treatment of hydrocephalus 100 from the outer side of the scalp and a needle can be easily tapped into the membrane 103 forming the silicone side domes 103A and 103B.

Opening 9A of the first cover 9 (refer to FIGS. 3 and 4) through which the cerebrospinal fluid flows in from the first valve pressure variable device 105 is formed in reservoir 109.

Thus, the eighth embodiment of the shunt valve for treatment of hydrocephalus according to the present invention as illustrated in FIG. 19 and FIG. 20 has the operation of the sixth embodiment of the shunt valve for treatment of hydrocephalus according to the present invention as illustrated in FIG. 16 and FIG. 17, and in addition, the two silicone side domes 103A and 103B formed on both sides of the first valve pressure variable device 105 prevent the overall device from growing in size in a longitudinal direction of the shunt valve for treatment of hydrocephalus, keeping it compact and requiring only a small incision for implantation of the device during surgery, which eases the burden on the patient.

Ninth Embodiment

Figure 21:
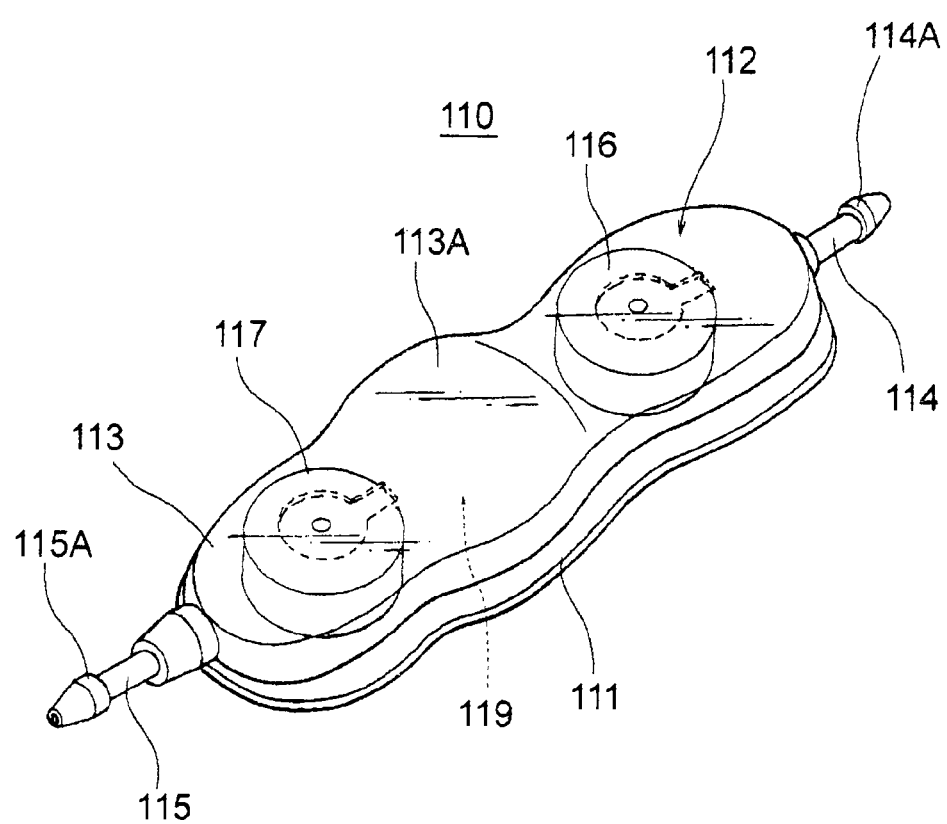
FIG. 21 is an overall perspective view of a shunt valve for treatment of hydrocephalus showing a ninth embodiment of a shunt valve for treatment of hydrocephalus according to the present invention.
Figure 22:
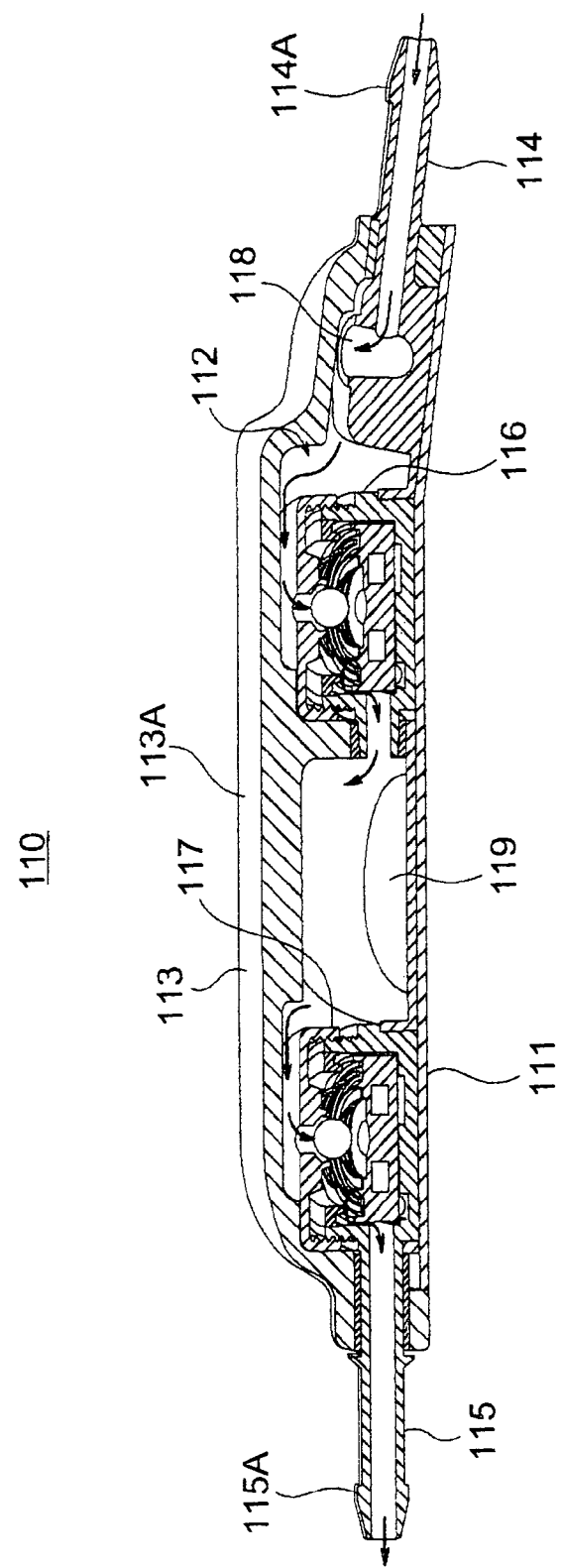
FIG. 22 is a vertical cross-sectional view of the shunt valve for treatment of hydrocephalus as illustrated in FIG. 21.

FIG. 21 and FIG. 22 illustrate a ninth embodiment of a shunt valve for treatment of hydrocephalus according to the present invention.

In FIG. 21 and FIG. 22, a shunt valve for treatment of hydrocephalus 110 is formed as an integral unit and has a shunt main body 112 which is attached to a cured plastic substrate 111, and a flexible silicone elastomer membrane 113 which covers the entire device.

The ninth embodiment of the shunt valve for treatment of hydrocephalus according to the present invention as illustrated in FIG. 21 and FIG. 22 differs from the first embodiment of the shunt valve for treatment of hydrocephalus according to the present invention as illustrated in FIG. 1 in that in the first embodiment of the shunt valve for treatment of hydrocephalus according to the present invention as illustrated in FIG. 1, an opening 20A of the second cover 20 (refer to FIG. 5 and FIG. 6) which becomes the cerebrospinal fluid inflow side of the second valve pressure variable device 8 is formed in the outflow tract 14B of the first valve pressure variable device 7, whereas in a tenth embodiment of a shunt valve for treatment of hydrocephalus according to the present invention as illustrated in FIG. 21 and FIG. 22, a reservoir 119 is provided in the outflow tract 14B of the first valve pressure variable device 116 and a second valve pressure variable device 117 is provided on the outflow side of the reservoir 119 where the cerebrospinal fluid flows into, and also, a ventricle-side occluder 118 having an open top and a bottom is provided in a rear end portion of the inflow connector 114 to temporarily press-close a tract through which the cerebrospinal fluid draining from the ventricles flows.

There are no other differences with the first embodiment of the shunt valve for treatment of hydrocephalus according to the present invention as illustrated in FIG. 1.

In FIG. 21 and FIG. 22, 114 denotes an inflow connector formed in a cylindrical shape and connecting a rear end of a ventricle catheter having a needle which taps into the ventricle attached to a leading end thereof and 114A denotes a protrusion formed in a leading end portion of the inflow connector 114 and projecting to the outside. In FIG. 21 and FIG. 22, 115 denotes an outflow connector formed in a cylindrical shape and connecting a rear end of a peritoneal catheter which is inserted into the peritoneal cavity, and 115A denotes a protrusion formed in a leading end portion of the outflow connector 115 and projecting to the outside.

In FIG. 21 and FIG. 22, 116 denotes a first valve pressure variable device, 117 denotes a second valve pressure variable device, 118 denotes a ventricle-side occluder and 119 denotes a reservoir.

An inflow connector 114 is mounted on the cerebrospinal fluid inflow side of the first valve pressure variable device 116. A ventricular catheter is connected to the inflow connector 114 and a peritoneal catheter is connected to the outflow connector 115.

The inflow connector 114 has a similar configuration with the inflow connector 64 of the fifth embodiment as illustrated in FIG. 14 and FIG. 15, and the outflow connector 115 has a similar configuration with the outflow connector 68 of the fifth embodiment as illustrated in FIG. 14 and FIG. 15.

The first valve pressure variable device 116 has a similar configuration with the first valve pressure variable device 7 as illustrated in FIG. 3 and FIG. 4, and the second valve pressure variable device 117 has a similar configuration with the second valve pressure variable device 8 as illustrated in FIG. 5 and FIG. 6.

The ventricle-side occluder 118 has a similar configuration with the ventricle-side occluder 68 of the fifth embodiment as illustrated in FIG. 14 and FIG. 15, it is provided on the intraventricular cerebrospinal fluid inflow side of the inflow connector 114 and serves to press-close the tract through which the cerebrospinal fluid flows and temporarily stop the flow of the cerebrospinal fluid. The ventricle-side occluder 118 has a cylindrical shape, with an open top and a bottom, and is formed in a rear end of the inflow connector 114, as an integral unit with the membrane 113 made of a flexible silicone elastomer (soft silicone resin). The ventricle-side occluder 118 serves to press-close the tract of the cerebrospinal fluid flowing in through the inflow connector 114 and temporarily stop the inflow of the cerebrospinal fluid.

Reservoir 119 has a similar configuration with reservoir 78 of the sixth embodiment as illustrated in FIG. 16 and FIG. 17 and is a chamber (open space) formed between the first valve pressure variable device 116 and the second valve pressure variable device 117 serving to accumulate a specific amount of cerebrospinal fluid. The upper wall of reservoir 119 is constituted of a silicone dome 113A comprised of a membrane 113 made of a flexible silicone elastomer (soft silicone resin) having a dome shape, and when the silicone dome 113A is depressed, the cerebrospinal fluid is forced out of the reservoir 119.

Following implantation of the shunt valve 110 for treatment of hydrocephalus under the scalp and in the vicinity of the pericranium, the reservoir 119 makes it possible to harvest the cerebrospinal fluid accumulated therein and inject drug solutions such as contrast material and the like therein through a needle which is tapped from outside of the scalp into the membrane 113 forming the silicone dome 113A.

Accordingly, the shunt valve for treatment of hydrocephalus of the ninth embodiment according to the present invention has the operation of the first embodiment of the shunt valve for treatment of hydrocephalus according to the present invention as illustrated in FIG. 1, and in addition, following implantation of the shunt valve 110 for treatment of hydrocephalus under the scalp and in the vicinity of the pericranium, the reservoir 119 makes it possible to harvest the cerebrospinal fluid accumulated therein and inject drug solutions such as contrast material and the like therein through a needle which is tapped from outside of the scalp into the membrane 113 forming the silicone dome 113A.

Tenth Embodiment

Figure 23:
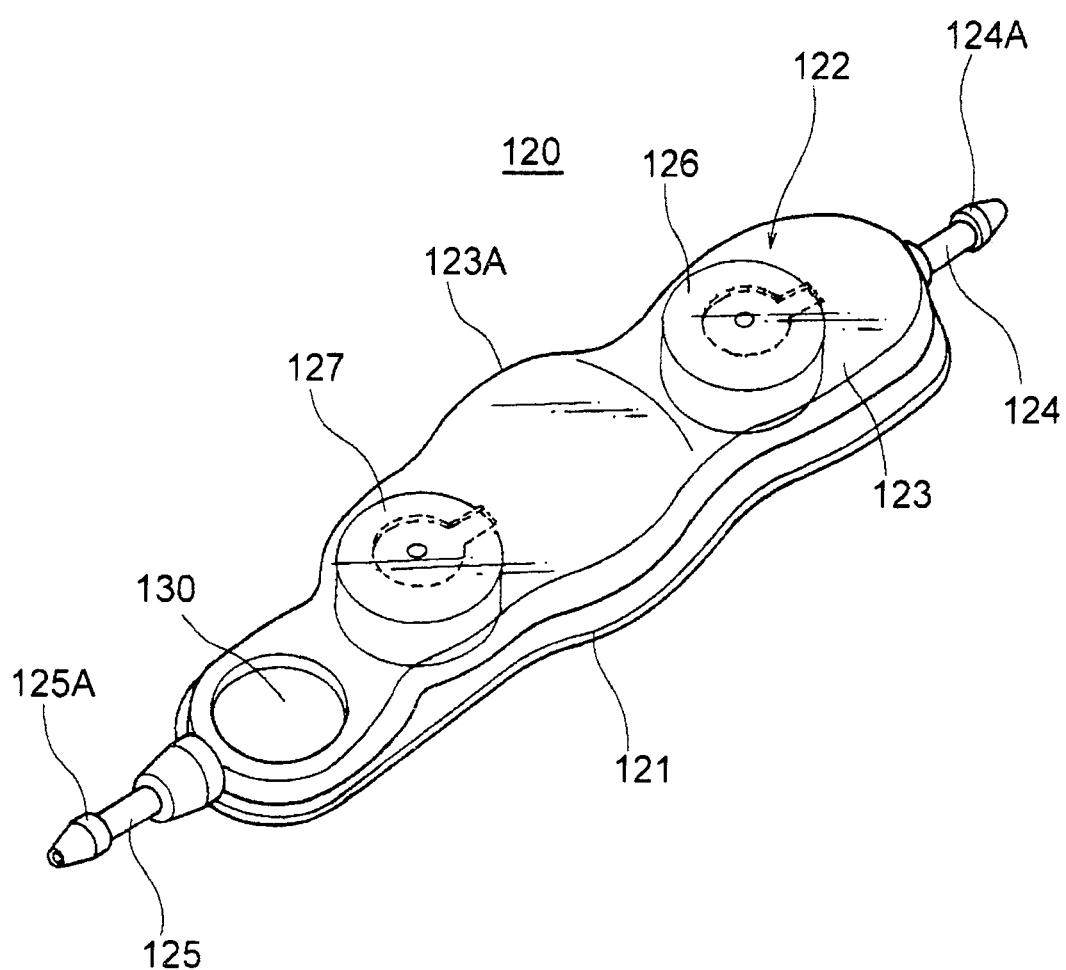
FIG. 23 is an overall perspective view of a shunt valve for treatment of hydrocephalus showing a tenth embodiment of a shunt valve for treatment of hydrocephalus according to the present invention.
Figure 24:
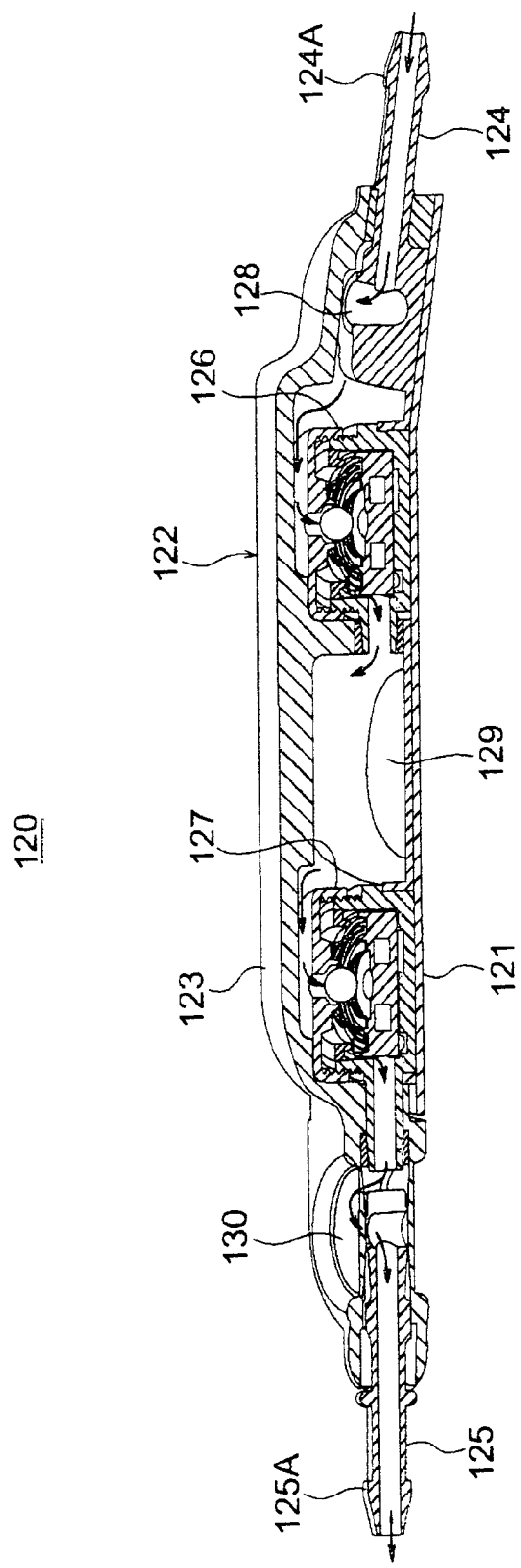
FIG. 24 is a vertical cross-sectional view of the shunt valve for treatment of hydrocephalus as illustrated in FIG. 23.

FIG. 23 and FIG. 24 illustrate a tenth embodiment of a shunt valve for treatment of hydrocephalus according to the present invention.

In FIG. 23 and FIG. 24, a shunt valve for treatment of hydrocephalus 120 is formed as an integral unit and has a shunt main body 122 which is attached to a cured plastic substrate 121, and a flexible silicone elastomer membrane 123 which covers the entire device.

The tenth embodiment of the shunt valve for treatment of hydrocephalus according to the present invention as illustrated in FIG. 23 and FIG. 24 differs from the ninth embodiment of the shunt valve for treatment of hydrocephalus according to the present invention as illustrated in FIG. 21 and FIG. 22 in that a chamber 130 is provided between the second valve pressure variable device 117 and the outflow connector 115 of the ninth embodiment of the shunt valve for treatment of hydrocephalus according to the present invention as illustrated in FIG. 21 and FIG. 22.

There are no other differences with the ninth embodiment of the shunt valve for treatment of hydrocephalus according to the present invention as illustrated in FIG. 21 and FIG. 22.

In FIG. 23 and FIG. 24, 124 denotes an inflow connector formed in a cylindrical shape and connecting a rear end of a ventricle catheter having a needle that taps into the ventricle attached to a leading end thereof, and 124A denotes a protrusion formed at a leading end portion of the inflow connector 124 and projecting to the outside. In FIG. 23 and FIG. 24, 125 denotes an outflow connector formed in a cylindrical shape and connecting a rear end of a peritoneal catheter inserted in the peritoneal cavity, and 125A denotes a protrusion formed in a leading end portion of the outflow connector 125 and projecting to the outside. In FIG. 23 and FIG. 24, 126 denotes a first valve pressure variable device, 127 denotes a second valve pressure variable device, 128 denotes a ventricle-side occluder, 129 denotes a reservoir and 130 denotes a chamber.

An inflow connector 124 is provided at a cerebrospinal fluid inflow side of the first pressure variable device 126. A ventricular catheter is connected to the inflow connector 124 and a peritoneal catheter is connected to the outflow connector 125.

Inflow connector 124 has a similar configuration with the inflow connector 64 of the fifth embodiment as illustrated in FIG. 14 and FIG. 15, and the outflow connector 125 has a similar configuration with the outflow connector 68 of the fifth embodiment as illustrated in FIG. 14 and FIG. 15.

The first valve pressure variable device 126 has a similar configuration with the first valve pressure variable device 7 as illustrated in FIG. 3 and FIG. 4, and the second valve pressure variable device 127 has a similar configuration with the second valve pressure variable device 8 as illustrated in FIG. 5 and FIG. 6.

The ventricle-side occluder 128 has a similar configuration with the ventricle-side occluder 68 of the fifth embodiment as illustrated in FIG. 14 and FIG. 15 and is provided on the intraventricular cerebrospinal fluid inflow side of the inflow connector 124, serving to press-close the tract through which the cerebrospinal fluid flows and temporarily stop the flow of the cerebrospinal fluid. The ventricle-side occluder 128 has a cylindrical shape, with an open top and a bottom, and is formed in a rear end of the inflow connector 124, as an integral unit with the membrane 123 made of a flexible silicone elastomer (soft silicone resin). The ventricle-side occluder 128 serves to press-close the tract of the cerebrospinal fluid flowing in through the inflow connector 124 and temporarily stop the inflow of the cerebrospinal fluid.

The reservoir 129 has a similar configuration with the reservoir 78 of the sixth embodiment as illustrated in FIG. 16 and FIG. 17 and is formed between the first valve pressure variable device 126 and the second valve pressure variable device 127, serving as a chamber (open space) for accumulating a specific amount of cerebrospinal fluid. The upper wall of the reservoir 129 is constituted as a silicone dome 123A formed of a membrane 123 made of a flexible silicone elastomer (soft silicone resin) and shaped as a dome, and when the silicone dome 123A is depressed, the cerebrospinal fluid is forced out of the reservoir 129.

Following implantation of the shunt valve for treatment of hydrocephalus 120 under the scalp and in the vicinity of the pericranium, the reservoir 129 makes it possible to harvest the cerebrospinal fluid accumulated therein and inject drug solutions such as contrast material and the like therein through a needle which is tapped from outside of the scalp into the membrane 123 forming the silicone dome 163A.

Chamber 130 prevents sudden outflow of the intraventricular cerebrospinal fluid and a sudden drop in the intraventricular pressure occurring when a patient suddenly sits up from a lying down position. The chamber 130 has a check valve which opens in the event the cerebrospinal fluid is forced to flow due to high intraventricular pressure, and closes when a negative pressure is created inside the peritoneal catheter to nullify the siphon effect of the cerebrospinal fluid. Chamber 130 has a cavity where the cerebrospinal fluid which normally drains out of the ventricles primarily accumulates when the valve closes due to the negative pressure.

Accordingly, the shunt valve for treatment of hydrocephalus of the tenth embodiment according to the present invention has the operation of the ninth embodiment of the shunt valve for treatment of hydrocephalus according to the present invention as illustrated in FIG. 21 and FIG. 22, and in addition, the occurrence of various symptoms such as sudden headaches, sudden impaired awareness can be prevented. These symptoms occur when a patient suddenly sits up from a posture wherein intraventricular pressure is kept constant by the shunt valve for treatment of hydrocephalus and the amount of intraventricular cerebrospinal fluid decreases, leading to a sudden drop in the intraventricular pressure, which in turn causes the ventricles to become smaller and narrower, a condition known as the slit ventricle syndrome.

Eleventh Embodiment

Figure 25:
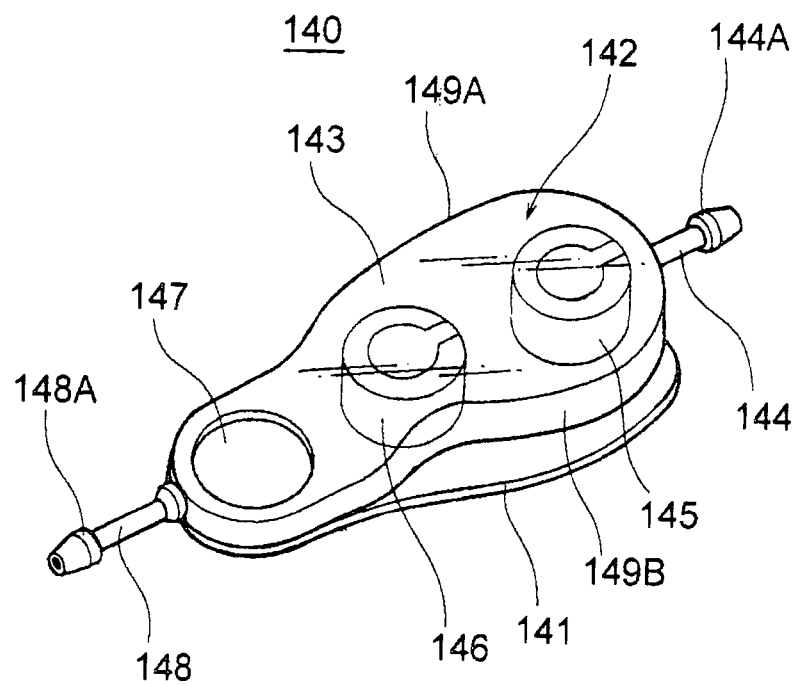
FIG. 25 is an overall perspective view of a shunt valve for treatment of hydrocephalus showing an eleventh embodiment of a shunt valve for treatment of hydrocephalus according to the present invention.
Figure 26:
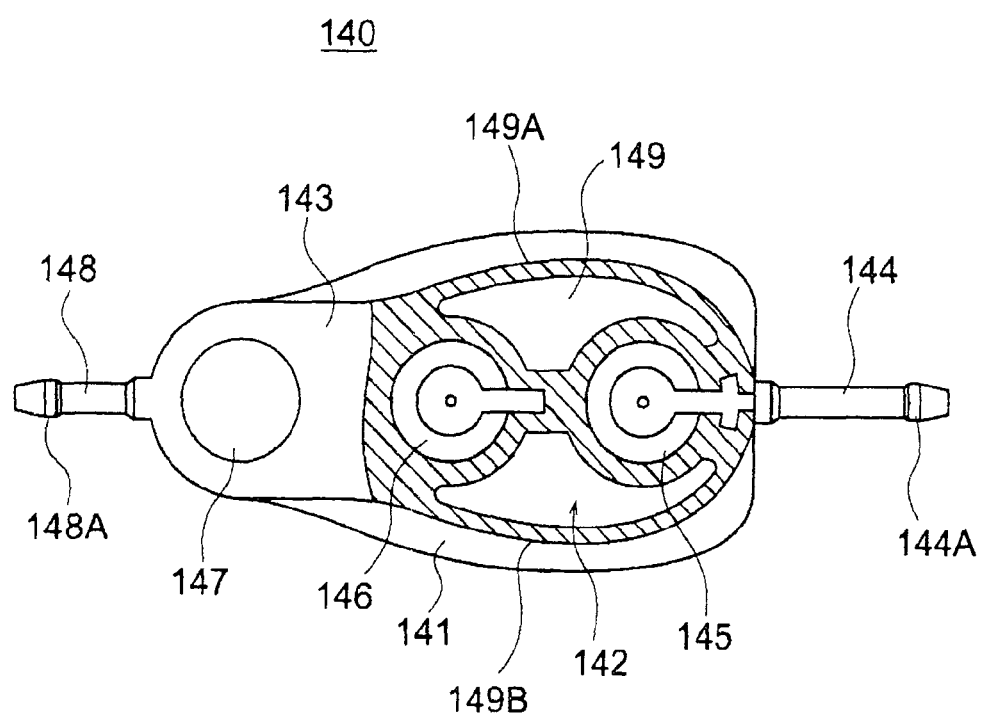
FIG. 26 is a horizontal cross-sectional view of the shunt valve for treatment of hydrocephalus as illustrated in FIG. 25.
Figure 27:
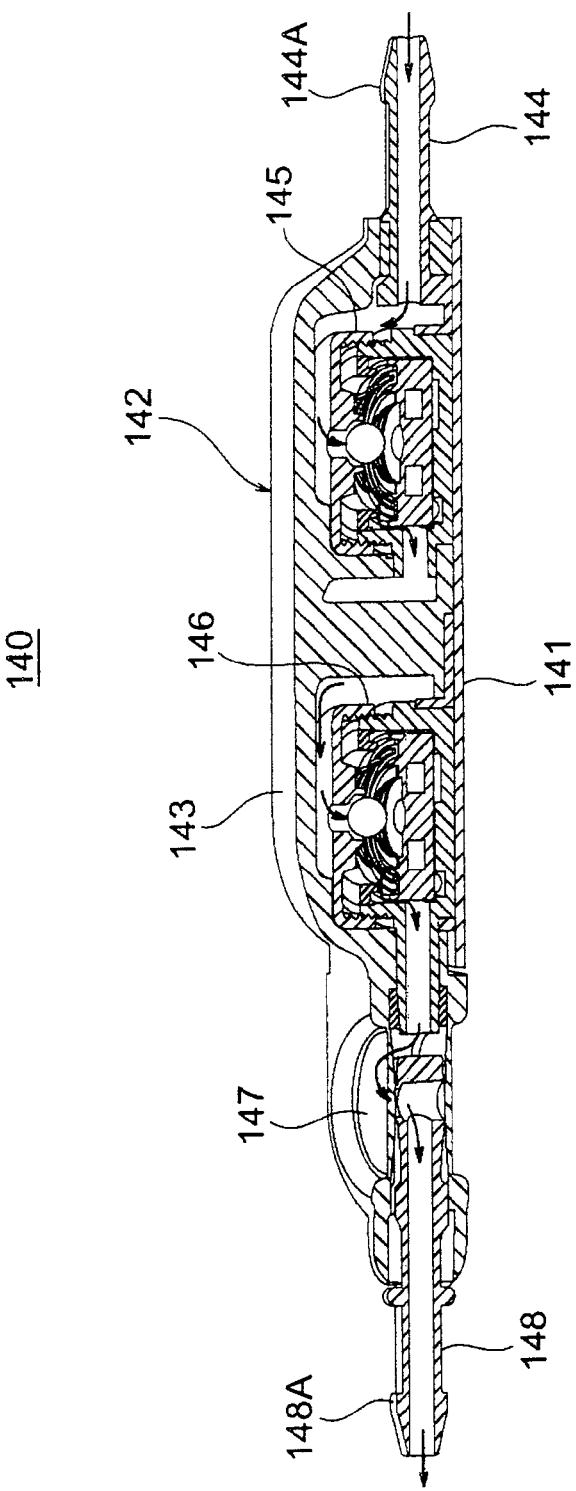
FIG. 27 is a vertical cross-sectional view of a shunt valve for treatment of hydrocephalus as illustrated in FIG. 25.

FIG. 25 through FIG. 27 illustrate an eleventh embodiment of a shunt valve for treatment of hydrocephalus according to the present invention. In FIG. 25 through FIG. 27, a shunt valve for treatment of hydrocephalus 140 is formed as an integral unit and has a shunt main body 142 which is mounted to a cured plastic substrate 141, and a flexible silicone elastomer membrane 143 which covers the entire device.

The eleventh embodiment of a shunt valve for treatment of hydrocephalus according to the present invention as illustrated in FIG. 25 through FIG. 27 differs from the tenth embodiment of a shunt valve for treatment of hydrocephalus according to the present invention as illustrated in FIG. 23 and FIG. 24 in that in the tenth embodiment of a shunt valve for treatment of hydrocephalus according to the present invention as illustrated in FIG. 23 and FIG. 24, a reservoir 129 is provided in the outflow tract 14B of the first valve pressure variable device 126 and a second valve pressure variable device 127 is provided on the outflow side of the reservoir 129 to receive the cerebrospinal fluid from the reservoir 129, whereas in the eleventh embodiment of a shunt valve for treatment of hydrocephalus according to the present invention as illustrated in FIG. 25 through FIG. 27 a reservoir 149 is provided. Reservoir 149 supplies the cerebrospinal fluid flowing from the inflow connector 144 into the shunt main body 142 directly inside the first valve main body 10 through the opening 9A in the first cover 9 of the first valve pressure variable device 145 and is constituted of silicone side domes 143A and 143B formed of a membrane 143 bulging out in a dome shape on both sides in a longitudinal direction of a shunt main body 142 and made of a flexible silicone elastomer (soft silicone resin). The reservoir 149 is mounted between the outflow tract 14B of the first valve pressure variable device 145 and the second valve pressure variable device 146 on both sides in a longitudinal direction of the shunt main body 142, stretching over the two side surfaces of the first valve pressure variable device 145 and the second valve pressure variable device 146 which are connected in a longitudinal direction of the shunt main body 142 and adjacent to the first valve pressure variable device 145 and the second valve pressure variable device 146 in the direction they are lined up.

The eleventh embodiment of the shunt valve for treatment of hydrocephalus according to the present invention as illustrated in FIG. 25 through FIG. 27 is characterized by the fact that unlike the reservoirs of the ninth embodiment as illustrated in FIG. 21 and FIG. 22, and in the tenth embodiment as illustrated in FIG. 23 and FIG. 24 which are formed by widening the spacing between the first valve pressure variable device and the second valve pressure variable device to create a space between the inflow side of the first valve pressure variable device and the second valve pressure variable device, in the present embodiment, the reservoir is arranged without having to widen the spacing between the first valve pressure variable device and the second valve pressure variable device. Specifically, the reservoir is arranged so as to be adjacent to a side surface of the first valve pressure variable device and a side surface of the second valve pressure variable device, over a longitudinal direction of the shunt main body and has silicone side domes formed of flexible silicone elastomer membranes bulging out in a dome shape on both sides in a longitudinal direction of the shunt main body.

In FIG. 25 through FIG. 27, 144 denotes an inflow connector having a cylindrical shape and to which a rear end of a ventricular catheter having a needle for tapping inside the ventricle attached to a leading end thereof is connected, and 144A denotes a protrusion formed at a leading end of the inflow connector 144 and projecting to the outside. In FIG. 25 through FIG. 27, 148 denotes an outflow connector having a cylindrical shape to which a rear end of a peritoneal catheter inserted in the peritoneal cavity is connected, and 148A denotes a protrusion formed at a leading end of the outflow connector 148 and projecting to the outside.

In FIG. 25 through FIG. 27, 145 denotes a first valve pressure variable device, 146 denotes a second valve pressure variable device, 147 denotes a chamber and 149 denotes a reservoir.

The rear end of the inflow connector 144 connecting the rear end of the ventricular catheter having a needle for tapping inside the ventricle attached to a leading end thereof communicates with the cerebrospinal fluid inflow side of the first valve pressure variable device 145, so that the cerebrospinal fluid flowing from the rear end of the outflow connector 148 is directly supplied from the opening 9A in the first cover 9 of the first valve pressure variable device 145 to the inside of the first valve main body 10 (refer to FIG. 3 and FIG. 4).

A reservoir 149 is provided in the outflow tract 14B of the first valve pressure variable device 145, and an opening 20A of the second cover 20 which becomes the cerebrospinal fluid inflow side of the second valve pressure variable device 146 is formed in an inflow side where the cerebrospinal fluid flows in from the reservoir 149 (refer to FIG. 5 and FIG. 6). Also, an outflow connector 148 is mounted in the outflow tract 25B which is the cerebrospinal fluid outflow side of the second valve pressure variable device 146.

The reservoir 149 is arranged so as to be adjacent to and stretch over on both sides in a longitudinal direction of the side surface of the first valve pressure variable device 145 and the side surface of the second valve pressure variable device 146, over a longitudinal direction of the shunt main body 142 and has silicone side domes 143A and 143B formed of a flexible silicone elastomer membrane 143 bulging out in a dome shape on both sides in a longitudinal direction of the shunt main body 142. The reservoir 149 is formed as a cavity for primarily accumulating the cerebrospinal fluid flowing from a needle connected to the leading end (ventricle end) of the ventricular catheter through the inflow connector 84 and out of the ventricles, following primary adjustment of the fluid pressure thereof in the first valve pressure variable device 145.

The upper wall of the reservoir 149 and the side wall of the shunt main body 142 in a longitudinal direction thereof are formed of a flexible silicone elastomer (soft silicone resin) membrane 143 which is raised in a dome shape and bulges out on both sides in a longitudinal direction of the shunt main body 142, forming silicone side domes 143A and 143B on both sides in a longitudinal direction thereof. Then, when the silicone side domes 143A and 143B are depressed, the cerebrospinal fluid is forced out of the reservoir 149 into the first valve pressure variable device 145 and the second valve pressure variable device 146 connected thereto.

Following implantation of the shunt valve for treatment of hydrocephalus 140 under the scalp and in the vicinity of the pericranium, the reservoir 149 makes it possible to harvest the cerebrospinal fluid accumulated therein and inject drug solutions such as contrast material and the like therein through a needle which is tapped from outside of the scalp into the membrane 143 forming the silicone side domes 143A and 143B.

After the shunt valve for treatment of hydrocephalus 140 as illustrated in FIG. 25 through FIG. 27 is arranged under the scalp and in the vicinity of the pericranium, the position of the silicone side domes 143A and 143B can no longer be visually confirmed from outside of the scalp. However, as the membrane 143 is made of a flexible silicone elastomer (soft silicone resin), its position can be confirmed by feeling the top of the scalp with the fingers. The position of the silicone side domes 143A and 143B can be easily confirmed by pinching the shunt valve for treatment of hydrocephalus 140 from the outer side of the scalp and a needle can be easily tapped into the membrane 143 forming the silicone side domes 143A and 143B.

The opening 20A of the second cover 20 through which the cerebrospinal fluid flows from the second valve pressure variable device 146 is formed in the reservoir 149 (refer to FIG. 5 and FIG. 6).

Thus, the eleventh embodiment of the shunt valve for treatment of hydrocephalus according to the present invention as illustrated in FIG. 25 through FIG. 27 has the operation of the ninth embodiment as illustrated in FIG. 21 and FIG. 22, and the tenth embodiment as illustrated in FIG. 23 and FIG. 24 and unlike the reservoirs in the ninth embodiment as illustrated in FIG. 21 and FIG. 22 and the tenth embodiment as illustrated in FIG. 23 and FIG. 24 which are formed by widening the spacing between the first valve pressure variable device and the second valve pressure variable device to create a space between the outflow tract of the first valve pressure variable device and the opening in the second cover of the second valve pressure variable device, and have a membrane 143 made of a silicone elastomer (soft silicone resin) and built up in a dome shape, the reservoir of this embodiment has two silicone side domes 143A and 143B formed on either side of the first valve pressure variable device 145 and the second valve pressure variable device 146. Accordingly, this helps prevent an increase in the size of the shunt valve for treatment of hydrocephalus in a longitudinal direction thereof, keeping it compact and requiring only a small incision for implantation of the device through surgery, which eases the burden on the patient.

Twelfth Embodiment

Figure 28:
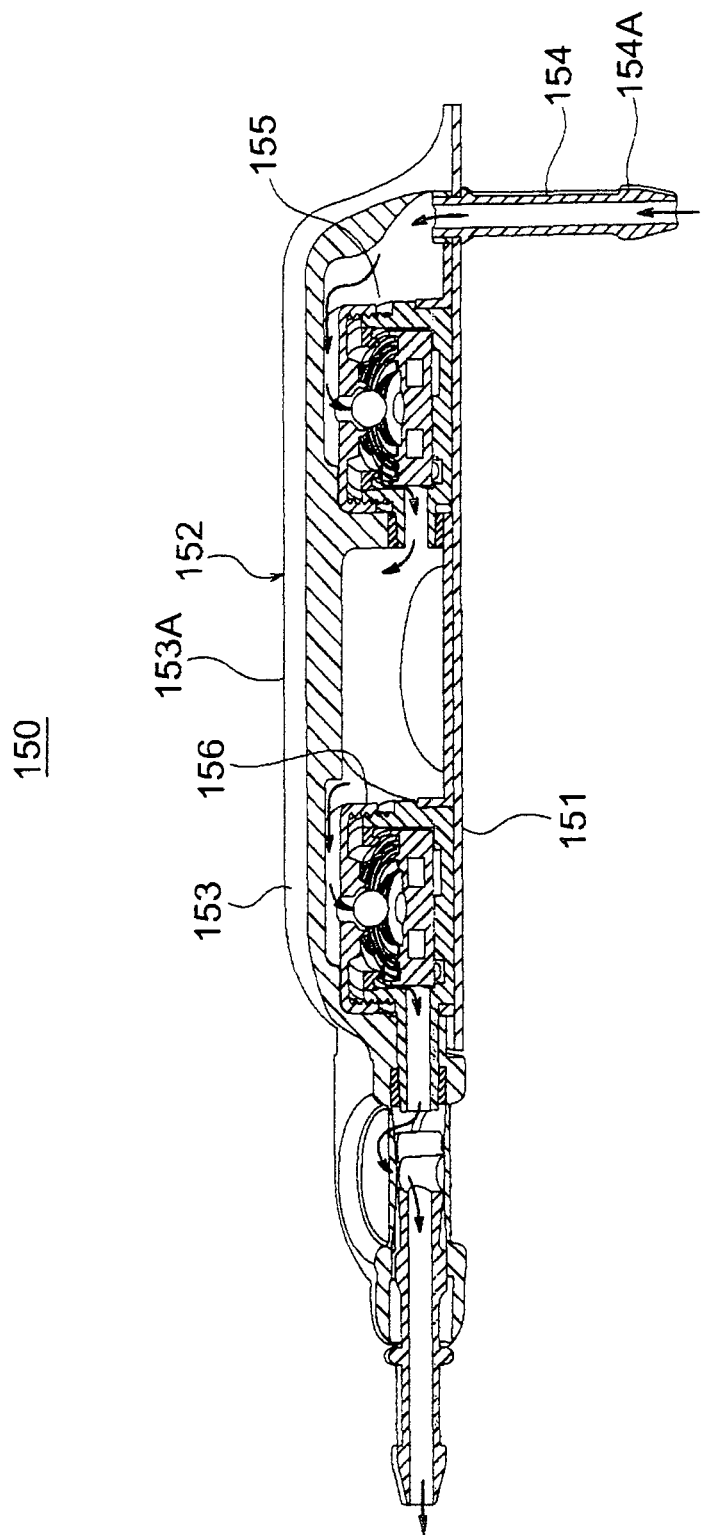
FIG. 28 is a cross-sectional view of a shunt valve for treatment of hydrocephalus showing a twelfth embodiment of a shunt valve for treatment of hydrocephalus according to the present invention.

FIG. 28 illustrates a twelfth embodiment of a shunt valve for treatment of hydrocephalus according to the present invention.

In FIG. 28, a shunt valve for treatment of hydrocephalus 150 is formed as an integral unit and has a shunt main body 152 which is mounted to a cured plastic substrate 151, and a flexible silicone elastomer membrane 153 which covers the entire device.

The twelfth embodiment of a shunt valve for treatment of hydrocephalus according to the present invention as illustrated in FIG. 28 differs from the ninth embodiment of the shunt valve for treatment of hydrocephalus according to the present invention as illustrated in FIG. 21 and FIG. 22 in that unlike the ninth embodiment as illustrated in FIG. 21 and FIG. 22 wherein the inflow connector 114 is provided in the shunt main body 112 which is covered by a silicone elastomer membrane 113 in its entirety, in a longitudinal direction of the cured plastic substrate 111 of the shunt valve for treatment of hydrocephalus 114, in the twelfth embodiment as illustrated in FIG. 28, an inflow connector 154 is provided so as to penetrate the cured plastic substrate 151 of the shunt valve 150 for treatment of hydrocephalus from a shunt main body 152 which is covered by a silicone elastomer membrane 153 in its entirety.

There are no other differences with the ninth embodiment of the shunt valve for treatment of hydrocephalus according to the present embodiment as illustrated in FIG. 22.

In FIG. 28, 154A denotes a protrusion formed at the leading end of the inflow connector 154 and projecting to the outside and connects the rear end of the ventricular catheter having a needle for tapping inside the ventricle attached to the leading end thereof.

A shunt valve for treatment of hydrocephalus 150 according to the present invention as illustrated in FIG. 28 and having the above-described configuration has an inflow connector 154 penetrating from a cured plastic substrate 151 side and continuing downwards, and is mounted as illustrated in FIG. 9.

Specifically, first, a small incision 31A is made in the skull 31 through surgery (refer to FIG. 9), the membrane between the skull 31 and the brain is opened, and the needle attached to the leading end of the ventricular catheter is inserted inside the lateral ventricle through the incision 31A and the rear end of the ventricular catheter is connected to the inflow connector 154. Then, the inflow connector 154 projecting downwards from the cured plastic substrate 151 is inserted into the incision 31A made in the skull 31 and is implanted between the scalp and the skull 31.

Accordingly, the shunt valve for treatment of hydrocephalus, 150 according to the invention as illustrated in FIG. 28, can help stabilize the shunt valve for treatment of hydrocephalus 150 which was implanted between the scalp and the skull 31.

Thirteenth Embodiment

Figure 29:
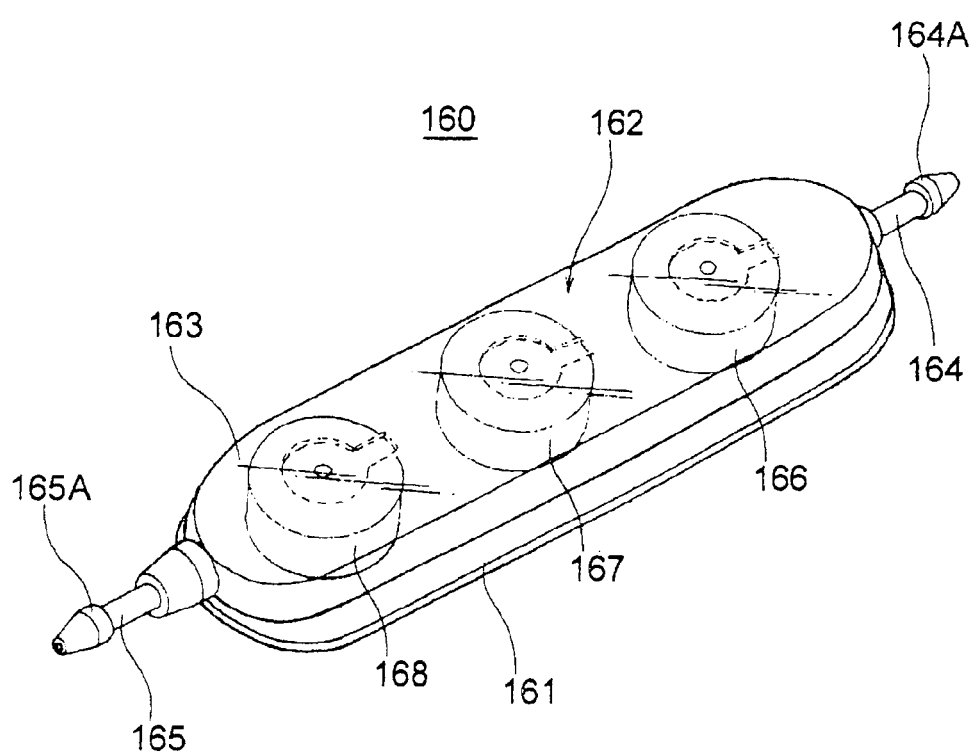
FIG. 29 is an overall perspective view of a shunt valve for treatment of hydrocephalus showing a thirteenth embodiment of a shunt valve for treatment of hydrocephalus according to the present invention.
Figure 30:
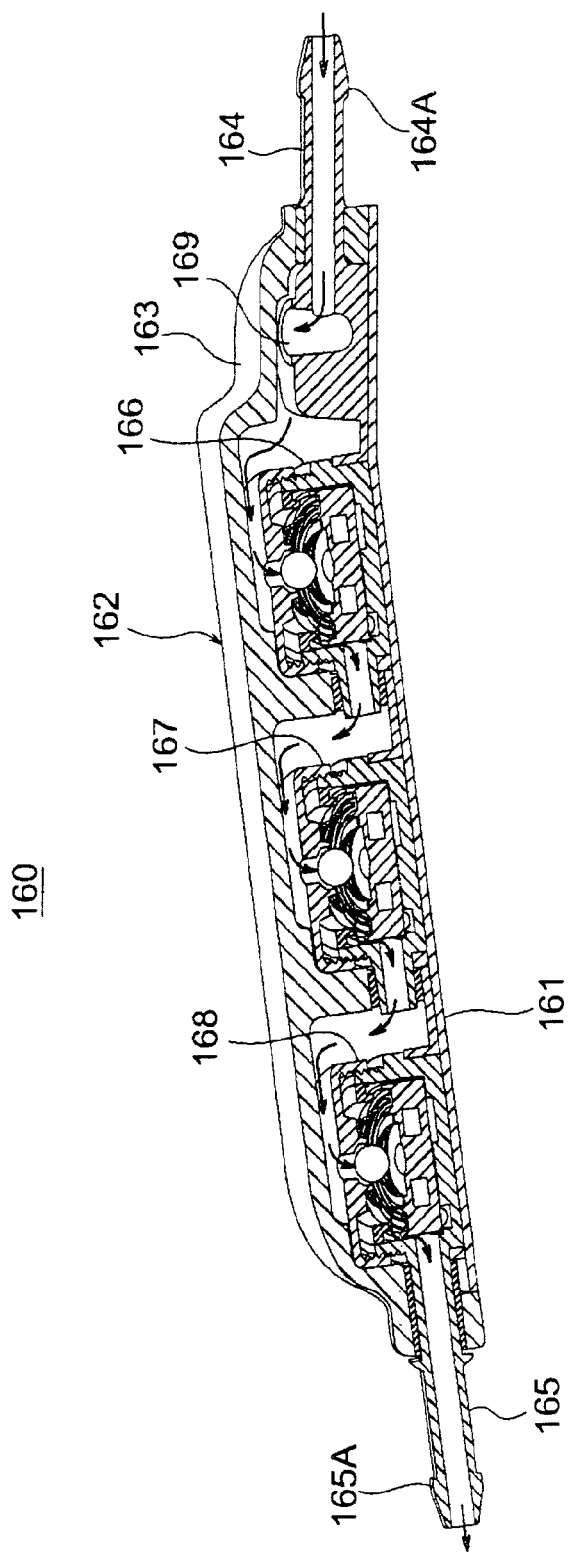
FIG. 30 is a vertical cross-sectional view of the shunt valve for treatment of hydrocephalus as illustrated in FIG. 29.

FIG. 29 and FIG. 30 show a thirteenth embodiment of a shunt valve for treatment of hydrocephalus according to the present invention.

In FIG. 29 and FIG. 30, a shunt valve for treatment of hydrocephalus 160 is formed as an integral unit and has a shunt main body 162 which is mounted to a cured plastic substrate 161, and a flexible silicone elastomer membrane 163 which covers the entire device.

The thirteenth embodiment of a shunt valve for treatment of hydrocephalus according to the present invention as illustrated in FIG. 29 and FIG. 30 differs from the first embodiment of the shunt valve for treatment of hydrocephalus according to the present invention as illustrated in FIG. 1 in that the first embodiment of the shunt valve for treatment of hydrocephalus according to the invention as illustrated in FIG. 1 employs twin devices which are first valve pressure variable device 7 and second valve pressure variable device 8, whereas the thirteenth embodiment of a shunt valve for treatment of hydrocephalus according to the present invention as illustrated in FIG. 29 and FIG. 30 employs triple devices which are: a first valve pressure variable device 166, a second valve pressure variable device 167 and a third valve pressure variable device 168.

In FIG. 29 and FIG. 30, 164 denotes an inflow connector having a cylindrical shape and connecting the rear end of a ventricular catheter having a needle for tapping inside the ventricle attached to a leading end thereof, and 164A denotes a protrusion formed at the leading end of the inflow connector 164 and projecting to the outside. In FIG. 29 and FIG. 30, 165 denotes an outflow connector having a cylindrical shape and connecting a rear end of a peritoneal catheter inserted in the peritoneal cavity, and 165A denotes a protrusion formed at a leading end of the outflow connector 165 and projecting to the outside.

In FIG. 29 and FIG. 30, 166 denotes a first valve pressure variable device, 167 denotes a second valve pressure variable device, 168 denotes a third valve pressure variable device and 169 denotes a ventricle-side occluder.

The inflow connector 164 is mounted at the cerebrospinal fluid inflow side of the first valve pressure variable device 166. A ventricular catheter is connected to the inflow connector 164 and a peritoneal catheter is connected to the outflow connector 165.

The inflow connector 164 has a similar configuration with the inflow connector 64 of the fifth embodiment as illustrated in FIG. 14 and FIG. 15, while the outflow connector 165 has a similar configuration with the outflow connector 68 of the fifth embodiment as illustrated in FIG. 14 and FIG. 15.

Also, the first valve pressure variable device 166 has a similar configuration with the first valve pressure variable device 65 of the fifth embodiment as illustrated in FIG. 14 and FIG. 15, while the second valve pressure variable device 167 has a similar configuration with the second valve pressure variable device 66 of the fifth embodiment as illustrated in FIG. 14 and FIG. 15, and the third valve pressure variable device 168 has a similar configuration with the second valve pressure variable device 66 of the fifth embodiment as illustrated in FIG. 14 and FIG. 15.

The ventricle-side occluder 169 has a similar configuration with the ventricle-side occluder 68 of the fifth embodiment as illustrated in FIG. 14 and FIG. 15.

An opening 20A of the second cover 20 is formed in the outflow tract 14B of the first valve pressure variable device 166 and will become the inflow side of the cerebrospinal fluid in the second pressure variable device 167 (refer to FIG. 5 and FIG. 6). An opening 20A of the second cover 20 which becomes the inflow side of the cerebrospinal fluid in the third valve pressure variable device 168 is formed in the outflow tract 25B which is the output side of the cerebrospinal fluid from the second valve pressure variable device 167 (refer to FIG. 5 and FIG. 6). Further, an outflow connector 165 is mounted in an outflow tract 25B which is the output side of the cerebrospinal fluid from the third valve pressure variable device 168.

The relationship between the intraventricular pressure and the flow rate of the cerebrospinal fluid flowing out of the ventricles following adjustment of the first valve pressure variable device 166, the second valve pressure variable device 167 and the third valve pressure variable device 168 provided in the shunt valve for treatment of hydrocephalus of the thirteenth embodiment of the present invention is as follows.

Specifically, if valve adjustment of the first valve pressure variable device 166, valve adjustment of the second valve pressure variable device 167 and valve adjustment of the third valve pressure variable device 168 is carried out, intraventricular pressure in the shunt valve for treatment of hydrocephalus 160 is set based on the highest value from amongst the three adjusted pressures of the above-mentioned devices: adjusted pressure following adjustment of the first valve pressure variable device 166, adjusted pressure following adjustment of the second valve pressure variable device 167 and adjusted pressure following adjustment of the third valve pressure variable device 168. In this case, the flow rate of the cerebrospinal fluid flowing out of the ventricles is equal to the sum of the flow rate of the cerebrospinal fluid following valve adjustment of the first valve pressure variable device 166, the flow rate of the cerebrospinal fluid following valve adjustment of the second valve pressure variable device 167 and the flow rate of the cerebrospinal fluid following valve adjustment of the third valve pressure variable device 168. The flow rate of the cerebrospinal fluid is based on adjustment of the cerebrospinal fluid pressure following valve adjustment of the first valve pressure variable device 166, the cerebrospinal fluid pressure following valve adjustment of the second valve pressure variable device 167 and the cerebrospinal fluid pressure following valve adjustment of the third valve pressure variable device 168 and is apparent in the change in the flow velocity of the cerebrospinal fluid of the first valve pressure variable device 166, the flow velocity of the cerebrospinal fluid of the second valve pressure variable device 167 and the flow velocity of the cerebrospinal fluid of the third valve pressure variable device 168.

Thus, in the shunt valve for treatment of hydrocephalus 160, intraventricular pressure can slowly be lowered (or raised) and the flow rate of the cerebrospinal fluid per unit square can be increased (or decreased) and adjustments can be made in accordance with the condition of the patient who received the implant of the shunt valve for treatment of hydrocephalus 160.

According to the shunt valve for treatment of hydrocephalus of the thirteenth embodiment according to the present invention, as valve adjustment of the first valve pressure variable device 166 and valve adjustment of the second valve pressure variable device 167 and the third valve pressure variable device 168 can be carried out independently from one another, unlike the conventional shunt valve for treatment of hydrocephalus which can be adjusted in 5 ways, the device of the present invention can be adjusted in 125 ways, enabling even finer adjustment with respect to hydrocephalus patients.

Fourteenth Embodiment

Figure 31:
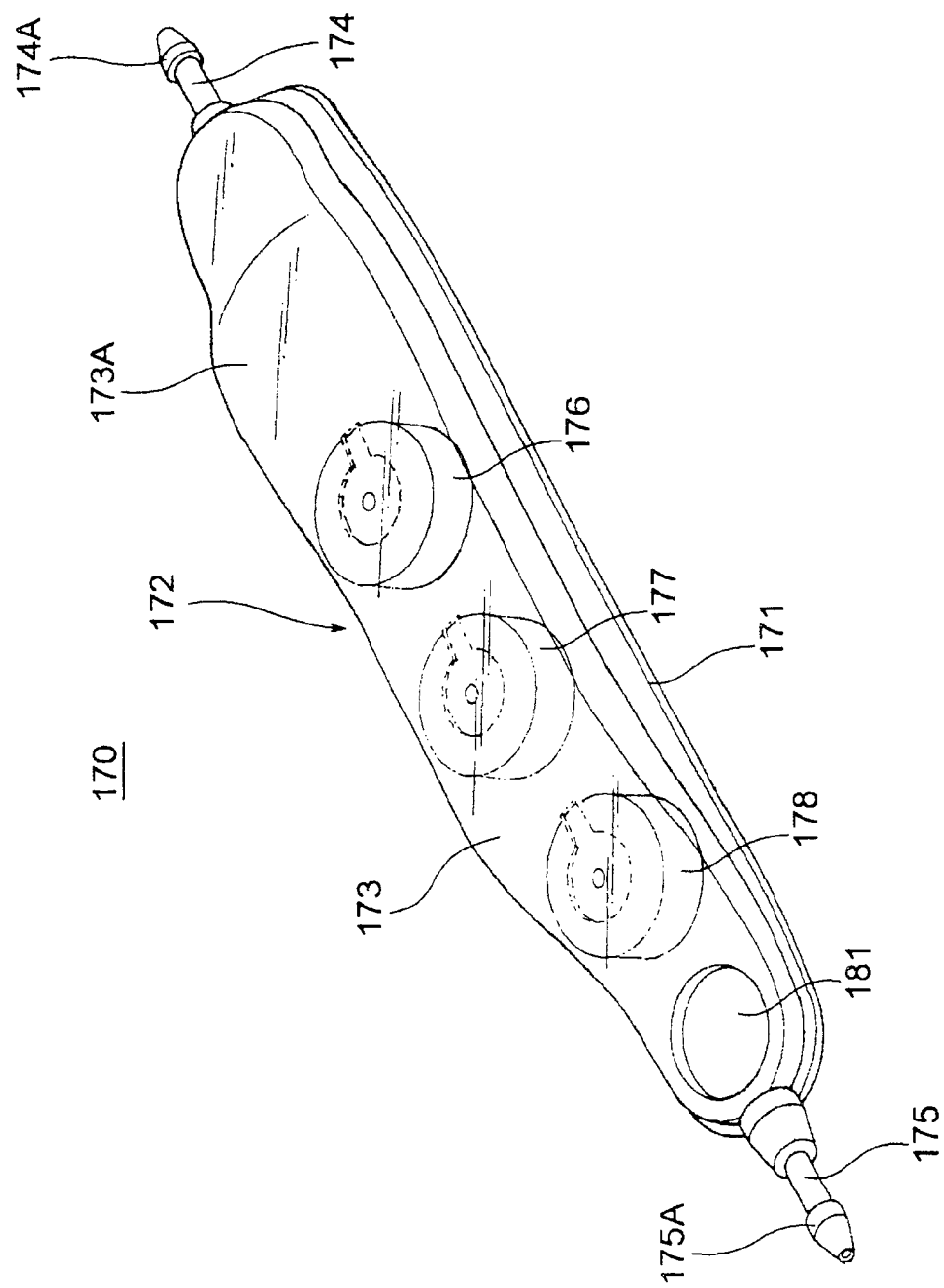
FIG. 31 is an overall perspective view of a shunt valve for treatment of hydrocephalus showing a fourteenth embodiment of a shunt valve for treatment of hydrocephalus according to the present invention.
Figure 32:
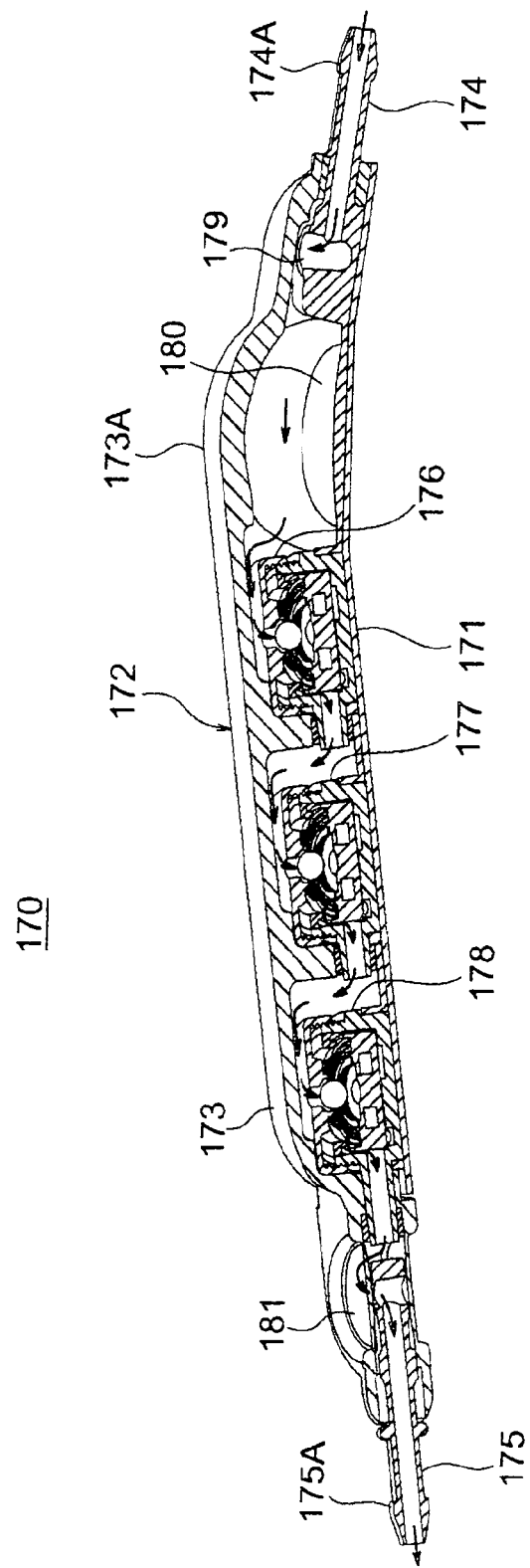
FIG. 32 is a vertical cross-sectional view of the shunt valve for treatment of hydrocephalus as illustrated in FIG. 30.

FIG. 31 and FIG. 32 show a fourteenth embodiment of a shunt valve for treatment of hydrocephalus according to the present invention.

In FIG. 31 and FIG. 32, a shunt valve for treatment of hydrocephalus 170 is formed as an integral unit and has a shunt main body 172 which is mounted to a cured plastic substrate 171, and a flexible silicone elastomer membrane 173 which covers the entire device.

The fourteenth embodiment of a shunt valve for treatment of hydrocephalus according to the present invention as illustrated in FIG. 31 and FIG. 32 differs from the fifth embodiment of the shunt valve for treatment of hydrocephalus according to the present invention as illustrated in FIG. 14 and FIG. 15 in that the fifth embodiment of the shunt valve for treatment of hydrocephalus according to the invention as illustrated in FIG. 14 and FIG. 15 employs twin devices which are first valve pressure variable device 65 and second valve pressure variable device 66, whereas the fourteenth embodiment of a shunt valve for treatment of hydrocephalus according to the present invention as illustrated in FIG. 31 and FIG. 32 employs triple devices which are: a first valve pressure variable device 176, a second valve pressure variable device 177 and a third valve pressure variable device 178.

There are no other differences with the fifth embodiment of the shunt valve for treatment of hydrocephalus according to the present invention as illustrated in FIG. 14 and FIG. 15.

In FIG. 31 and FIG. 32, 174 denotes an inflow connector having a cylindrical shape and connecting the rear end of a ventricular catheter having a needle for tapping inside the ventricle attached to a leading end thereof, and 174A denotes a protrusion formed at the leading end of the inflow connector 174 and projecting to the outside. In FIG. 31 and FIG. 32, 175 denotes an outflow connector having a cylindrical shape and connecting the rear end of a peritoneal catheter inserted in the peritoneal cavity, and 175A denotes a protrusion formed at the leading end of the outflow connector 175 and projecting to the outside.

In FIG. 31 and FIG. 32, 176 denotes a first valve pressure variable device, 177 denotes a second valve pressure variable device, 178 denotes a third valve pressure variable device, 179 denotes a ventricle-side occluder, 180 denotes a reservoir and 181 denotes a chamber.

Inflow connector 174 is mounted at the cerebrospinal fluid inflow side of the first valve pressure variable device 176. A ventricular catheter is connected to the inflow connector 174 and a peritoneal catheter is connected to the outflow connector 175.

The inflow connector 174 has a similar configuration with the inflow connector 64 of the fifth embodiment as illustrated in FIG. 14 and FIG. 15, while the outflow connector 175 has a similar configuration with the outflow connector 68 of the fifth embodiment as illustrated in FIG. 14 and FIG. 15.

Also, the first valve pressure variable device 176 has a similar configuration to the first valve pressure variable device 75 of the sixth embodiment as illustrated in FIG. 16 and FIG. 17, while the second valve pressure variable device 177 has a similar configuration to the second valve pressure variable device 76 of the sixth embodiment as illustrated in FIG. 16 and FIG. 17, and the third valve pressure variable device 178 has a similar configuration to the second valve pressure variable device 76 of the sixth embodiment as illustrated in FIG. 16 and FIG. 17.

The ventricle-side occluder 179 has a similar configuration to the ventricle-side occluder 68 of the fifth embodiment as illustrated in FIG. 14 and FIG. 15 and is provided on the inflow side of the intraventricular cerebrospinal fluid in the inflow connector 174, serving to press-close the tract through which the cerebrospinal fluid flows, temporarily stopping the cerebrospinal fluid flow. The ventricle-side occluder 179 is formed in an opening portion at a rear end of the inflow connector 174, and is formed integrally with membrane 173 comprised of a flexible silicone elastomer (soft silicone resin), having a cylindrical shape with an open top and a bottom.

The reservoir 180 has a similar configuration to reservoir 78 of the sixth embodiment as illustrated in FIG. 16 and FIG. 17, and is formed as a chamber (open space) provided between the first valve pressure variable device 176 and the second valve pressure variable device 177 and serves to accumulate a specific amount of cerebrospinal fluid. The upper wall of the reservoir 180 is constituted of a silicone dome 173A formed by a membrane 173 raised in a dome shape and made of a flexible silicone elastomer (soft silicone resin) and when the silicone dome 173A is depressed, the fluid is forced to the outside of the reservoir 180.

Following implantation of the shunt valve for treatment of hydrocephalus 170 under the scalp and in the vicinity of the pericranium, the reservoir 180 makes it possible to harvest the cerebrospinal fluid accumulated therein and inject drug solutions such as contrast material and the like therein through a needle which is tapped from outside of the scalp into the membrane 173 forming the silicone dome 173A.

Also, chamber 181 has a similar configuration to chamber 79 of the sixth embodiment as illustrated in FIG. 16 and FIG. 17.

The chamber 181 prevents sudden outflow of the intraventricular cerebrospinal fluid and a sudden drop in the intraventricular pressure occurring when a patient suddenly stands up from a lying down position. The chamber 181 has a check valve which opens in the event the cerebrospinal fluid is forced to flow due to high intraventricular pressure, and closes when a negative pressure is created inside the peritoneal catheter to nullify the siphon effect of the cerebrospinal fluid. The chamber 181 has a cavity where the cerebrospinal fluid which normally drains out of the ventricles primarily accumulates when the valve closes due to the negative pressure.

An opening 20A of the second cover 20 is formed in the outflow tract 14B of the first valve pressure variable device 176 and will become the inflow side of the cerebrospinal fluid in the second valve pressure variable device 177 (refer to FIG. 5 and FIG. 6). An opening 20A of the second cover 20 which becomes the inflow side of the cerebrospinal fluid in the third valve pressure variable device 178 is formed in the outflow tract 25B which is the output side of the cerebrospinal fluid from the second valve pressure variable device 177 (refer to FIG. 5 and FIG. 6). Further, an outflow connector 175 is mounted in the outflow tract 25B which is the output side of the cerebrospinal fluid from the third valve pressure variable device 178.

The relationship between the intraventricular pressure and the flow rate of the cerebrospinal fluid flowing out of the ventricles following adjustment of the first valve pressure variable device 176, the second valve pressure variable device 177 and the third valve pressure variable device 178 provided in the shunt valve for treatment of hydrocephalus 170 of the fourteenth embodiment of the present invention is similar to the thirteenth embodiment of the shunt valve for treatment of hydrocephalus according to the invention as illustrated in FIG. 29 and FIG. 30.

According to the shunt valve for treatment of hydrocephalus of the fourteenth embodiment according to the present invention, as valve adjustment of the first valve pressure variable device 176 and valve adjustment of the second valve pressure variable device 177 and the third valve pressure variable device 178 can be carried out independently from one another, unlike the conventional shunt valve for treatment of hydrocephalus which can be adjusted in 5 ways, the device of the present invention can be adjusted in 125 ways, enabling even finer adjustment with respect to hydrocephalus patients.

Fifteenth Embodiment

Figure 33:
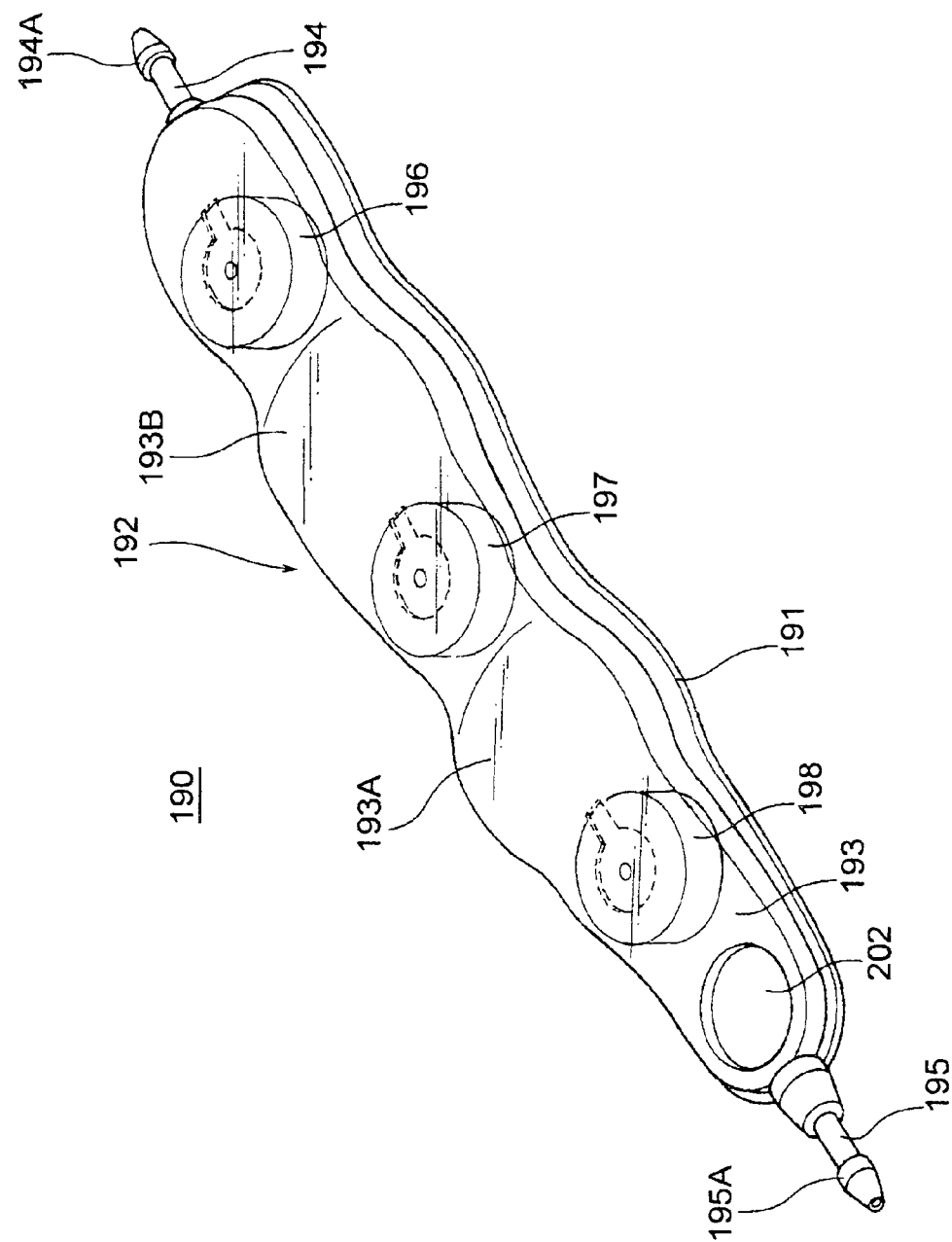
FIG. 33 is an overall perspective view of a shunt valve for treatment of hydrocephalus showing a fifteenth embodiment of a shunt valve for treatment of hydrocephalus according to the present invention.
Figure 34:
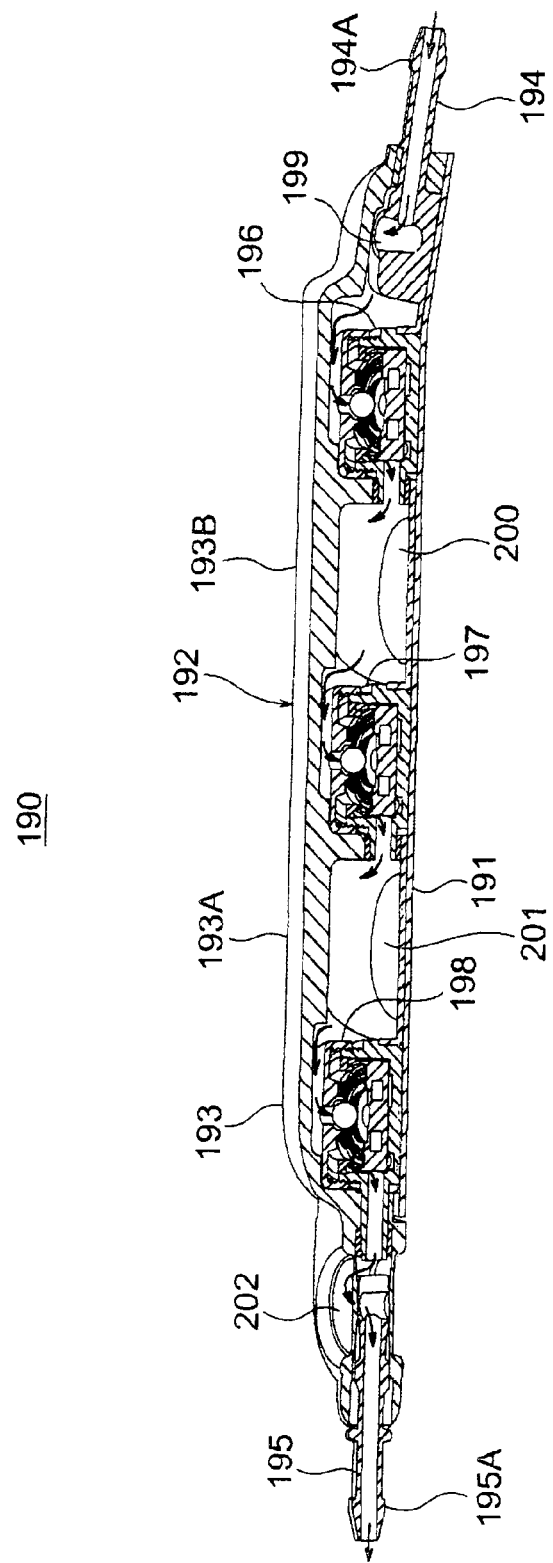
FIG. 34 is a vertical cross-sectional view of the shunt valve for treatment of hydrocephalus as illustrated in FIG. 33.

FIG. 33 and FIG. 34 show a fifteenth embodiment of a shunt valve for treatment of hydrocephalus according to the present invention.

In FIG. 33 and FIG. 34, a shunt valve for treatment of hydrocephalus 190 is formed as an integral unit and has a shunt main body 192 which is mounted to a cured plastic substrate 191, and a flexible silicone elastomer membrane 193 which covers the entire device.

The fifteenth embodiment of a shunt valve for treatment of hydrocephalus according to the present invention as illustrated in FIG. 33 and FIG. 34 differs from the fourteenth embodiment of the shunt valve for treatment of hydrocephalus according to the present invention as illustrated in FIG. 31 and FIG. 32 in that unlike the fourteenth embodiment of the shunt valve for treatment of hydrocephalus according to the invention as illustrated in FIG. 31 and FIG. 32 wherein the reservoir 180 is provided between the inflow connector 174 and the first valve pressure variable device 176, in the fifteenth embodiment of a shunt valve for treatment of hydrocephalus according to the present invention as illustrated in FIG. 33 and FIG. 34, the reservoir is not provided between the first valve pressure variable device 196 and the inflow connector 194, but instead, a first reservoir 200 is provided between the first valve pressure variable device 196 and the second valve pressure variable device 197 and a first reservoir 201 is provided between the second valve pressure variable device 197 and a third valve pressure variable device 198.

There are no other differences with the configuration of the fourteenth embodiment of a shunt valve for treatment of hydrocephalus according to the present invention as illustrated in FIG. 31 and FIG. 32.

In FIG. 33 and FIG. 34, 194 denotes an inflow connector having a cylindrical shape and connecting the rear end of a ventricular catheter having a needle for tapping inside the ventricle attached to a leading end thereof, and 194A denotes a protrusion formed at the leading end of the inflow connector 194 and projecting to the outside. In FIG. 33 and FIG. 34, 195 denotes an outflow connector having a cylindrical shape and connecting a rear end of a peritoneal catheter inserted in the peritoneal cavity, and 195A denotes a protrusion formed at the leading end of the outflow connector 195 and projecting to the outside.

In FIG. 33 and FIG. 34, 196 denotes a first valve pressure variable device, 197 denotes a second valve pressure variable device, 198 denotes a third valve pressure variable device, 199 denotes a ventricle-side occluder, 200 and 201 denote a first and a second reservoir, respectively and 202 denotes a chamber.

Inflow connector 194 is mounted at the cerebrospinal fluid inflow side of the first valve pressure variable device 196. A ventricular catheter is connected to the inflow connector 194 and a peritoneal catheter is connected to the outflow connector 195.

The inflow connector 194 has a similar configuration with the inflow connector 174 of the fourteenth embodiment as illustrated in FIG. 31 and FIG. 32, while outflow connector 195 has a similar configuration with the outflow connector 175 of the fourteenth embodiment as illustrated in FIG. 31 and FIG. 32.

Also, the first valve pressure variable device 196 has a similar configuration to the first valve pressure variable device 176 of the fourteenth embodiment as illustrated in FIG. 31 and FIG. 32, while the second valve pressure variable device 197 has a similar configuration to the second valve pressure variable device 177 of the fourteenth embodiment as illustrated in FIG. 31 and FIG. 32, and the third valve pressure variable device 198 has a similar configuration to the third valve pressure variable device 178 of the fourteenth embodiment as illustrated in FIG. 31 and FIG. 32.

The ventricle-side occluder 199 has a similar configuration to the ventricle-side occluder 179 of the fourteenth embodiment as illustrated in FIG. 31 and FIG. 32 and is provided on the inflow side of the intraventricular cerebrospinal fluid in the inflow connector 194, serving to press-close the tract through which the cerebrospinal fluid flows, temporarily stopping the cerebrospinal fluid flow. The ventricle-side occluder 199 is formed in an opening portion at the rear end of the inflow connector 194, and is formed integral with a membrane 193 comprised of a flexible silicone elastomer (soft silicone resin), having a cylindrical shape with an open top and a bottom.

The first and second reservoirs 200 and 201 have a similar configuration to reservoir 180 of the fourteenth embodiment as illustrated in FIG. 31 and FIG. 32, the first reservoir 200 being formed as a chamber (open space) provided between the first valve pressure variable device 196 and the second valve pressure variable device 197 and serves to accumulate a specific amount of cerebrospinal fluid. Similarly, the second reservoir 201 is formed as a chamber (open space) provided between the second valve pressure variable device 197 and the third valve pressure variable device 198 and serves to accumulate a specific amount of cerebrospinal fluid.

The upper wall of the first and second reservoirs 200 and 201 is constituted of a silicone dome 193A and 193B formed by a membrane 193 raised in a dome shape and made of a flexible silicone elastomer (soft silicone resin) and when the silicone domes 193A and 193B are depressed, the cerebrospinal fluid is forced to the outside of the first and second reservoirs 200 and 201.

Following implantation of the shunt valve for treatment of hydrocephalus 190 under the scalp and in the vicinity of the pericranium, the first and second reservoirs 200 and 201 make it possible to harvest the cerebrospinal fluid accumulated therein and to inject drug solutions such as contrast material and the like therein through a needle which is tapped from outside of the scalp into the membrane 193 forming the silicone domes 193A and 193B.

Also, the chamber 202 has a similar configuration with the chamber 181 of the fourteenth embodiment as illustrated in FIG. 31 and FIG. 32.

The chamber 202 prevents sudden outflow of the intraventricular cerebrospinal fluid and a sudden drop in the intraventricular pressure occurring when a patient suddenly stands up from a lying down position. The chamber 202 has a check valve which opens in the event the cerebrospinal fluid is forced to flow due to high intraventricular pressure, and closes when a negative pressure is created inside the peritoneal catheter to nullify the siphon effect of the cerebrospinal fluid. The chamber 202 has a cavity where the cerebrospinal fluid which normally drains out of the ventricles primarily accumulates when the valve closes due to the negative pressure.

The opening 20A of the second cover 20 is formed in the outflow tract 14B of the first valve pressure variable device 196 and will become the inflow side of the cerebrospinal fluid in the second valve pressure variable device 197 on the outflow side of the cerebrospinal fluid in the first reservoir 200 (refer to FIG. 5 and FIG. 6). The opening 20A of the second cover 20 which becomes the inflow side of the cerebrospinal fluid in the third valve pressure variable device 198 is formed in the outflow tract 25B which is the output side of the cerebrospinal fluid from the second valve pressure variable device 197, on the output side of the cerebrospinal fluid from the second reservoir 201 (refer to FIG. 5 and FIG. 6).

Further, an outflow connector 195 is mounted in an outflow tract 25B which is the output side of the cerebrospinal fluid from the third valve pressure variable device 198.

The relationship between the intraventricular pressure and the flow rate of the cerebrospinal fluid flowing out of the ventricles following adjustment of the first valve pressure variable device 196, the second valve pressure variable device 197 and the third valve pressure variable device 198 provided in the shunt valve for treatment of hydrocephalus 190 of the fifteenth embodiment of the present invention is similar to the fourteenth embodiment of the shunt valve for treatment of hydrocephalus according to the present invention as illustrated in FIG. 31 and FIG. 32.

According to the shunt valve for treatment of hydrocephalus of the fifteenth embodiment according to the present invention, as valve adjustment of the first valve pressure variable device 196 and valve adjustment of the second valve pressure variable device 197 and the third valve pressure variable device 198 can be carried out independently from one another, unlike the conventional shunt valve for treatment of hydrocephalus which can be adjusted in 5 ways, the device of the present invention can be adjusted in 125 ways, enabling even finer adjustment with respect to hydrocephalus patients.

Furthermore, as the first reservoir 200 and the second reservoir 201 are independently provided between the first valve pressure variable device 196 and the second valve pressure variable device 197, and the second valve pressure variable device 197 and the third valve pressure variable device 198, respectively, clogging of any of the first valve pressure variable device 196, the second valve pressure variable device 197 and the third valve pressure variable device 198 can be independently dealt with.

Sixteenth Embodiment

Figure 35:
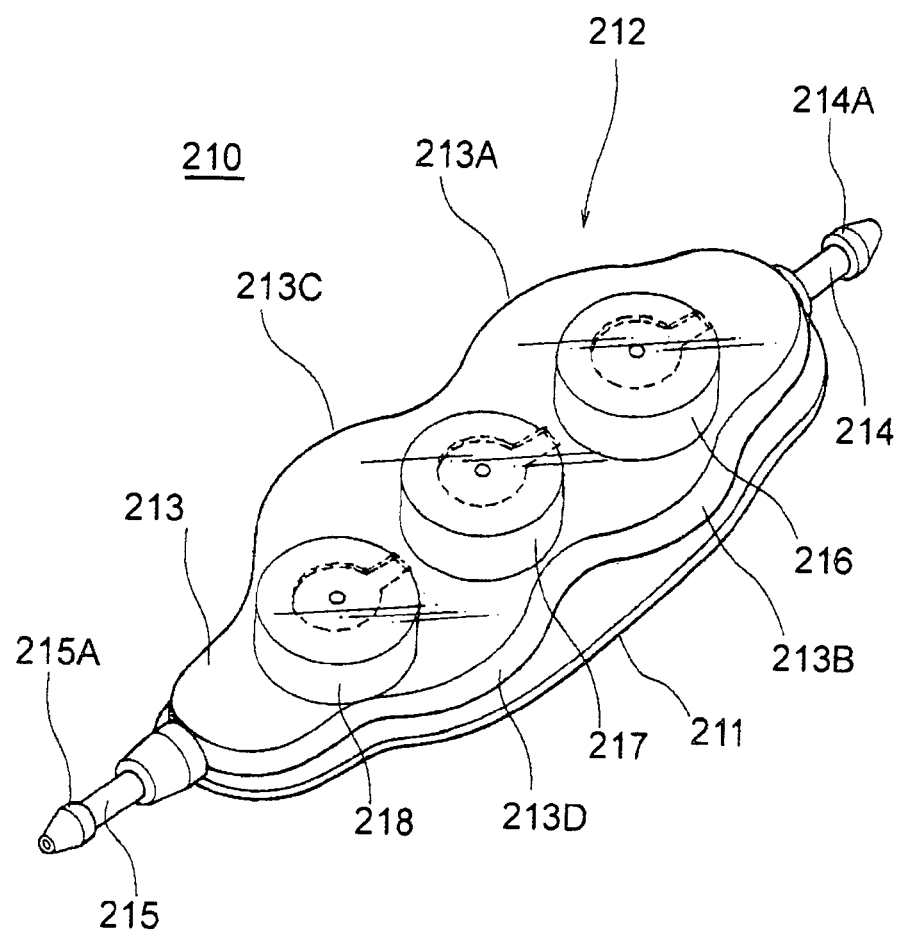
FIG. 35 is an overall perspective view of a shunt valve for treatment of hydrocephalus showing a sixteenth embodiment of a shunt valve for treatment of hydrocephalus according to the present invention.
Figure 36:
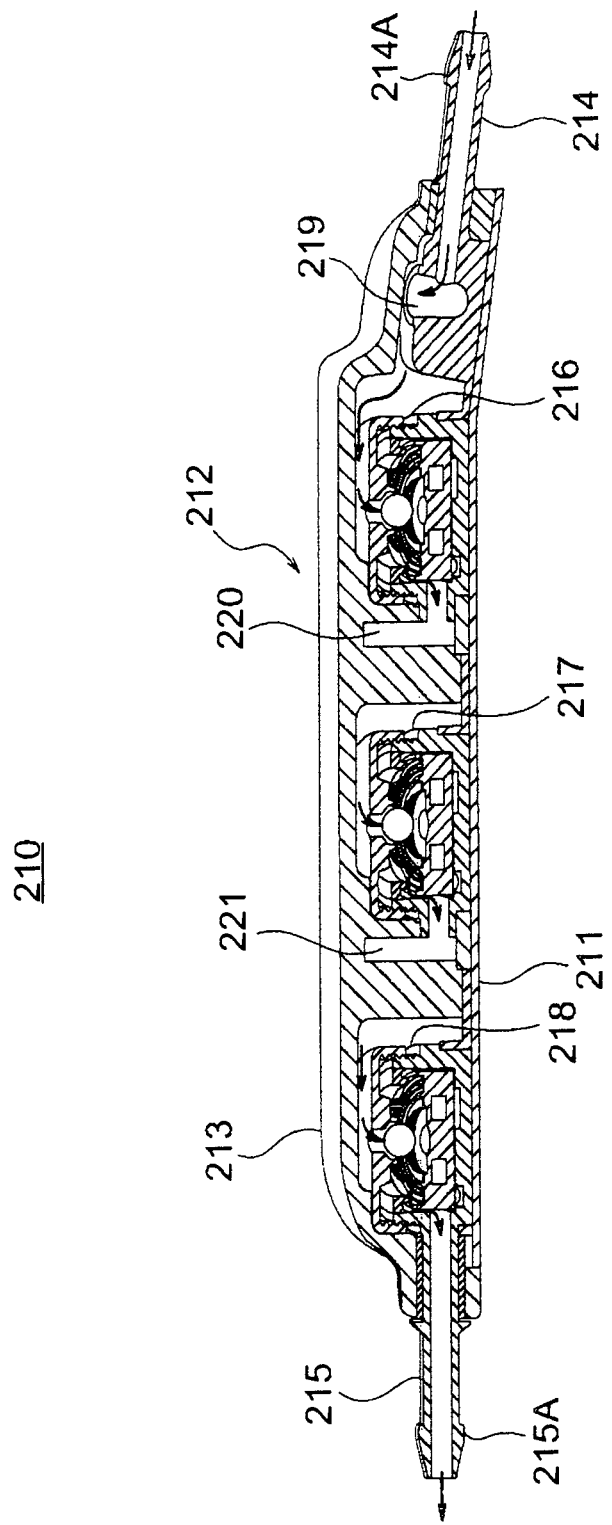
FIG. 36 is a vertical cross-sectional view of the shunt valve for treatment of hydrocephalus as illustrated in FIG. 35.
Figure 37:
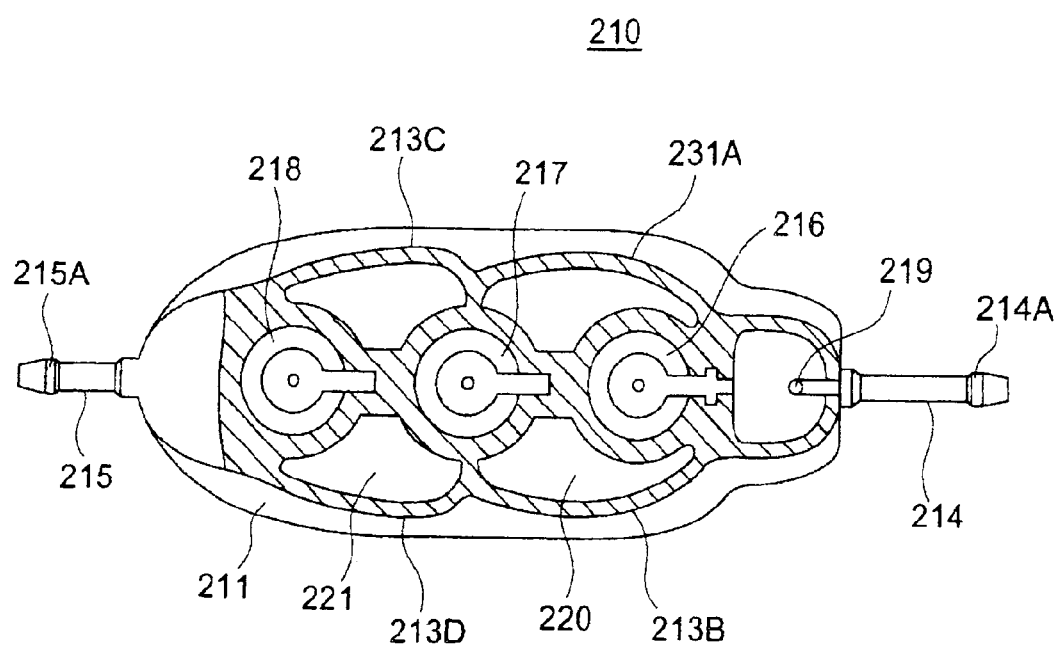
FIG. 37 is a horizontal cross-sectional view of the shunt valve for treatment of hydrocephalus as illustrated in FIG. 35.

FIG. 35 through FIG. 37 show a sixteenth embodiment of a shunt valve for treatment of hydrocephalus according to the present invention.

In FIG. 35 through FIG. 37, a shunt valve for treatment of hydrocephalus 210 is formed as an integral unit and has a shunt main body 212 which is mounted to a cured plastic substrate 211, and a flexible silicone elastomer membrane 213 which covers the entire device.

The sixteenth embodiment of a shunt valve for treatment of hydrocephalus according to the present invention as illustrated in FIG. 35 through FIG. 37 differs from the fifteenth embodiment of the shunt valve for treatment of hydrocephalus according to the present invention as illustrated in FIG. 33 and FIG. 34 as follows.

Specifically, in the fifteenth embodiment of the shunt valve for treatment of hydrocephalus according to the present invention as illustrated in FIG. 33 and FIG. 34, the first reservoir 200 is provided between the first valve pressure variable device 196 and the second valve pressure variable device 197, with an upper wall thereof forming a silicone dome 193B, made of a membrane 193 raised in a dome shape and made of a flexible silicone elastomer (soft silicone resin) and the second reservoir 201 is provided between the second valve pressure variable device 197 and the third valve pressure variable device 198, with an upper wall thereof forming a silicone dome 193A, made of a membrane 193 raised in a dome shape and made of a flexible silicone elastomer (soft silicone resin).

In contrast to this, in the sixteenth embodiment of the shunt valve for treatment of hydrocephalus according to the present invention as illustrated in FIG. 35 through FIG. 37, a first reservoir 220 which supplies the cerebrospinal fluid flowing from the inflow connector 214 into the shunt main body 212 directly inside the first valve main body 10 through opening 9A in the first cover 9 of the first valve pressure variable device 216 is provided between the outflow tract 14B of the first valve pressure variable device 216 and the second valve pressure variable device 217, adjacent the side surface of the first valve pressure variable device 216 and the side surface of the second valve pressure variable device 217 on both sides in a longitudinal direction of the shunt main body 212 and stretching over in a longitudinal direction of the shunt main body 212 and is constituted of first silicone side domes 213A and 213B formed of a membrane 213 bulging out in a dome shape on both sides in a longitudinal direction of the shunt main body 212 and made of a flexible silicone elastomer (soft silicone resin). Also, in the sixteenth embodiment of the shunt valve for treatment of hydrocephalus according to the present invention as illustrated in FIG. 35 through FIG. 37, a second reservoir 221 is provided between the outflow tract 14B of the second valve pressure variable device 217 and the third valve pressure variable device 218, adjacent to the side surface of the second valve pressure variable device 217 and the side surface of the third valve pressure variable device 218 on both sides in a longitudinal direction of the shunt main body 212 and stretching over in a longitudinal direction of the shunt main body 212 and is constituted of second silicone side domes 213C and 213D formed of a membrane 213 bulging out in a dome shape on both sides in a longitudinal direction of the shunt main body 212 and made of a flexible silicone elastomer (soft silicone resin). Specifically, the second reservoir 221 and the first reservoir 220 are provided independently from one another.

There are no other differences with the fifteenth embodiment of the shunt valve for treatment of hydrocephalus according to the present invention as illustrated in FIG. 33 and FIG. 34.

In the fifteenth embodiment of a shunt valve for treatment of hydrocephalus according to the present invention as illustrated in FIG. 33 and FIG. 34, the first reservoir 200 is arranged between the first valve pressure variable device 196 and the second valve pressure variable device 197, and the second reservoir 201 is arranged between the second valve pressure variable device 197 and the third valve pressure variable device 198. In contrast to this, in the sixteenth embodiment of a shunt valve for treatment of hydrocephalus according to the present invention as illustrated in FIG. 35 through FIG. 37, the first reservoir 220 is provided in the reservoir space between the first valve pressure variable device 216 and the second valve pressure variable device 217, adjacent to the side surface of the first valve pressure variable device 216 and the side surface of the second valve pressure variable device 217 and stretching over in a longitudinal direction of the shunt main body and is constituted of two first silicone side domes formed of a flexible silicone elastomer membrane bulging out in a dome shape on both sides in a longitudinal direction of the shunt main body, and also, the second reservoir 221 is provided in the reservoir space between the second valve pressure variable device 217 and the third valve pressure variable device 218, adjacent to the side surface of the second valve pressure variable device 217 and the side surface of the third valve pressure variable device 218 and stretching over in a longitudinal direction of the shunt main body and is constituted of two first silicone side domes formed of a flexible silicone elastomer membrane bulging out in a dome shape on both sides in a longitudinal direction of the shunt main body.

In FIG. 35 through FIG. 37, 214 denotes an inflow connector having a cylindrical shape and connecting the rear end of a ventricular catheter having a needle for tapping inside the ventricle attached to a leading end thereof, and 214A denotes a protrusion formed at the leading end of the inflow connector 214 and projecting to the outside. In FIG. 35 through FIG. 37, 215 denotes an outflow connector having a cylindrical shape and connecting the rear end of a peritoneal catheter inserted in the peritoneal cavity, and 215A denotes a protrusion formed at the leading end of the outflow connector 215 and projecting to the outside.

In FIG. 35 through FIG. 37, 216 denotes a first valve pressure variable device, 217 denotes a second valve pressure variable device, 218 denotes a third valve pressure variable device, 219 denotes a ventricular occluder and 220 and 221 denote a first and a second reservoir.

The inflow connector 214 is provided on the cerebrospinal fluid inflow side of the first valve pressure variable device 216. A ventricular catheter is connected to the inflow connector 214 and a peritoneal catheter is connected to the outflow connector 215.

The inflow connector 214 has a similar configuration with the inflow connector 194 of the fifteenth embodiment as illustrated in FIG. 33 and FIG. 34, and the outflow connector 215 has a similar configuration with the outflow connector 195 of the fifteenth embodiment as illustrated in FIG. 34 and FIG. 35.

The first valve pressure variable device 216 has a similar configuration with the first valve pressure variable device 196 of the fifteenth embodiment as illustrated in FIG. 33 and FIG. 34, the second valve pressure variable device 217 has a similar configuration with the second valve pressure variable device 197 of the fifteenth embodiment as illustrated in FIG. 33 and FIG. 34 and the third valve pressure variable device 218 has a similar configuration with the third valve pressure variable device 198 of the fifteenth embodiment as illustrated in FIG. 33 and FIG. 34.

The ventricle-side occluder 219 has a similar configuration with the ventricle-side occluder 199 of the fifteenth embodiment as illustrated in FIG. 33 and FIG. 34, and is provided on the inflow side of the intraventricular cerebrospinal fluid in the inflow connector 214, serving to press-close the tract through which the cerebrospinal fluid flows, temporarily stopping the cerebrospinal fluid flow. The ventricle-side occluder 219 is formed in an opening portion at a rear end of the inflow connector 214, and is formed integral with a membrane 213 comprised of a flexible silicone elastomer (soft silicone resin), having a cylindrical shape with an open top and a bottom.

The first and the second reservoirs 220 and 221 have a similar configuration with the reservoir 180 in the fifteenth embodiment as illustrated in FIG. 33 and FIG. 34. The first reservoir 220 is formed as a chamber (cavity) for accumulating a specific amount of cerebrospinal fluid and is provided over the first valve pressure variable device 216 and the second valve pressure variable device 217. Also, the second reservoir 221 is formed as a chamber (cavity) for accumulating a specific amount of cerebrospinal fluid and is provided over the second valve pressure variable device 217 and the third valve pressure variable device 218.

The upper wall of the first reservoir 220 and the side walls in a longitudinal direction of the shunt main body 212 are formed as the first silicone side domes 213A and 213B on both sides in a longitudinal direction of the shunt main body, with the domes being made of a flexible silicone elastomer membrane 213 (soft silicone resin) raised in a dome shape and at the same time bulging out on both sides in a longitudinal direction of the shunt main body 212. When the first silicone side domes 213A and 213B are depressed, the cerebrospinal fluid is forced out of the first reservoir 200 into the first valve pressure variable device 216 and the second valve pressure variable device 217 connected thereto.

The upper wall of the second reservoir 221 and the side walls in a longitudinal direction of the shunt main body 212 are formed as second silicone side domes 213C and 213D on both sides in a longitudinal direction of the shunt main body 212, with the domes being made of a flexible silicone elastomer membrane 213 (soft silicone resin) raised in a dome shape and at the same time bulging out on both sides in a longitudinal direction of the shunt main body 212. When the second silicone side domes 213C and 213D are depressed, the cerebrospinal fluid is forced out of the second reservoir 221 into the second valve pressure variable device 217 and the second valve pressure variable device 218 connected thereto.

Following implantation of the shunt valve for treatment of hydrocephalus 210 under the scalp and in the vicinity of the pericranium, the first and second server 220 and 221 make it possible to harvest the cerebrospinal fluid accumulated therein and inject drug solutions such as contrast material and the like therein through a needle which is tapped from outside of the scalp into the membrane 213 forming the first and second silicone side domes 213A, 213B, 213C and 213D.

The opening 20A of the second cover 20 is formed in the outflow tract 14B of the first valve pressure variable device 216 and will become the inflow side of the cerebrospinal fluid in the second pressure variable device 217 on the cerebrospinal fluid outflow side of the first reservoir 220 (refer to FIG. 5 and FIG. 6). The opening 20A of the second cover 20 which becomes the inflow side of the cerebrospinal fluid in the third valve pressure variable device 218 is formed in the outflow tract 25B which is the output side of the cerebrospinal fluid from the second valve pressure variable device 217 in the cerebrospinal fluid outflow side of the second reservoir 221 (refer to FIG. 5 and FIG. 6).

Further, an outflow connector 215 is mounted in an outflow tract 25B which is the output side of the cerebrospinal fluid from the third valve pressure variable device 218.

The relationship between the intraventricular pressure and the flow rate of the cerebrospinal fluid flowing out of the ventricles following adjustment of the first valve pressure variable device 216, the second valve pressure variable device 217 and the third valve pressure variable device 218 provided in the shunt valve for treatment of hydrocephalus 210 of the sixteenth embodiment of the present invention is similar to the fifteenth embodiment of the shunt valve for treatment of hydrocephalus according to the present invention as illustrated in FIG. 33 and FIG. 34.

According to the shunt valve for treatment of hydrocephalus of the sixteenth embodiment according to the present invention, as valve adjustment of the first valve pressure variable device 216 and valve adjustment of the second valve pressure variable device 217 and the third valve pressure variable device 218 can be carried out independently from one another, unlike the conventional shunt valve for treatment of hydrocephalus which can be adjusted in 5 ways, the device of the present invention can be adjusted in 125 ways, enabling even finer adjustment with respect to hydrocephalus patients.

Furthermore, as the first reservoir 220 is provided between the first valve pressure variable device 216 and the second valve pressure variable device 217 independently from the second reservoir 221 which is provided between the second valve pressure variable device 217 and the third valve pressure variable device 218, clogging of any of the first valve pressure variable device 216, the second valve pressure variable device 217 and the third valve pressure variable device 218 can be independently dealt with.

Seventeenth Embodiment

Figure 38:
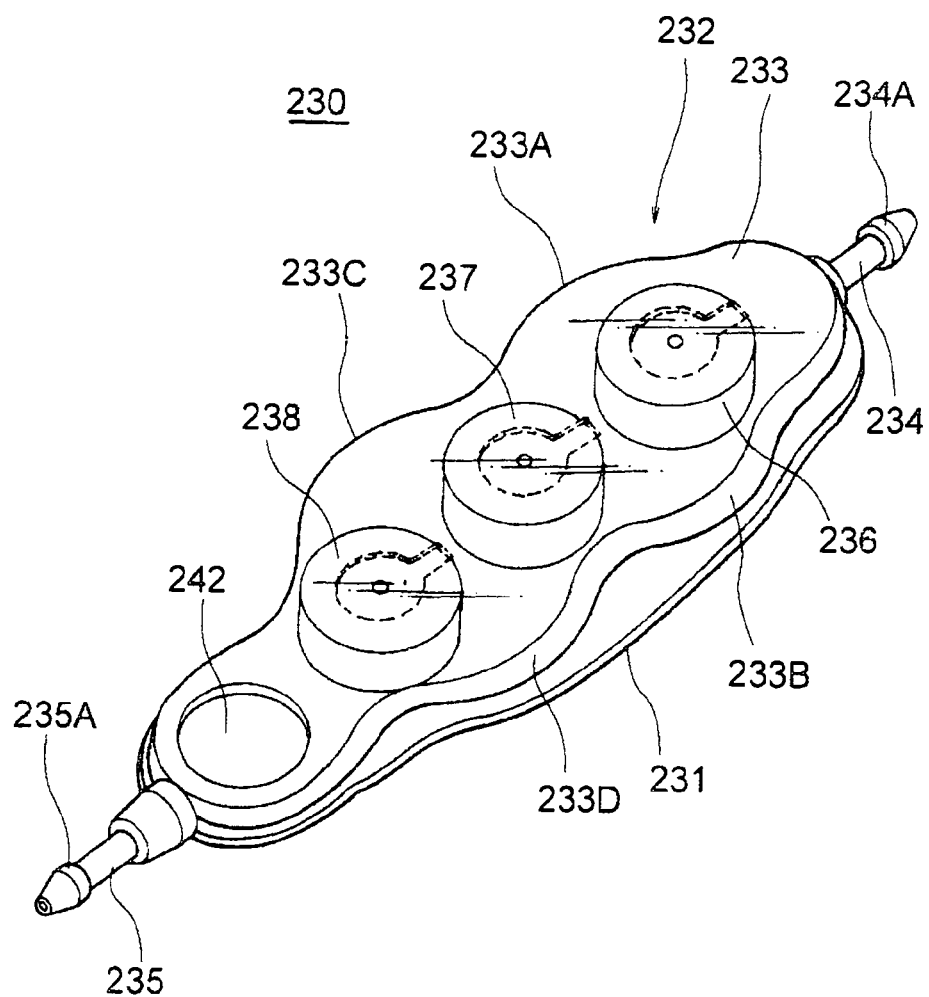
FIG. 38 is an overall perspective view of a shunt valve for treatment of hydrocephalus showing a seventeenth embodiment of a shunt valve for treatment of hydrocephalus according to the present invention.
Figure 39:
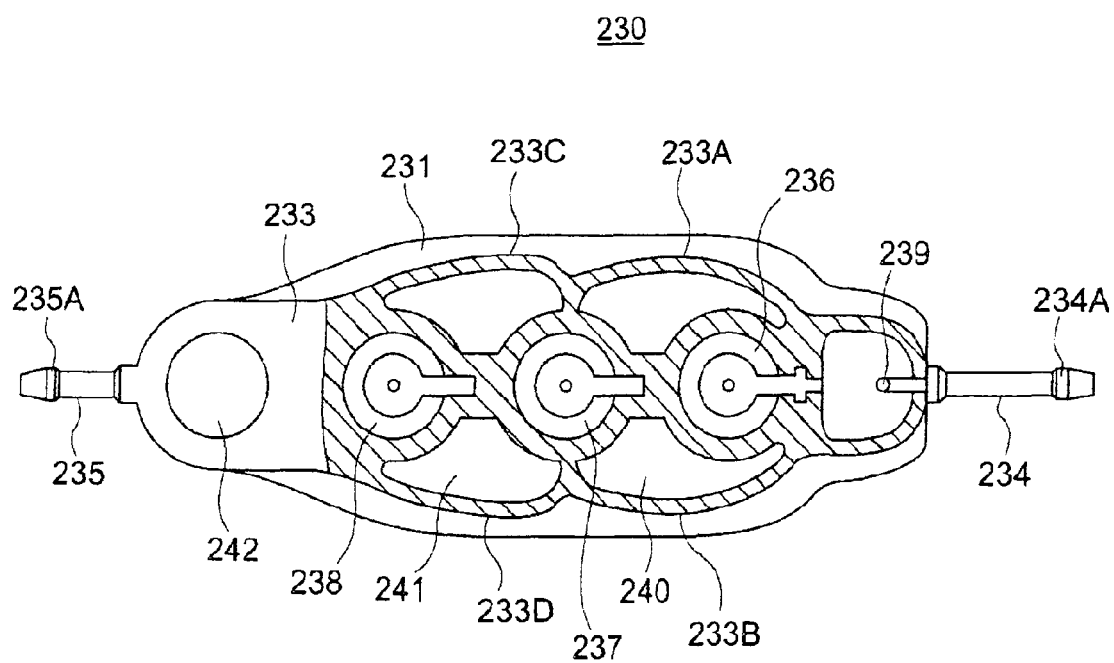
FIG. 39 is a horizontal cross-sectional view of the shunt valve for treatment of hydrocephalus as illustrated in FIG. 38.
Figure 40:
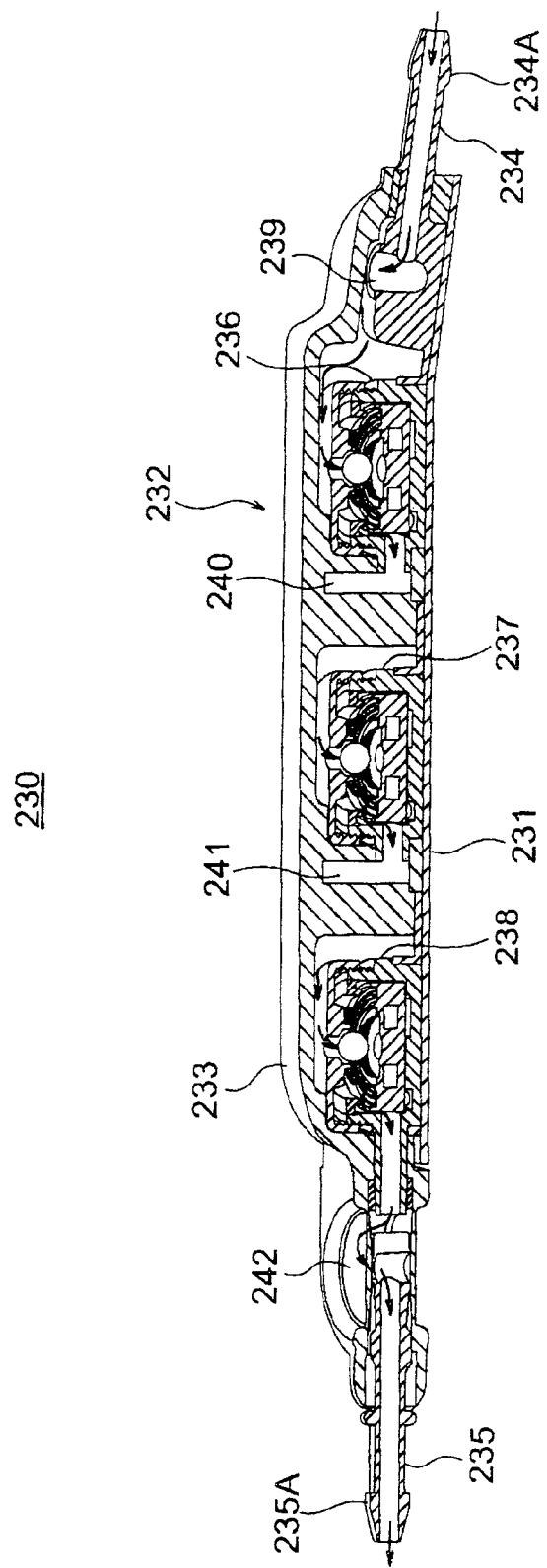
FIG. 40 is a vertical cross-sectional view of the shunt valve for treatment of hydrocephalus as illustrated in FIG. 38.

FIG. 38 through FIG. 40 show a seventeenth embodiment of a shunt valve for treatment of hydrocephalus according to the present invention.

In FIG. 38 through FIG. 40, a shunt valve for treatment of hydrocephalus 230 is formed as an integral unit and has a shunt main body 232 which is mounted to a cured plastic substrate 231, and a flexible silicone elastomer membrane 233 which covers the entire device.

The seventeenth embodiment of a shunt valve for treatment of hydrocephalus according to the present invention as illustrated in FIG. 38 through FIG. 40 differs from the sixteenth embodiment of the shunt valve for treatment of hydrocephalus according to the present invention as illustrated in FIG. 35 through FIG. 37 in that unlike the sixteenth embodiment of the shunt valve for treatment of hydrocephalus according to the present invention as illustrated in FIG. 35 through FIG. 37 where the outflow connector 235 is mounted in the outflow tract 25B which is the cerebrospinal fluid outflow side of the third valve pressure variable device 238, in the seventeenth embodiment of a shunt valve for treatment of hydrocephalus according to the present invention as illustrated in FIG. 38 through FIG. 40, a chamber 242 is provided in the outflow tract 25B which is the cerebrospinal fluid output side of the third valve pressure variable device 238 and an outflow connector 235 is provided on the cerebrospinal fluid output side of chamber 242.

There are no other differences with the sixteenth embodiment of the shunt valve for treatment of hydrocephalus according to the present invention as illustrated in FIG. 35 through FIG. 37.

Thus, the seventeenth embodiment of the shunt valve for treatment of hydrocephalus according to the present invention as illustrated in FIG. 38 through FIG. 40 is characterized in that a chamber 242 is provided between the third valve pressure variable device 198 and the outflow connector 215 of the sixteenth embodiment of the shunt valve for treatment of hydrocephalus according to the present invention as illustrated in FIG. 35 through FIG. 37.

In FIG. 38 through FIG. 40, 234 denotes an inflow connector having a cylindrical shape and connecting the rear end of a ventricular catheter having a needle for tapping inside the ventricle attached to a leading end thereof, and 234A denotes a protrusion formed at the leading end of the inflow connector 234 and projecting to the outside. In FIG. 38 through FIG. 40, 235 denotes an outflow connector having a cylindrical shape and connecting the rear end of a peritoneal catheter inserted in the peritoneal cavity, and 235A denotes a protrusion formed at a leading end of the outflow connector 235 and projecting to the outside.

In FIG. 38 through FIG. 40, 236 denotes a first valve pressure variable device, 237 denotes a second valve pressure variable device, 238 denotes a third valve pressure variable device, 239 denotes a ventricle-side occluder, 240 and 241 denote a first and a second reservoir and 242 denotes a chamber.

An inflow connector 234 is mounted to the cerebrospinal fluid inflow side of the first valve pressure variable device 236. A ventricular catheter is connected to this inflow connector 234 and a peritoneal catheter is connected to the outflow connector 235.

The inflow connector 234 has a similar configuration with the inflow connector 194 of the sixteenth embodiment as illustrated in FIG. 35 through FIG. 37, and the outflow connector 235 has a similar configuration with the outflow connector 195 of the sixteenth embodiment as illustrated in FIG. 35 through FIG. 37.

The first valve pressure variable device 236 has a similar configuration with the first valve pressure variable device 196 of the sixteenth embodiment as illustrated in FIG. 35 through FIG. 37, the second valve pressure variable device 237 has a similar configuration with the second valve pressure variable device 197 of the sixteenth embodiment as illustrated in FIG. 35 through FIG. 37, and the third valve pressure variable device 238 has a similar configuration with the third valve pressure variable device 198 of the sixteenth embodiment as illustrated in FIG. 35 through FIG. 37.

The ventricle-side occluder 239 has a similar configuration with the ventricle-side occluder 199 of the sixteenth embodiment as illustrated in FIG. 35 through FIG. 37 and is provided on the inflow side of the intraventricular cerebrospinal fluid in the inflow connector 234, serving to press-close the tract through which the cerebrospinal fluid flows, temporarily stopping the cerebrospinal fluid flow. The ventricle-side occluder 239 is formed in the opening portion at the rear end of the inflow connector 234, and is formed integral with membrane 233 comprised of a flexible silicone elastomer (soft silicone resin), having a cylindrical shape with an open top and a bottom.

The first and the second reservoirs 240 and 241 have a similar configuration to the first and second reservoirs 220 and 221 of the sixteenth embodiment as illustrated in FIG. 35 through FIG. 37, and the first reservoir 240 is formed as a chamber (open space) provided over the first valve pressure variable device 236 and the second valve pressure variable device 237 and serves to accumulate a specific amount of cerebrospinal fluid. The second reservoir 241 is formed as a chamber (open space) provided over the second valve pressure variable device 237 and the third valve pressure variable device 238 and serves to accumulate a specific amount of cerebrospinal fluid.

The upper wall of the first reservoir 240 and the side wall in a longitudinal direction of the shunt main body 232 are constituted of first silicone side dome 233A and 233B formed of a flexible silicone elastomer (soft silicone resin) membrane 233 raised in a dome shape and bulging out on both sides in a longitudinal direction of the shunt main body 232, on both sides in a longitudinal direction of the shunt main body. When the first silicone side domes 233A and 233B are depressed, the cerebrospinal fluid is forced out of the first reservoir 240 into the first valve pressure variable device 236 and the second valve pressure variable device 237 connected thereto.

The upper wall of the second reservoir 241 and the side wall in a longitudinal direction of the shunt main body 232 are constituted of second silicone side domes 233C and 233D formed by a flexible silicone elastomer (soft silicone resin) membrane 233 raised in a dome shape and bulging out on both sides in a longitudinal direction of the shunt main body 232, on both sides in a longitudinal direction of the shunt main body. When the second silicone side domes 233C and 233D are depressed, the cerebrospinal fluid is forced out of the second reservoir 241 into the second valve pressure variable device 237 and the second valve pressure variable device 238 connected thereto.

Then, following implantation of the shunt valve for treatment of hydrocephalus 230 under the scalp and in the vicinity of the pericranium, the first and second reservoirs 240 and 241 make it possible to harvest the cerebrospinal fluid accumulated therein and inject drug solutions such as contrast material and the like therein through a needle which is tapped from outside of the scalp into the membrane 233 forming the second silicone side domes 233A, 233B, 233C and 233D.

Also, chamber 242 has a similar configuration with chamber 181 in the fourteenth embodiment as illustrated in FIG. 31 and FIG. 32.

Chamber 242 prevents sudden outflow of the intraventricular cerebrospinal fluid and a sudden drop in the intraventricular pressure occurring when a patient suddenly stands up from a lying down position. The chamber 242 has a check valve which opens in the event the cerebrospinal fluid is forced to flow due to high intraventricular pressure, and closes when a negative pressure is created inside the peritoneal catheter to nullify the siphon effect of the cerebrospinal fluid. The chamber 242 has a cavity wherein the cerebrospinal fluid which normally drains out of the ventricles primarily accumulates when the valve closes due to the negative pressure.

The opening 20A of the second cover 20 is formed in the outflow tract 14B of the first valve pressure variable device 236 and will become the inflow side of the cerebrospinal fluid in the second valve pressure variable device 237 (refer to FIG. 5 and FIG. 6), on the cerebrospinal fluid outflow side of the first reservoir 240. The opening 20A of the second cover 20 which becomes the inflow side of the cerebrospinal fluid in the third valve pressure variable device 238 is formed in the outflow tract 25B which is the output side of the cerebrospinal fluid from the second valve pressure variable device 237, on the cerebrospinal fluid outflow side of the second reservoir 241 (refer to FIG. 5 and FIG. 6).

Chamber 242 is provided in the outflow tract 25B which is the cerebrospinal fluid output side of the third valve pressure variable device 198.

The relationship between the intraventricular pressure and the flow rate of the cerebrospinal fluid flowing out of the ventricles following adjustment of the first valve pressure variable device 236, the second valve pressure variable device 237 and the third valve pressure variable device 238 provided in the shunt valve for treatment of hydrocephalus 230 of the seventeenth embodiment of the present invention is similar to the sixteenth embodiment of the shunt valve for treatment of hydrocephalus according to the invention as illustrated in FIG. 35 and FIG. 37.

According to the shunt valve for treatment of hydrocephalus of the seventeenth embodiment according to the present invention, in addition to the operation of the fifteenth embodiment of the shunt valve for treatment of hydrocephalus according to the present invention as illustrated in FIG. 33 and FIG. 34, the occurrence of various other symptoms such as sudden headaches, sudden impaired awareness can be prevented. These symptoms occur when the patient suddenly sits up from a posture wherein intraventricular pressure is kept constant by the shunt valve for treatment of hydrocephalus and the amount of intraventricular cerebrospinal fluid decreases, leading to a sudden drop in the intraventricular pressure, which in turn causes the ventricles to become smaller and narrower, a condition known as the slit ventricle syndrome.

Eighteenth Embodiment

Figure 41:
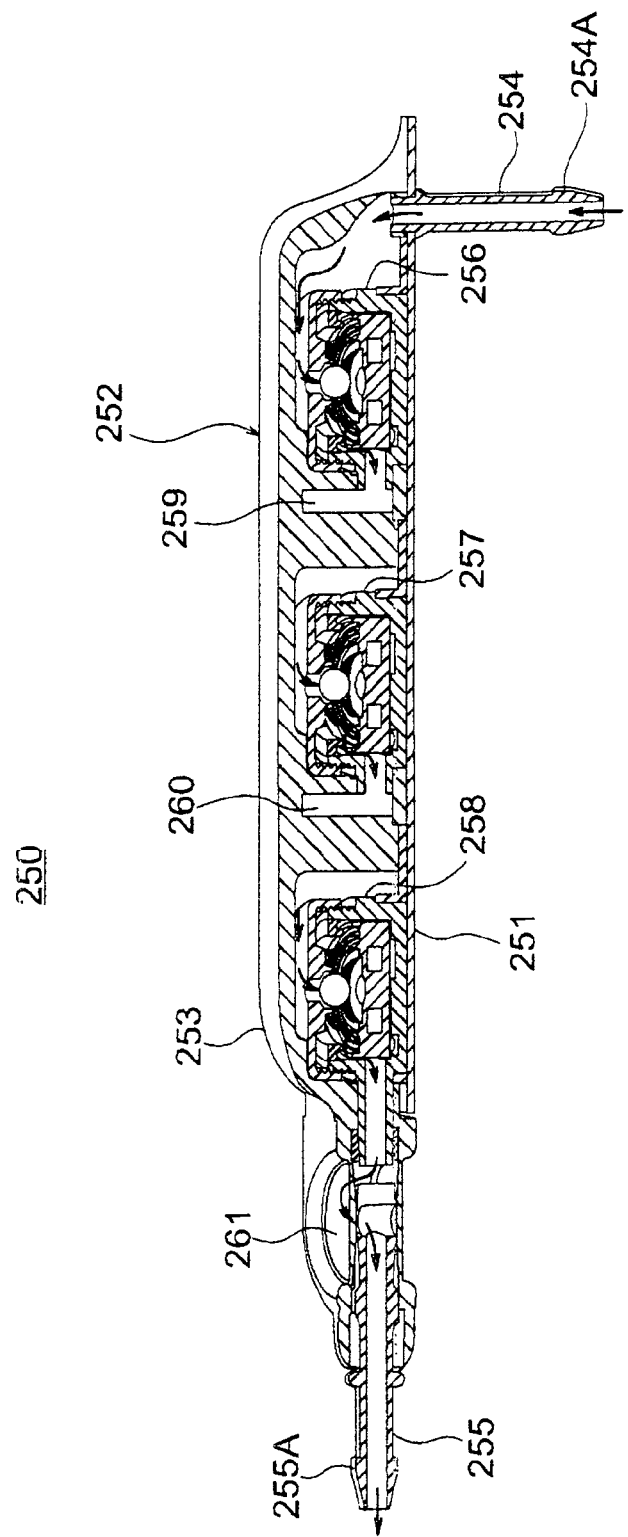
FIG. 41 is a vertical cross-sectional view of a shunt valve for treatment of hydrocephalus showing an eighteenth embodiment of a shunt valve for treatment of hydrocephalus according to the present invention.
Figure 42:
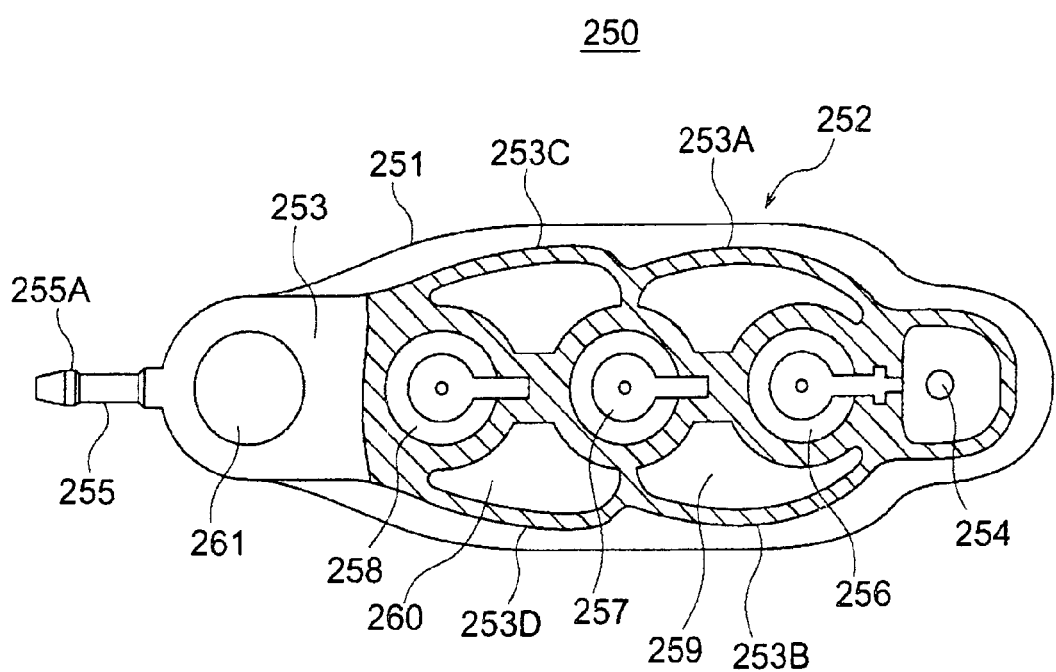
FIG. 42 is a horizontal cross-sectional view of the shunt valve for treatment of hydrocephalus as illustrated in FIG. 41.
Figure 43:
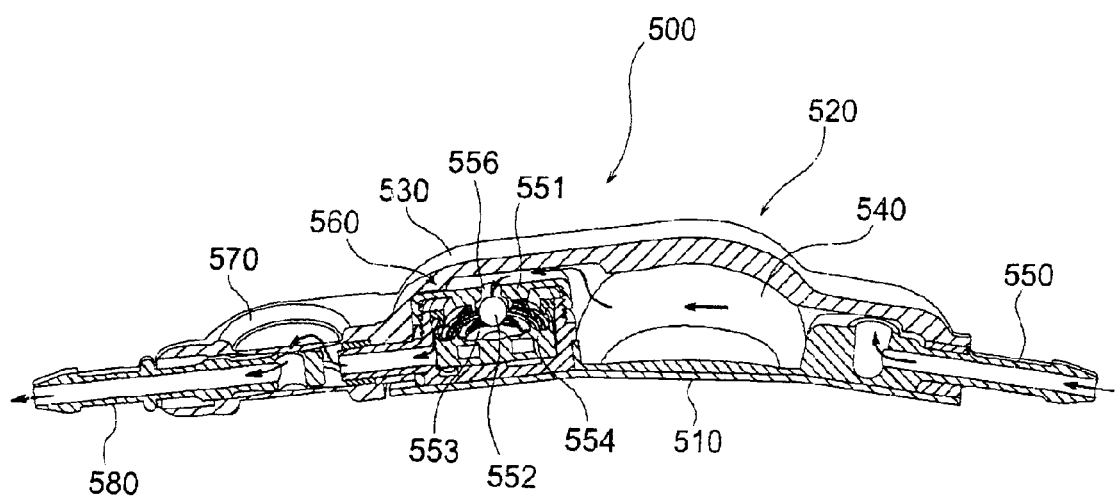
FIG. 43 is a cross-sectional plan view of a conventional shunt valve for treatment of hydrocephalus.

FIG. 41 and FIG. 42 illustrate the eighteenth embodiment of a shunt valve for treatment of hydrocephalus according to the present invention.

In FIG. 41 and FIG. 42, a shunt valve for treatment of hydrocephalus 250 is formed as an integral unit and has a shunt main body 252 which is mounted to a cured plastic substrate 251, and a flexible silicone elastomer membrane 253 which covers the entire device.

The eighteenth embodiment of a shunt valve for treatment of hydrocephalus according to the present invention as illustrated in FIG. 41 and FIG. 42 differs from the seventeenth embodiment of the shunt valve for treatment of hydrocephalus according to the present invention as illustrated in FIG. 38 through FIG. 40 in that unlike the seventeenth embodiment of the shunt valve for treatment of hydrocephalus according to the present invention as illustrated in FIG. 38 through FIG. 40 where the inflow connector 234 is mounted in the shunt main body 232 which is covered by the silicone elastomer membrane 233 in its entirety, in a longitudinal direction of the cured plastic substrate 231 of the shunt valve for treatment of hydrocephalus 230, in the eighteenth embodiment as illustrated in FIG. 41 and FIG. 42, an inflow connector 254 is mounted so as to penetrate the cured plastic substrate 251 of the shunt valve for treatment of hydrocephalus 250 from the shunt main body 252 which is covered by the silicone elastomer membrane 253 in its entirety.

There are no other differences with the seventeenth embodiment of the shunt valve for treatment of hydrocephalus according to the present invention as illustrated in FIG. 38 through FIG. 40.

In FIG. 41 and FIG. 42, 254 denotes an inflow connector having a cylindrical shape and connecting a rear end of a ventricular catheter having a needle for tapping inside the ventricle attached to a leading end thereof, and 254A denotes a protrusion formed at a leading end of the inflow connector 254 and projecting to the outside. In FIG. 41 and FIG. 42, 255 denotes an outflow connector having a cylindrical shape and connecting a rear end of a peritoneal catheter inserted in the peritoneal cavity, and 255A denotes a protrusion formed at a leading end of the outflow connector 255 and projecting to the outside.

In FIG. 41 and FIG. 42, 256 denotes a first valve pressure variable device, 257 denotes a second valve pressure variable device, 258 denotes a third valve pressure variable device, 259 and 260 denote a first and second reservoir and 261 denotes a chamber.

An inflow connector 254 is mounted to a cerebrospinal fluid inflow side of the first valve pressure variable device 256. A ventricular catheter is connected to this inflow connector 254 and a peritoneal catheter is connected to the outflow connector 255.

The inflow connector 254 has a similar configuration with the inflow connector 234 of the seventeenth embodiment as illustrated in FIG. 38 through FIG. 40, and the outflow connector 255 has a similar configuration with the outflow connector 235 of the seventeenth embodiment as illustrated in FIG. 38 through FIG. 40.

The first valve pressure variable device 256 has a similar configuration with the first valve pressure variable device 236 of the seventeenth embodiment as illustrated in FIG. 38 through FIG. 40, the second valve pressure variable device 257 has a similar configuration with the second valve pressure variable device 237 of the seventeenth embodiment as illustrated in FIG. 38 through FIG. 40, and the third valve pressure variable device 258 has a similar configuration to the third valve pressure variable device 238 of the seventeenth embodiment as illustrated in FIG. 38 through FIG. 40.

The first and the second reservoirs 259 and 260 have a similar configuration to the first and second reservoirs 220 and 221 in the seventeenth embodiment as illustrated in FIG. 38 through FIG. 40. The first reservoir 259 is formed as a chamber (cavity) for accumulating a specific amount of cerebrospinal fluid and is provided over the first valve pressure variable device 256 and the second valve pressure variable device 257. Also, the second reservoir 260 is formed as a chamber (cavity) for accumulating a specific amount of cerebrospinal fluid and is provided over the second valve pressure variable device 257 and the third valve pressure variable device 258.

The upper wall of the first reservoir 259 and the side walls in a longitudinal direction of the shunt main body 252 are formed as first silicone side domes 253A and 253B on both sides in a longitudinal direction of the shunt main body 252, with the domes being made of a flexible silicone elastomer membrane 253 (soft silicone resin) raised in a dome shape and at the same time bulging out on both sides in a longitudinal direction of the shunt main body 252. When the first silicone side domes 253A and 253B are depressed, the cerebrospinal fluid is forced out of the first reservoir 259 into the first valve pressure variable device 256 and the second valve pressure variable device 257 connected thereto.

The upper wall of the second reservoir 260 and the side walls in a longitudinal direction of the shunt main body 252 are formed as second silicone side domes 253C and 253D on both sides in a longitudinal direction of the shunt main body, with the domes being made of a flexible silicone elastomer membrane 253 (soft silicone resin) raised in a dome shape and at the same time bulging out on both sides in a longitudinal direction of the shunt main body 252. When the second silicone side domes 253C and 253D are depressed, the cerebrospinal fluid is forced out of the second reservoir 241 into the second valve pressure variable device 257 and the second valve pressure variable device 258 connected thereto.

Following implantation of the shunt valve for treatment of hydrocephalus 250 under the scalp and in the vicinity of the pericranium, the first and second reservoirs 259 and 260 make it possible to harvest the cerebrospinal fluid accumulated therein and inject drug solutions such as contrast material and the like therein through a needle which is tapped from outside of the scalp into the membrane 253 forming the first and second silicone side domes 253A, 253B, 253C and 253D.

Chamber 261 has a similar configuration to chamber 242 of the seventeenth embodiment as illustrated in FIG. 38 through FIG. 40.

Chamber 261 prevents sudden outflow of the intraventricular cerebrospinal fluid and a sudden drop in the intraventricular pressure occurring when a patient suddenly sits up from a lying down position. The chamber 261 has a check valve which opens in the event the cerebrospinal fluid is forced to flow due to high intraventricular pressure, and closes when a negative pressure is created inside the peritoneal catheter to nullify the siphon effect of the cerebrospinal fluid. The chamber 261 has a cavity wherein the cerebrospinal fluid which normally drains out of the ventricles primarily accumulates when the valve closes due to the negative pressure.

The opening 20A of the second cover 20 is formed in the outflow tract 14B of the first valve pressure variable device 256 and will become the inflow side of the cerebrospinal fluid in the second valve pressure variable device 257 (refer to FIG. 5 and FIG. 6), on the cerebrospinal fluid outflow side of the first reservoir 259. The opening 20A of the second cover 20 which becomes the inflow side of the cerebrospinal fluid in the third valve pressure variable device 258 is formed in the outflow tract 25B which is the output side of the cerebrospinal fluid from the second valve pressure variable device 257, on the cerebrospinal fluid outflow side of the second reservoir 260 (refer to FIG. 5 and FIG. 6).

Chamber 260 is provided in the outflow tract 25B which is the cerebrospinal fluid output side of the third valve pressure variable device 258.

The relationship between the intraventricular pressure and the flow rate of the cerebrospinal fluid flowing out of the ventricles following adjustment of the first valve pressure variable device 256, the second valve pressure variable device 257 and the third valve pressure variable device 258 provided in the shunt valve for treatment of hydrocephalus 250 of the eighteenth embodiment of the present invention is similar to the seventeenth embodiment of the shunt valve for treatment of hydrocephalus according to the invention as illustrated in FIG. 38 through FIG. 40.

As the inflow connector 254 is provided so as to penetrate and extend downwards from the cured plastic substrate 251, the shunt valve for the treatment of hydrocephalus 250 according to the present invention as illustrated in FIG. 41 and FIG. 42 with the above-mentioned configuration is mounted as shown in FIG. 9.

Specifically, a small incision 31A is made in the skull 31 through surgery, the membrane between the skull 31 and the brain is opened, and the needle attached to the leading end of the ventricular catheter is inserted inside the lateral ventricle through the incision 31A and the rear end of the ventricular catheter is connected to the inflow connector 254. Then, the inflow connector 254 projecting downwards of the cured plastic substrate 251 is inserted into the incision 31A made in the skull 31 and is implanted between the scalp and the skull 31 (refer to FIG. 9).

Accordingly, the shunt valve for treatment of hydrocephalus according to the eighteenth embodiment of the present invention has the operation of the seventeenth embodiment of the shunt valve for treatment of hydrocephalus according to the present invention as illustrated in FIG. 38 through FIG. 40 and in addition, can help stabilize the shunt valve for treatment of hydrocephalus 250 which was implanted between the scalp and the skull 31.

Various modifications can be made to the invention without departing from the spirit and scope of the invention.

DESCRIPTION OF THE SYMBOLS

1 shunt valve for treatment of hydrocephalus
2 cured plastic substrate
3 shunt main body
4 membrane
5 inflow connector
6 outflow connector
7 first valve pressure variable device
8 second valve pressure variable device
9 first cover
9A opening
10 first valve main body
11 ball
12 rotor
12A legs
12B ball spring housing unit
12C rotor spring housing unit
13 plate
13A uneven portion
14 case
15 ball spring
16 rotor spring
20 second cover
20A opening
21 second valve main body
22 ball
23 rotor
23A legs
23B ball spring housing unit
23C rotor spring housing unit
24 plate
25 case
26 ball spring
27 rotor spring
47 chamber
63A silicone dome
68 ventricle-side occlude
69 reservoir
103A, 103B, 113A, 113B silicone side domes
168 third valve pressure variable device
200 first reservoir
201 second reservoir
213A, 213B first silicone side domes
213C, 213D second silicone domes

The invention claimed is:

1. A shunt valve for treatment of hydrocephalus which is implanted between the scalp and skull and serves for regulating a drainage amount of cerebrospinal fluid draining from brain ventricles where it is produced but is not fully absorbed and accumulates therein, when intraventricular pressure exceeds a certain pressure, such that intraventricular pressure is kept at a predetermined value, comprising:

a cured plastic substrate for stabilizing in a prescribed position in an outer periphery of the skull, at an inner side of the scalp;

an inflow connector formed in a cylindrical shape to which a rear end of a ventricular catheter is connected, said ventricular catheter having a needle for tapping inside the ventricles attached at a leading end thereof;

a first valve pressure variable device for regulating an increase and decrease of a flow rate of cerebrospinal fluid flowing in through said ventricular catheter, via said inflow connector and a first on-off valve by regulating said first on-off valve by changing a degree of aperture of said first on-off valve in accordance with changes in intraventricular pressure, and which is capable of changing an opening and closing pressure of said first on-off valve which sets a standard flow rate for a cerebrospinal fluid passing therethrough to a plurality of levels;

a second valve pressure variable device for regulating an increase and decrease of a flow rate of cerebrospinal fluid flowing in through a second on-off valve via an outflow tract of said first valve pressure variable device by regulating a second on-off valve by changing a degree of aperture of said second on-off valve in accordance with changes in the pressure of cerebrospinal fluid flowing out of said outflow tract of said first valve pressure variable device through said second on-off valve and draining out of said first valve pressure variable device, and which is capable of changing an opening and closing pressure of said second on-off valve which sets a standard flow rate for a cerebrospinal fluid passing therethrough to a plurality of levels; and an outflow connector formed in a cylindrical shape to which a rear end of a peritoneal catheter is connected, said peritoneal catheter having a leading end thereof inserted in a peritoneal cavity;

wherein said inflow connector, said first valve pressure variable device, said second valve pressure variable device and said outflow connector are mounted on said cured plastic substrate, and the device is covered by a flexible silicone elastomer membrane so as to form a flow path for the cerebrospinal fluid such that the cerebrospinal fluid flowing in from the inflow connector flows out through said first on-off valve of said first valve pressure device, and then flows out of the outflow tract in said second valve pressure variable device through said second on-off valve of said second valve pressure variable device, draining out of said outflow connector, and a lower end of said silicone elastomer membrane is tightly attached to said cured plastic substrate to form one integral unit.

2. The shunt valve for treatment of hydrocephalus according to claim 1, wherein said cured plastic substrate is made of polypropylene (PP), which is a thermoplastic resin very similar to high-density polyethylene, and has a low specific gravity, superior thermal resistance, strongly acidic and alkaline properties, resistance to repeated bending and great tensile strength.

3. The shunt valve for treatment of hydrocephalus according to claim 1, wherein
said inflow connector has an outer periphery of a cylindrical rear end thereof sealed by said silicone elastomer membrane and an end surface of said rear end thereof communicating with the first on-off valve of said first valve pressure variable device;
and has a protrusion projecting to the outside which is provided at a leading end thereof and prevents said ventricular catheter from easily disconnecting therefrom after a connector at the rear end of said ventricular catheter is attached by way of surgery.

4. The shunt valve for treatment of hydrocephalus according to claim 1, wherein
said first valve pressure variable device is comprised of a first cover and a first valve main body,
wherein
said first cover is made of a round cover and has an inlet port through which the cerebrospinal fluid flows inside; and
said first valve main body has an on-off valve for opening and closing said inlet port formed in said first cover and a management mechanism for opening and closing said on-off valve.

5. The shunt valve for treatment of hydrocephalus according to claim 4, wherein the inlet port formed in said first cover is an opening formed at the center of and penetrating the round cover from both sides, said opening allowing passage of the cerebrospinal fluid flowing in from said inflow connector and having a tapered shape, with a diameter thereof becoming larger starting from an outer wall surface of said first cover towards an inner wall surface thereof.

6. The shunt valve for treatment of hydrocephalus according to claim 4, wherein the on-off valve of said first valve main body has said opening formed in said first cover and a ball which is pushed against and fits in said opening from an inner wall side of said first cover.

7. The shunt valve for treatment of hydrocephalus according to claim 4, wherein the management mechanism of said first valve main body changes a clearance between an inner wall surface of said opening and said ball by changing the depressing force of said ball acting on said opening formed in said first cover, in accordance with changes in the pressure of the ventricular cerebrospinal fluid which is produced in the ventricles and accumulates therein.

8. The shunt valve for treatment of hydrocephalus according to claim 7, wherein
the management mechanism of said first valve main body comprises a rotor having a built-in magnet, a ball spring, a rotor spring, a case which houses said ball, said rotor, said ball spring and said rotor spring and has a stepwise plate formed in a bottom surface thereof, wherein
said rotor is formed as a disk shaped member having a magnet buried in one random location therein, and has a plurality of legs mounted on a lower surface thereof and projecting downwards, a ball spring housing unit which houses a lower end of said ball spring and a rotor spring housing unit which houses a lower end of said rotor spring which are provided on an upper surface thereof, and rotation thereof is made possible through a regulating device mounted on said plate inside said case using the attractive force between a magnetic pole of said magnet buried therein and its opposite magnetic pole;
said ball spring has a lower end thereof housed in a ball spring housing unit formed on an upper surface of said rotor and supports said ball at a leading end thereof, said ball being pushed against to fit in said opening in said first cover;
said rotor spring is comprised of a coiled spring and has a lower end thereof being housed in said rotor spring housing unit and an upper end thereof coming in contact with an inner upper wall of said first cover, and depresses said rotor against the plate of said case;
said case is formed of a bottomed cylindrical body having a circular cross section, and has a plate provided at a bottom thereof which is formed in a stepwise pattern, the respective heights of said steps differing by a certain amount, said plate having an uneven portion formed at a boundary of each step which latches together with the plurality of steps of said rotor to prevent said rotor from moving to a neighboring step position after having reached a specific step position, and an outflow tract provided in a side wall thereof through which the cerebrospinal fluid accumulated inside said case is discharged in a lower portion, wherein said case is tightly screwed together with said first cover;
and when said rotor rotates by a predetermined angle and moves upwards on the steps of said plate, said ball spring compresses and raises the depressing force which fits said ball in said opening in said first cover, while when said rotor rotates by a predetermined angle and moves downwards on the steps of said plate, said ball spring expands and weakens the depressing force which fits said ball in said opening in said first cover, and the depressing force of said ball against said opening formed in said first cover is caused to change to change a clearance between an inner wall surface of said opening and said ball.

9. The shunt valve for treatment of hydrocephalus according to claim 1,
wherein said second valve pressure variable device is constituted of a second cover and a second valve main body, wherein
said second cover is made of a round cover and has an inlet port through which the cerebrospinal fluid flows inside; and
said second valve main body has an on-off valve for opening and closing said inlet port formed in said first cover and a management mechanism for opening and closing said on-off valve.

10. The shunt valve for treatment of hydrocephalus according to claim 9, wherein the inlet port formed in said second cover is an opening formed at the center of and penetrating the round cover from both sides, said opening allowing passage of the cerebrospinal fluid flowing out from an outflow tract of said first valve pressure variable device and having a tapered shape, with a diameter thereof becoming larger starting from an outer wall surface of said second cover towards an inner wall surface thereof.

11. The shunt vale for treatment of hydrocephalus according to claim 9, wherein the on-off valve of said second valve main body consists of said opening formed in said second cover and a ball which is pushed against and fits in said opening from an inner wall side of said second cover.

12. The shunt valve for treatment of hydrocephalus according to claim 9, wherein the management mechanism of said second valve main body changes a clearance between an inner wall surface of said opening and said ball by changing the depressing force of said ball acting on said opening formed in said second cover, in accordance with changes in the pressure of the ventricular cerebrospinal fluid which is produced in the ventricles and accumulates therein.

13. The shunt valve for treatment of hydrocephalus according to claim 12, wherein
the management mechanism of said second valve main body comprises a rotor having a built-in magnet, a ball spring, a rotor spring, and a case which houses said ball, said rotor, said ball spring and said rotor spring and has a stepwise plate formed in a bottom surface thereof, wherein
said rotor is formed as a disk shaped member having a magnet buried in one random location therein, and has a plurality of legs mounted on a lower surface thereof and projecting downwards, a ball spring housing unit which houses a lower end of said ball spring and a rotor spring housing unit which houses a lower end of said rotor spring which are provided on an upper surface thereof, and rotation thereof is made possible through a regulating device mounted on said plate inside said case and using the attractive force between a magnetic pole of said magnet buried therein and its opposite magnetic pole;
said ball spring has a lower end thereof housed in a ball spring housing unit formed on an upper surface of said rotor and supports said ball at a leading end thereof, said ball being depressed against to fit in said opening in said second cover;
said rotor spring is comprised of a coiled spring and has a lower end thereof being housed in said rotor spring housing unit and an upper end thereof coming in contact with an inner upper wall of said second cover, and depresses said rotor against the plate of said case;
said case is formed of a bottomed cylindrical body having a circular cross section, and has a plate provided at a bottom thereof which is formed in a stepwise pattern, the respective heights of said steps differing by a certain amount, said plate having an uneven portion formed at a boundary of each step which latches together with the plurality of steps of said rotor to prevent said rotor from moving to a neighboring step position after having reached a specific step position, and an outflow tract provided in a side wall thereof through which the cerebrospinal fluid accumulated inside said case is discharged in a lower portion, wherein said case is tightly screwed together with said second cover;
and when said rotor rotates by a predetermined angle and moves upwards on the steps of said plate, said ball spring compresses and raises the depressing force which fits said ball in said opening in said second cover, while when said rotor rotates by a predetermined angle and moves downwards on the steps of said plate, said ball spring expands and weakens the depressing force which fits said ball in said opening in said second cover, and the depressing force of said ball against said opening formed in said second cover is caused to change to change a clearance between an inner wall surface of said opening and said ball.

14. The shunt valve for treatment of hydrocephalus according to claim 1, wherein
said outflow connector has an outer periphery of a cylindrical rear end thereof sealed by said silicone elastomer membrane and an end surface of said rear end thereof communicating with the outflow tract of said second valve pressure variable device;
and has a protrusion projecting to the outside which is provided at a leading end thereof and prevents a peritoneal catheter from easily disconnecting therefrom after a connector at the rear end of said peritoneal catheter is inserted inside the peritoneal cavity by way of surgery.

15. The shunt valve for treatment of hydrocephalus according to claim 1, wherein said outflow connector is provided on said cured plastic substrate and has a rear end thereof opening in an outflow tract of said second valve pressure variable device and a leading end thereof penetrating said cured plastic substrate and projecting downward from said cured plastic substrate.

16. The shunt valve for treatment of hydrocephalus according to claim 1, wherein
a chamber is provided between the outflow tract through which the cerebrospinal fluid of said second valve pressure variable device flows out and a rear end of said outflow connector,
said chamber having a check valve which opens in the event of a positive pressure when the cerebrospinal fluid is forced to flow due to high intraventricular pressure, and closes when a negative pressure is created inside the peritoneal catheter to nullify a siphon effect of the cerebrospinal fluid, and a cavity where the cerebrospinal fluid which normally drains out of the ventricles primarily accumulates when the valve closes due to the negative pressure.

17. The shunt valve for treatment of hydrocephalus according to claim 1, wherein a reservoir as well as a ventricle-side occluder are provided at a rear end of said inflow connector provided between said inflow connector and said first on-off valve of said first valve pressure variable device, wherein
said ventricle-side occluder is formed at a rear end of said inflow connector, integral with a membrane consisting of a flexible silicone elastomer having a cylindrical shape with an open top and a bottom, and serves to press-close a flow path through which the cerebrospinal fluid flows via said inflow connector, temporarily stopping the cerebrospinal fluid flow, and
said reservoir is formed as a cavity provided between an opening side of said ventricle-side occluder and said first valve pressure variable device, having an upper wall thereof constituted of a silicone dome formed of a membrane raised in a dome shape and made of a flexible silicone elastomer, and serves to accumulate a specific amount of cerebrospinal fluid which flows out from said ventricle-side occluder through said inflow connector.

18. The shunt valve for treatment of hydrocephalus according to claim 17, wherein said reservoir has an opening portion formed at a rear end of said inflow connector and is constituted of a silicone side dome formed of a membrane bulging out in a dome shape and made of a flexible silicone elastomer (soft silicone resin) and surrounding a side surface of said first valve pressure variable device.

19. The shunt valve for treatment of hydrocephalus according to claim 1, wherein a reservoir is provided between an outflow tract of said first valve pressure variable device and a second on-off valve of said second valve pressure variable device, said reservoir being formed as a cavity having an upper wall thereof constituted of a silicone dome formed of a membrane raised in a dome shape and made of a flexible silicone elastomer, and serves to accumulate a specific amount of cerebrospinal fluid which flows out from said first on-off valve of said first valve pressure variable device through said inflow connector.

20. The shunt valve for treatment of hydrocephalus according to claim 19, wherein
a chamber is provided between the outflow tract through which the cerebrospinal fluid of said second valve pressure variable device flows out and a rear end of said outflow connector, and
said chamber having a check valve which opens in the event of a positive pressure when the cerebrospinal fluid is forced to flow due to high intraventricular pressure, and closes when a negative pressure is created inside the peritoneal catheter to nullify a siphon effect of the cerebrospinal fluid, and a cavity where the cerebrospinal fluid which normally drains out of the ventricles primarily accumulates when the valve closes due to the negative pressure.

21. The shunt valve for treatment of hydrocephalus according to claim 19, wherein said reservoir is arranged to stretch over both side surfaces of said first valve pressure variable device and second valve pressure variable device which are connected and has an outflow tract formed in said first valve pressure variable device and a second on-off valve formed in the second valve pressure variable device, adjacent to a lining-up direction of said first valve pressure variable device and said second valve pressure variable device and is constituted of silicone side domes formed of a flexible silicone elastomer (soft silicone resin) membrane bulging out in a dome shape on both sides in a lining-up direction of said first valve pressure variable device and said second valve pressure variable device.

22. The shunt valve for treatment of hydrocephalus according to claim 1, wherein
a third valve pressure variable device is provided on an outflow tract side of said first valve pressure variable device and serves to regulate an increase or decrease in the flow rate of the cerebrospinal fluid flowing in from a third on-off valve through the outflow tract of said second valve pressure variable device by changing a degree of aperture in said second on-off valve in accordance with a change in the pressure of the cerebrospinal fluid flowing in from the outflow tract of said second valve pressure variable device through said third on-off valve and out of said second valve pressure variable device, and is capable of changing an opening and closing pressure of said third on-off valve which sets a standard flow rate for a cerebrospinal fluid passing therethrough to a plurality of levels;
wherein said inflow connector, said first valve pressure variable device, said second valve pressure variable device, said third valve pressure variable device and said outflow connector are mounted on said cured plastic substrate, and the device is covered by a flexible silicone elastomer membrane so as to form a flow path for the cerebrospinal fluid between said inflow connector and said outflow connector such that the cerebrospinal fluid flowing in from said inflow connector flows through said first on-off valve of said first valve pressure device and out of the outflow tract in said first valve pressure variable device, then passes through said second on-off valve of said second valve pressure variable device and flows out from the outflow tract of said second valve pressure variable device, and finally passes through said third on-off valve of the third valve pressure variable device and flows out of the outflow tract of said third valve pressure variable device, draining out from said outflow connector, with a lower end of said silicone elastomer membrane being tightly attached to said cured plastic substrate to form one integral unit therewith.

23. The shunt valve for treatment of hydrocephalus according to claim 22, wherein said third valve pressure variable device is comprised of a third cover and a third valve main body,
wherein
said third cover is made of a round cover and has an inlet port through which the cerebrospinal fluid flows inside; and
said third valve main body has an on-off valve for opening and closing said inlet port formed in said third cover and a management mechanism for opening and closing said on-off valve.

24. The shunt valve for treatment of hydrocephalus according to claim 23, wherein the inlet port formed in said third cover is an opening at the center of and penetrating the round cover from both sides, said opening allowing passage of the cerebrospinal fluid flowing out from an outflow tract of said second valve pressure variable device and having a tapered shape, with a diameter thereof becoming larger starting from an outer wall surface of said third cover towards an inner wall surface thereof.

25. The shunt valve for treatment of hydrocephalus according to claim 23, wherein the on-off valve of said third valve main body has said opening formed in said third cover and a ball which is pushed against and fits in said opening from an inner wall side of said third cover.

26. The shunt valve for treatment of hydrocephalus according to claim 23, wherein the management mechanism of said third valve main body changes a clearance between an inner wall surface of said opening and said ball by changing the depressing force of said ball acting on said opening formed in said third cover, in accordance with changes in the pressure of the ventricular cerebrospinal fluid which is produced in the ventricles and accumulates therein.

27. The shunt valve for treatment of hydrocephalus according to claim 26, wherein
the management mechanism of said third valve main body comprises a rotor having a built-in magnet, a ball spring, a rotor spring and a case which houses said ball, said rotor, said ball spring and said rotor spring and has a stepwise plate formed in a bottom surface thereof, wherein
said rotor is formed as a disk shaped member having a magnet buried in one random location therein, and has a plurality of legs mounted on a lower surface thereof and projecting downwards, a ball spring housing unit which houses a lower end of said ball spring and a rotor spring housing unit which houses a lower end of said rotor spring which are provided on an upper surface thereof, and rotation thereof is made possible through a regulating device mounted on said plate inside said case using the attractive force between a magnetic pole of said magnet buried therein and its opposite magnetic pole;
said ball spring has a lower end thereof housed in a ball spring housing unit formed on an upper surface of said rotor and supports said ball at a leading end thereof, said ball being pushed against to fit in said opening in said third cover;
said rotor spring is comprised of a coiled spring and has a lower end thereof being housed in said rotor spring housing unit and an upper end thereof coming in contact with an inner upper wall of said first cover, and depresses said rotor against the plate of said case;

said case is formed of a bottomed cylindrical body having a circular cross section, and has a plate provided at a bottom thereof which is formed in a stepwise pattern, the respective heights of said steps differing by a certain amount, said plate having an uneven portion formed at a boundary of each step which latches together with the plurality of steps of said rotor to prevent said rotor from moving to a neighboring step position after having reached a specific step position, and an outflow tract provided in a side wall thereof through which the cerebrospinal fluid accumulated inside said case is discharged in a lower portion, wherein said case is tightly screwed together with said third cover;

and when said rotor rotates by a predetermined angle and moves upwards on the steps of said plate, said ball spring compresses and raises the depressing force which fits said ball in said opening in said third cover, while when said rotor rotates by a predetermined angle and moves downwards on the steps of said plate, said ball spring expands and weakens the depressing force which fits said ball in said opening in said third cover, and the depressing force of said ball against said opening formed in said third cover is caused to change to change a clearance between an inner wall surface of said opening and said ball.

28. The shunt valve for treatment of hydrocephalus according to claim 22, wherein a reservoir as well as a ventricle-side occluder are provided at a rear end of said inflow connector provided between said inflow connector and said first on-off valve of said first valve pressure variable device, and a chamber is provided between an outflow tract through which the cerebrospinal fluid flows out from said third valve pressure variable device and a rear end of said outflow connector wherein said ventricle-side occluder is formed at a rear end of said inflow connector, integral with a membrane consisting of a flexible silicone elastomer having a cylindrical shape with an open top and a bottom, and serves to press-close a flow path through which the cerebrospinal fluid flows via said inflow connector, temporarily stopping the cerebrospinal fluid flow, said reservoir is formed as a cavity provided between an opening side of said ventricle-side occluder and said first valve pressure variable device, having an upper wall thereof constituted of a silicone dome formed of a membrane raised in a dome shape and made of a flexible silicone elastomer, and serves to accumulate a specific amount of cerebrospinal fluid which flows out from said ventricle-side occluder through said inflow connector, and said chamber having a check valve which opens in the event of a positive pressure when the cerebrospinal fluid is forced to flow due to high intraventricular pressure, and closes when a negative pressure is created inside the peritoneal catheter to nullify a siphon effect of the cerebrospinal fluid, and a cavity where the cerebrospinal fluid which normally drains out of the ventricles primarily accumulates when the valve closes due to the negative pressure.

29. The shunt valve for treatment of hydrocephalus according to claim 22, wherein a first reservoir as well as a ventricle-side occluder are provided at a rear end of said inflow connector provided between said inflow connector and said first on-off valve of said first valve pressure variable device, a second reservoir is provided between the outflow tract of said first valve pressure variable device and the second on-off valve of said second valve pressure variable device, and the outflow tract of said second valve pressure variable device and the third on-off valve of said third valve pressure variable device, and a chamber is provided between the outflow tract through which the cerebrospinal fluid flows out of said third valve pressure variable device and a rear end of said outflow connector, wherein said ventricle-side occluder is formed at a rear end of said inflow connector, integral with a membrane consisting of a flexible silicone elastomer having a cylindrical shape with an open top and a bottom, and serves to press-close a flow path through which the cerebrospinal fluid flows via said inflow connector, temporarily stopping the cerebrospinal fluid flow, said first reservoir is formed as a cavity provided between the outflow tract of said first valve pressure variable device and the second on-off valve of said second valve pressure variable device, having an upper wall thereof constituted of a silicone dome formed of a membrane raised in a dome shape and made of a flexible silicone elastomer, and serves to accumulate a specific amount of cerebrospinal fluid which circulates inside said first valve pressure variable device and flows out from the second on-off valve of said second valve pressure variable device, said second reservoir is formed as a cavity provided between the outflow tract of said second valve pressure variable device and the third on-off valve of said third valve pressure variable device, having an upper wall thereof constituted of a silicone dome formed of a membrane raised in a dome shape and made of a flexible silicone elastomer, and serves to accumulate a specific amount of cerebrospinal fluid which circulates inside said second valve pressure variable device and flows out from the third on-off valve of said third valve pressure variable device, and said chamber has a check valve which opens in the event of a positive pressure when the cerebrospinal fluid is forced to flow due to high intraventricular pressure, and closes when a negative pressure is created inside the peritoneal catheter to nullify a siphon effect of the cerebrospinal fluid, and a cavity where the cerebrospinal fluid which normally drains out of the ventricles primarily accumulates when the valve closes due to the negative pressure.

30. The shunt valve for treatment of hydrocephalus according to claim 22, wherein a first reservoir as well as a ventricle-side occluder are provided at a rear end of said inflow connector provided between said inflow connector and said first on-off valve of said first valve pressure variable device, and a second reservoir is provided between the outflow tract of said first valve pressure variable device and the second on-off valve of said second valve pressure variable device, and the outflow tract of said second valve pressure variable device and the third on-off valve of said third valve pressure variable device, wherein said ventricle-side occluder is formed at a rear end of said inflow connector, integral with a membrane consisting of a flexible silicone elastomer having a cylindrical shape with an open top and a bottom, and serves to press-close a flow path through which the cerebrospinal fluid flows via said inflow connector, temporarily stopping the cerebrospinal fluid flow, said first reservoir is arranged to stretch over both side surfaces of said first valve pressure variable device and second valve pressure variable device which are connected and have an outflow tract formed in said first valve pressure variable device and a second on-off valve formed in the second valve pressure variable device, adjacent to a lining-up direction of said first valve pressure variable device and said second valve pressure variable device and forms a first silicone side dome comprised of a flexible silicone elastomer (soft silicone resin) membrane bulging out in a dome shape on both sides in a lining-up direction of said first valve pressure variable device and said second valve pressure variable device and serves to accumulate a specific amount of cerebrospinal fluid which circulates inside said first valve pressure variable device and flows out from the outflow tract of said first valve pressure variable device, said second reservoir is arranged to stretch over both side surfaces of said second valve pressure variable device and third valve pressure variable device which are connected and have an outflow tract formed in said second valve pressure variable device and a third on-off valve formed in the third valve pressure variable device, adjacent to a lining-up direction of said second valve pressure variable device and said third valve pressure variable device and forms a second silicone side dome comprised of a flexible silicone elastomer (soft silicone resin) membrane bulging out in a dome shape on both sides in a lining-up direction of said second valve pressure variable device and said third valve pressure variable device and serves to accumulate a specific amount of cerebrospinal fluid which circulates inside said second valve pressure variable device and flows out from the outflow tract of said second valve pressure variable device, and said second reservoir and first reservoir are provided independently from and without communicating with each other.

31. The shunt valve for treatment of hydrocephalus according to claim 30, wherein a chamber is provided between an outflow tract through which the cerebrospinal fluid flows out of said third valve pressure variable device and a rear end of said outflow connector and said chamber has a check valve which opens in the event of a positive pressure when the cerebrospinal fluid is forced to flow due to high intraventricular pressure, and closes when a negative pressure is created inside the peritoneal catheter to nullify a siphon effect of the cerebrospinal fluid, and a cavity where the cerebrospinal fluid which normally drains out of the ventricles primarily accumulates when the valve closes due to the negative pressure.

32. The shunt valve for treatment of hydrocephalus according to claim 22, wherein said outflow connector is provided on said cured plastic substrate and has a rear end thereof opening in an outflow tract of said third valve pressure variable device and a leading end thereof penetrating said cured plastic substrate and projecting downward from said cured plastic substrate.

* * * * *